(12) United States Patent
Hatanaka et al.

(10) Patent No.: US 8,048,667 B2
(45) Date of Patent: Nov. 1, 2011

(54) HYBRID ALPHA-GLUCOSIDE TRANSPORTER

(75) Inventors: Haruyo Hatanaka, Osaka (JP); Fumihiko Omura, Osaka (JP)

(73) Assignee: Suntory Holdings Limited, Osaka (JP)

( * ) Notice: Subject to any disclaimer, the term of this patent is extended or adjusted under 35 U.S.C. 154(b) by 229 days.

(21) Appl. No.: 12/442,131

(22) PCT Filed: Sep. 9, 2008

(86) PCT No.: PCT/JP2008/066239
§ 371 (c)(1), (2), (4) Date: Mar. 20, 2009

(87) PCT Pub. No.: WO2010/029610
PCT Pub. Date: Mar. 18, 2010

(65) Prior Publication Data
US 2010/0272855 A1    Oct. 28, 2010

(51) Int. Cl.
*C12N 1/19* (2006.01)
*C12N 15/63* (2006.01)
*C07H 21/04* (2006.01)

(52) U.S. Cl. .................. 435/254.2; 435/320.1; 536/23.1

(58) Field of Classification Search .................. None
See application file for complete search history.

(56) References Cited

FOREIGN PATENT DOCUMENTS
JP    6-245750    9/1994

OTHER PUBLICATIONS

Dietvorst et al. "Maltotriose Utilization in Lager Yeast Strains: *MTT1* Encodes a Maltotriose Transporter" (2005) *Yeast* 22(10):775-788.

Medintz et al. "A PEST-like Sequence in the N-Terminal Cytoplasmic Domain of *Saccharomyces* Maltose Permease is Required for Glucose-Induced Proteolysis and Rapid Inactivation of Transport Activity" (2000) *Biochemistry* 39(15):4518-4526.

Gadura et al. "Sequences in the N-terminal Cytoplasmic Domain of *Saccharomyces cerevisiae* Maltose Permease are Required for Vacuolar Degradation but not Glucose-Induced Internalization" (2006) *Curr. Genet.* 50(2): 101-114.

Kodama et al. "Improvement of Maltose Fermentation Efficiency: Constitutive Expression of *MAL* Genes in Brewing Yeasts" (1995) *J. Am. Soc. Brew. Chem.* (1995) 53(1):24-29.

Han et al. "Characterization of the *AGT1* Encoding a General α-Glucoside Transporter from *Saccharomyces*" (1995) *Molecular Microbiology* 17(6):1093-1107.

Brondijk et al. "Catabolite Inactivation of Wild-type and Mutant Maltose Transport Proteins in *Saccharomyces cerevisiae*" (1998). *J. Biol. Chem.* 273(25):15352-15357.

U.S. Appl. No. 12/442,143 to Hatanaka et al., entitled "Glucose-Induced Inactivation/Degradation-Resistant Transporter Gene and Use Thereof" which application is the National Stage of PCT/JP2008/066237, filed Sep. 9, 2008.

U.S. Appl. No. 12/442,121 to Hatanaka et al., entitled "Glucose-Induced Inactivation/Degradation-Resistant Transporter Gene and Use Thereof" which application is the National Stage of PCT/JP2008/066241, filed Sep. 9, 2008.

*Primary Examiner* — Ruixiang Li
(74) *Attorney, Agent, or Firm* — Greenblum & Bernstein, PLC

(57) ABSTRACT

The present invention relates to alpha-glucoside transporters which can promote assimilation of maltose/maltotriose contained in wort, etc., and so on. Especially in relation to glucose-induced inactivation/degradation, the present invention relates to alpha-glucoside transporters which are less susceptible to glucose-induced inactivation/degradation and can take up maltotriose like AGT1, by constructing the hybrid of AGT1 and MAL21. By using, e.g., a yeast expressing the alpha-glucoside transporter of the present invention, the fermentation rate of moromi mash containing oligosaccharides such as maltose/maltotriose can be accelerated.

7 Claims, 11 Drawing Sheets

```
   1 ATGAAGGGAT TATCCTCATT AATAAACAGA AAAAAAGACA GGAACGACTC
  51 ACACTTAGAT GAGATCGAGA ATGGCGTGAA CGCTACCGAA TTCAACTCGA
 101 TAGAGATGGA GGAGCAAGGT AAGAAAAGTG ATTTTGGTCT TTCCCATCAT
 151 GAGTACGGTC CAGGTTCACT AATACCAAAC GATAATAATG AAGAAGTCCC
 201 CGACCTTCTC GATGAAGCTA TGCAGGACGC CAAAGAGGCA GATGAAAGTG
 251 AGAGGGGAAT GCCACTCATG ACAGCTTTGA AGACATATCC AAAAGCTGCT
 301 GCTTGGTCAC TATTAGTTTC CACAACATTG ATTCAAGAGG GTTATGACAC
 351 AGCCATTCTA GGAGCTTTCT ATGCCCTGCC TGTTTTTCAA AAAAAATATG
 401 GTTCTTTGAA TAGCAATACA GGAGATTATG AAATTTCAGT TTCTTGGCAA
 451 ATCGGTCTAT GTCTATGCTA CATGGCAGGT GAAATTGTGG GGCTACAGCT
 501 AACGGGGCCC TCCGTGGATC TTGTTGGAAA TCGTTACACA TTGATCATGG
 551 CGTTGTTCTT TTTAGCGGCT TTCATTTTCA TTCTGTATTT TTGCAAGAGT
 601 TTGGGTATGA TTGCCGTGGG ACAGGCATTG TGTGGTATGC CATGGGGTTG
 651 TTTCCAATGT TTGACCGTTT CTTATGCTTC TGAAATTTGT CCTTTGGCCC
 701 TAAGATACTA TTTGACGACT TATTCTAATT TATGTTGGAC GTTCGGTCAA
 751 CTTTTCGCTG CTGGTATTAT GAAAAATTCC CAGAACAAAT ATGCCAACTC
 801 AGAACTAGGA TATAAGCTAC CTTTTGCTTT GCAGTGGATC TGGCCCCTTC
 851 CTTTGGCGGT AGGTATTTTT TTTGCACCAG AGTCTCCATG GTGGCTGGTT
 901 AAAAAAGGAA GGATTGATCA AGCGAGGAGA TCACTTGAAA GAACATTAAG
 951 TGGTAAAGGA CCCGAGAAAG AATTACTAGT GACTATGGAA CTCGATAAAA
1001 TCAAAACTAC TATAGAAAAG GAGCAGAAAA TGTCTGATGA AGGAACTTAC
1051 TGGGATTGTG TGAAAGATGG TATTAACAGG AGAAGAACGA GAATAGCTTG
1101 TTTATGTTGG ATCGGTCAAT GCTCCTGTGG TGCATCATTA ATTGGTTATT
1151 CAACTTACTT TTATGAAAAA GCTGGTGTTA GCACTGATAC GGCTTTTACT
1201 TTCAGTATTA TCCAATATTG TCTTGGTATT GCTGCAACGT TTGTATCCTG
1251 GTGGGCTTCA AAATATTGTG GCAGATTTGA CCTTTATGCT TTTGGGCTGG
1301 CTTTTCAGGC TATTATGTTC TTCATTATCG GTGGTTTAGG ATGTTCAGAC
1351 ACTCATGGCG CTAAAATGGG TAGTGGTGCT CTTCTAATGG TTGTCGCGTT
1401 CTTTTACAAC CTCGGTATTG CACCTGTTGT TTTTTGCTTA GTGTCTGAAA
1451 TGCCGTCTTC AAGGCTAAGA ACCAAAACAA TTATTTTGGC TCGTAATGCT
1501 TACAATGTGA TCCAAGTTGT AGTTACAGTT TTGATTATGT ACCAATTGAA
1551 CTCAGAGAAA TGGAATTGGG GTGCTAAATC AGGCTTTTTC TGGGGAGGAT
1601 TTTGTCTGGC CACTTTAGCT TGGGCTGTTG TCGATTTACC AGAAACCGCT
1651 GGCAGGACTT TTATTGAGAT AAATGAATTG TTTAGACTTG GTGTTCCAGC
1701 AAGAAAGTTC AAGTCGACTA AAGTCGACCC TTTTGCAGCT GCCAAAGCAG
1751 CAGCTGCAGA AATTAATGTT AAAGATCCGA AGGAAGATTT GGAAACTTCT
1801 GTGGTAGATG AAGGGCGAAA CACCTCATCT GTTGTGAACA AATGA
```

FIG. 1: Nucleotide sequence of MAL21 gene

```
MKGLSSLINRKKDRNDSHLDEIENGVNATEFNSIEMEEQGKKSDFGLSHH  50

EYGPGSLIPNDNNEEVPDLLDEAMQDAKEADESERGMPLMTALKTYPKAA  100

AWSLLVSTTLIQEGYDTAILGAFYALPVFQKKYGSLNSNTGDYEISVSWQ  150

IGLCLCYMAGEIVGLQLTGPSVDLVGNRYTLIMALFFLAAFIFILYFCKS  200

LGMIAVGQALCGMPWGCFQCLTVSYASEICPLALRYYLTTYSNLCWTFGQ  250

LFAAGIMKNSQNKYANSELGYKLPFALQWIWPLPLAVGIFFAPESPWWLV  300

KKGRIDQARRSLERTLSGKGPEKELLVTMELDKIKTTIEKEQKMSDEGTY  350

WDCVKDGINRRRTRIACLCWIGQCSCGASLIGYSTYFYEKAGVSTDTAFT  400

FSIIQYCLGIAATFVSWWASKYCGRFDLYAFGLAFQAIMFFIIGGLGCSD  450

THGAKMGSGALLMVVAFFYNLGIAPVVFCLVSEMPSSRLRTKTIILARNA  500

YNVIQVVVTVLIMYQLNSEKWNWGAKSGFFWGGFCLATLAWAVVDLPETA  550

GRTFIEINELFRLGVPARKFKSTKVDPFAAAKAAAAEINVKDPKEDLETS  600

VVDEGRNTSSVVNK*
```

FIG. 2: Amino acid sequence of Mal21p

```
                                                               50
AGT1p   (1)   MKN ISL S KKAASKNEDKNIS SSRDIVNQQEVFNTEDFEEGKKDSAF
MAL21p  (1)   MKG SSL N K----KDRNDSHL EIENGVNATEFNSIEMEEQGK-KSDF
                                                              100
AGT1p   (51)  ELDHLE TTNSAQLGDSDE NEN NEMNATDDANEANSEE SMTLKQAL
MAL21p  (46)  GLSHHE GPGSLIPNDNNE VPD DEA--MQDAKEADESE GMPLMTAL
                         TMD1 ✛                                150
AGT1p   (101) LKYPKAALWS LVSTTL MEGYDTA LSALYALPVFQ K G LNG-EGSY
MAL21p  (94)  KTYPKAAAWS LVSTTL QEGYDTA LGAFYALPVFQ K G LNSNTGDY
                                                              200
AGT1p   (150) EI SQWQIGLN CV CGE GLQ TTYMV F GNRYT ITALGLLTA IF
MAL21p  (144) EI VSWQIGLC CY AGE GLQ TGPSV L GNRYT IMALFFLAA IF
                                                              250
AGT1p   (200) ILY CKSL MIAVGQILS PWGCFQSLAV YASE CPLALRYY T YSN
MAL21p  (194) ILY CKSL MIAVGQALC PWGCFQCLTV YASE CPLALRYY T YSN
                                                              300
AGT1p   (250) CWLFGQ FA GIMKNSQENL NS LGYKLPFALQWIWPAPLM GIFFAP
MAL21p  (244) CWTFGQ FA GIMKNSQNKY NS LGYKLPFALQWIWPLPLA GIFFAP
                                                              350
AGT1p   (300) ESPWWLV KDR AEAR SLSRILSGKGAEK QVD TLKQIELTIEKERL
MAL21p  (294) ESPWWLV KGR DQAR SLERTLSGKGPEK LVT ELDKIKTTIEKEQK
                                                              400
AGT1p   (350) SKSGS FNCFKG NGRRTR ACLTW QNSSGAVL GYSTYF E AG
MAL21p  (344) DEGTY DCVKDG NRRRTR ACLCW QCSCGASL GYSTYF E AG
                                                              450
AGT1p   (400) TDKAFTFS IQYCLG A TLCSWVISGRVGR T LT GLAFQM CLFII
MAL21p  (394) TDTAFTFS IQYCLG A TFVSWWASKYCGR D YA GLAFQA MFFII
                                                              500
AGT1p   (450) GG GFGSGSSASNG G LL A FFYNAGI AVV C V E PS ELRTKT
MAL21p  (444) GG GCSDTHGAKMG G LL V FFYNLGI PVV C V E PS RLRTKT
                                                     TMD12    550
AGT1p   (500) I LARICYN AV NA LTPYMLNVSDWNWGAK GL WGGFTAVTLAWV
MAL21p  (494) I LARNAYN QV VT LIMYQLNSEKWNWGAK GF WGGFCLATLAWA
                           ✛                                  600
AGT1p   (550) DLPETTGRTFSEINELFNQGVPARKFASTVVDPF K K--TQHDS ADE
MAL21p  (544) DLPETAGRTFIEINELFRLGVPARKFKSTKVDPF A KAAAAEIN KDP
                                          622
AGT1p   (598) SISQS S KQRELNA DKC---
MAL21p  (594) KEDLE S VDEGRNT SVVNK-
```

FIG. 3

```
                                                                     50
MAL21p   (1)   MKGLSSLINRKKDRNDSHLDEIENGVNATEFNSIEMEEQGKKSDFGLSHH
MTT1p    (1)   MKGLSSLINRKKDRNDSHLDEIENGVNATEFNSIEMEEQGKKSDFDLSHH
                                                                    100
MAL21p  (51)   EYGPGSLIPNDNNEEVPDLLDEAMQDAKEADESERGMPLMTALKTYPKAA
MTT1p   (51)   EYGPGSLTPNDNNEEVPDLLDEAMQDAKEADESERGMPLMTALKTYPKAA
                       TMD1                                         150
MAL21p (101)   AWSLLVSTTLIQEGYDTAILG FYALPVFQKKYGSLNSNTGDYEISVSWQ
MTT1p  (101)   AWSLLVSTTLIQEGYDTAILG FYALPVFQKKYGSLNSNTGDYEISASWQ
                                                                    200
MAL21p (151)   IGLCLCYMAGEIVGLQ TGPSVDL GNRYTLI ALFFLAAFIFILYFCKS
MTT1p  (151)   IGLSLCVTAGEIVGLQ TGPFVDY GNRYTLI ALILLAAFTFILYFCKG
                                                                    250
MAL21p (201)   LGMIAVGQALCGMPWGCFQCLTVSYASEICP ALRYYLTTYSNLCWTFGQ
MTT1p  (201)   LGMIAVGQVLCGMPWGCFQCLTVSYASEICP ALRYYLTTYSNLCWTFGQ
                                                                    300
MAL21p (251)   LFAAGIMKNSQNKYANSELGYKLPFALQWIWPLPLA GIFFAPESPWWLV
MTT1p  (251)   LFAAGIMKNSQNKYPNSELGYKLPFALQWIWPAPLA GIFFAPESPWWLV
                                                                    350
MAL21p (301)   KKGRIDQARRSLERTLSGKGPEKELLV MELDKIKTTIEKEQK SD-EG
MTT1p  (301)   KKGRIDQARRSLERTLSGKGPEKELLV MELDNIKVTIEKEKK SDSEG
                                                                    400
MAL21p (350)   YWDC KDG NRRRTRIACLCW GQC CGASLIGYSTYFYEKAGVSTDTAF
MTT1p  (351)   YWDC KDS NRRRTRIACLCW GQT CGTSLIGNSTYFYEKAGVGTDTAF
                                                                    450
MAL21p (400)   TFSIIQYCLGIAATF SWWASKYCGRFDLYAFGLAFQA MFFIIGGLGCS
MTT1p  (401)   TFSIIQYCLGIAATF SWWASKYFGRFDLYAFGLAIQT SLFIIGGLGCS
                                                                    500
MAL21p (450)   D HGAKMGSG LLMV FFYNLGIAPVVFCLVSE PSSRLRTK IILARN
MTT1p  (451)   D HGAEMGSG LLMV FFYNLGIAPVVFCLVSE PSSRLRTK IILARN
                                                      TMD12         550
MAL21p (500)   AYN IQ VVTVLIMYQLNSEKWNWGAKSGFFWGGFCLATLAWAV DLPET
MTT1p  (501)   AYN AS VTTVLIMYQLNSEKWNWGAKSGFFWGGLCFATLVWAV DLPET
                                                                    600
MAL21p (550)   AGRTFIEINELFRLGVPARKFKSTKVDPFAAAKAAAAEINVKDPKEDLET
MTT1p  (551)   AGRTFIEINELFRLGVPARKFKSTKVDPFAAAKAAAAEINVKDPKEDLET
                         616
MAL21p (600)   SVVDEGRNTSSVVNK-
MTT1p  (601)   SVVDEGRSTPSVVNK-

————— : recombinable sites
```

FIG. 4

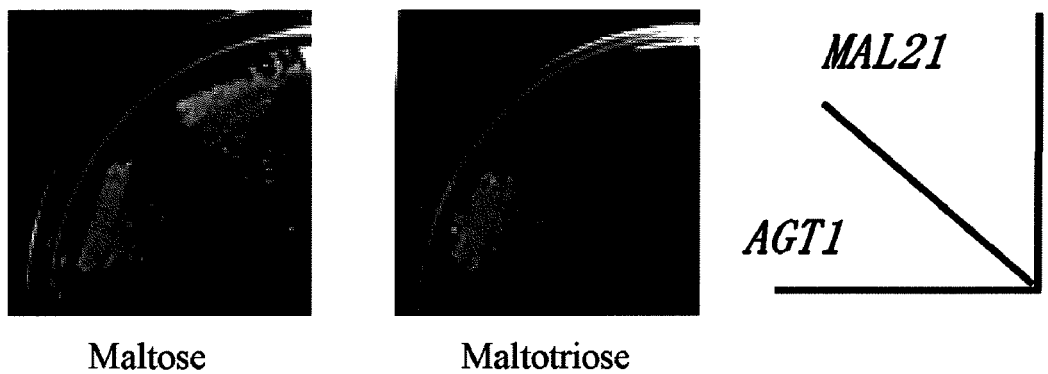
FIG. 5: Differences in substrate specificity between Agt1p and Mal21p
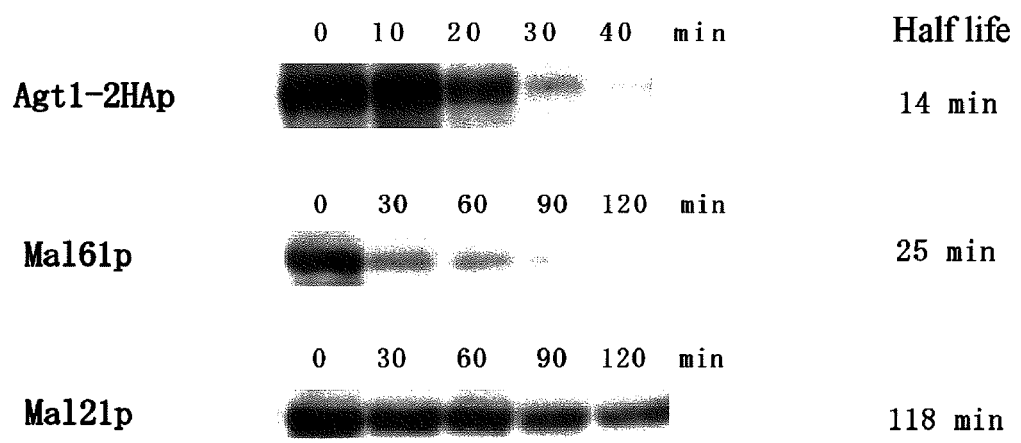
FIG. 6: Differences in glucose-induced degradation rates of Agt1p, Mal61p and Mal21p

| Hybrid transporter | Ligated fragments | Schematic diagram of transporter gene |
|---|---|---|
| AAM | AGT1—SaK、MAL21—KB | |
| AMA | AGT1—SaS、MAL21—SK、AGT1—KB | |
| AMM | AGT1—SaS、MAL21—SB | |
| MAA | MAL21—SaS、AGT1—SK | |
| MAM | MAL21—SaS、AGT1—SK、MAL21—KB | |
| MMA | MAL21—SaK、AGT1—KB | |
▨ : AGT1-derived fragment   ☐ : MAL21-derived fragment
FIG. 7: Fragments used to produce hybrid transporter genes
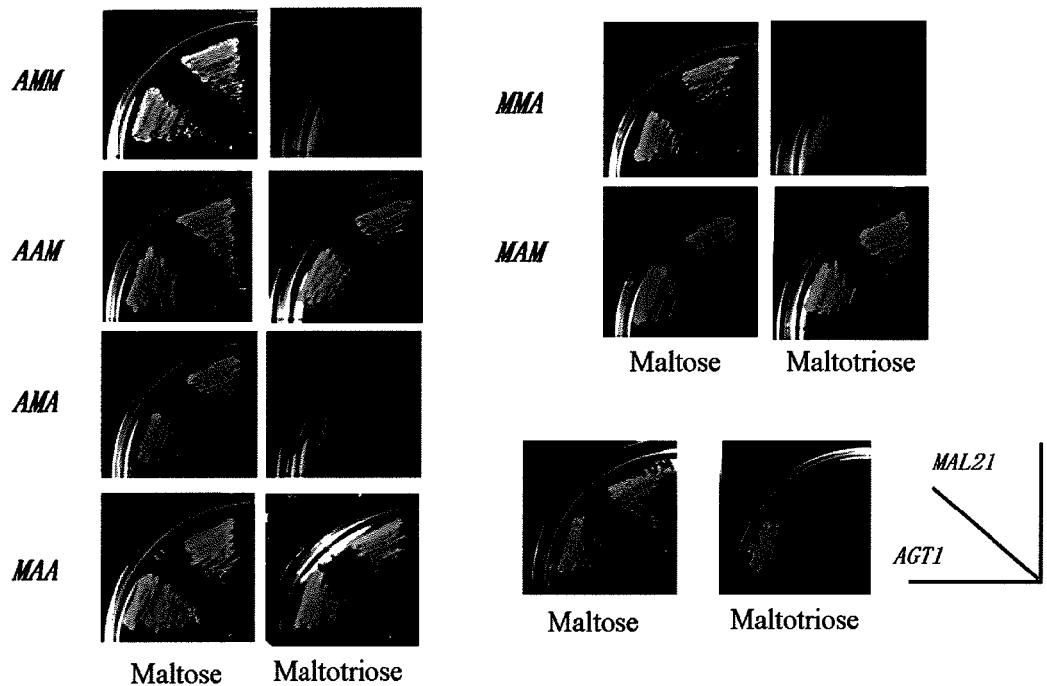
FIG. 8: Substrate specificity of each hybrid transporter

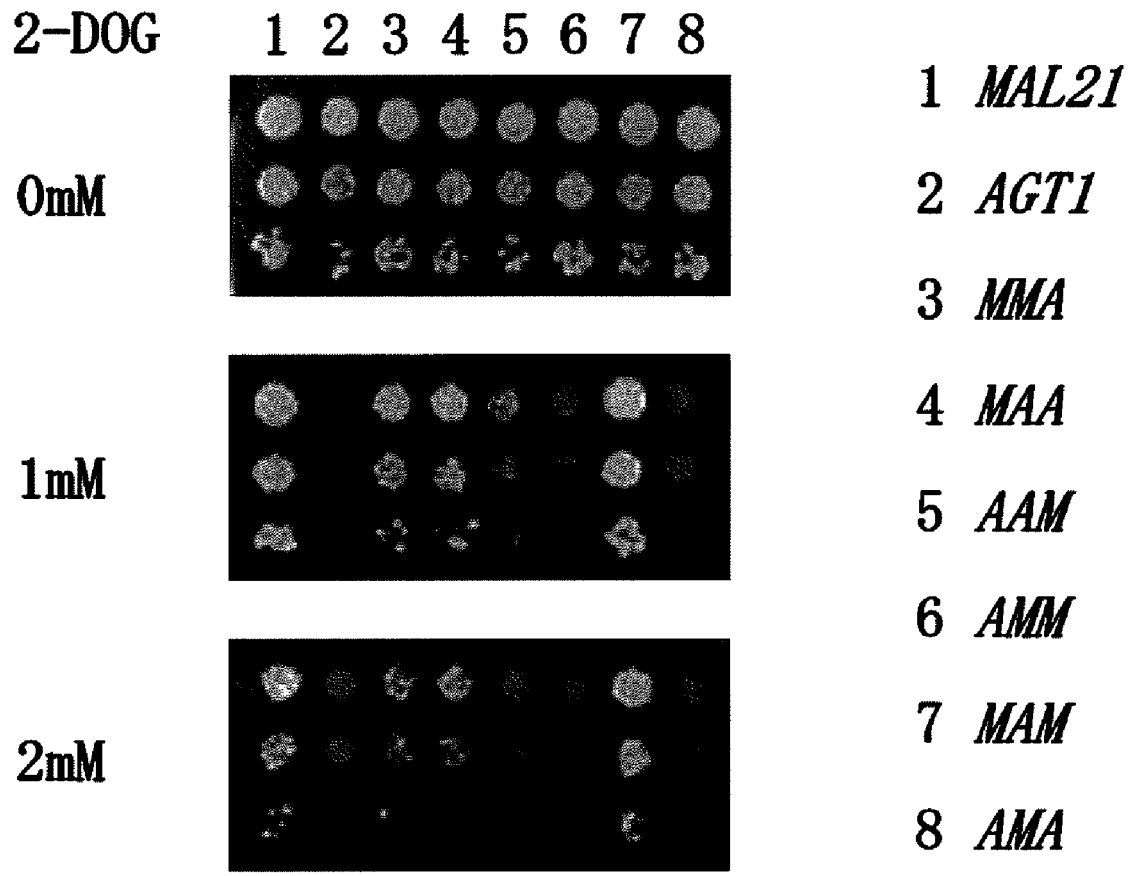
FIG. 9: 2-DOG Resistance of hybrid transporter

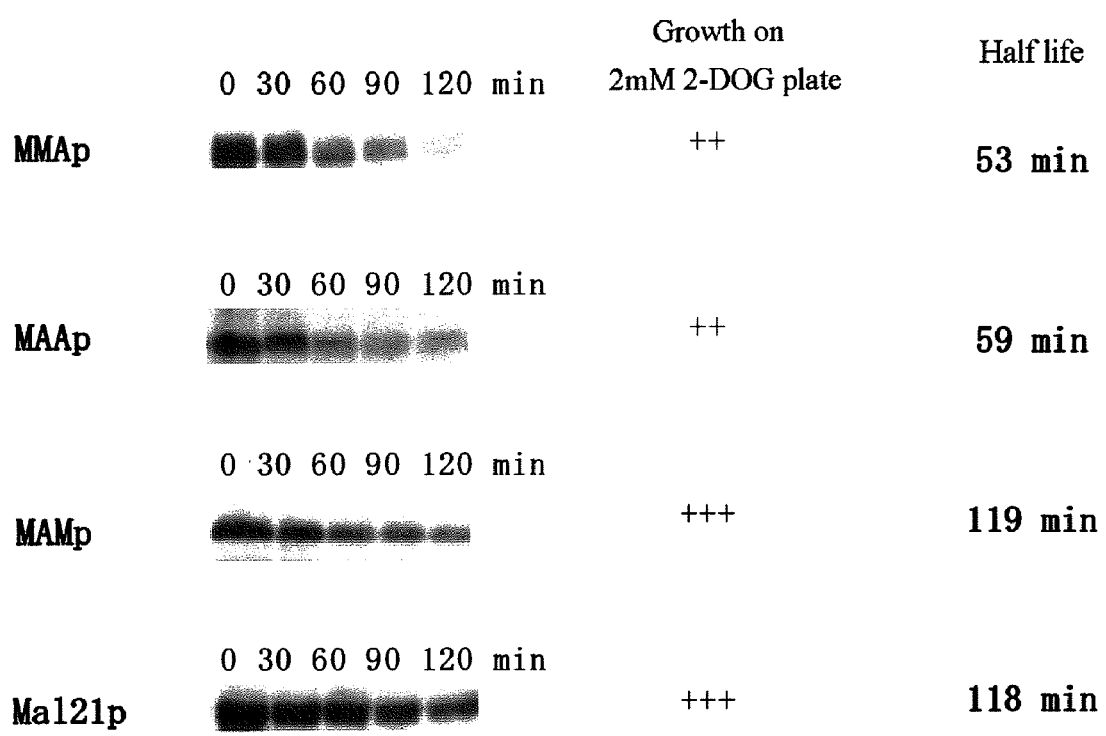
FIG. 10: Glucose-induced degradation rate of hybrid transporter

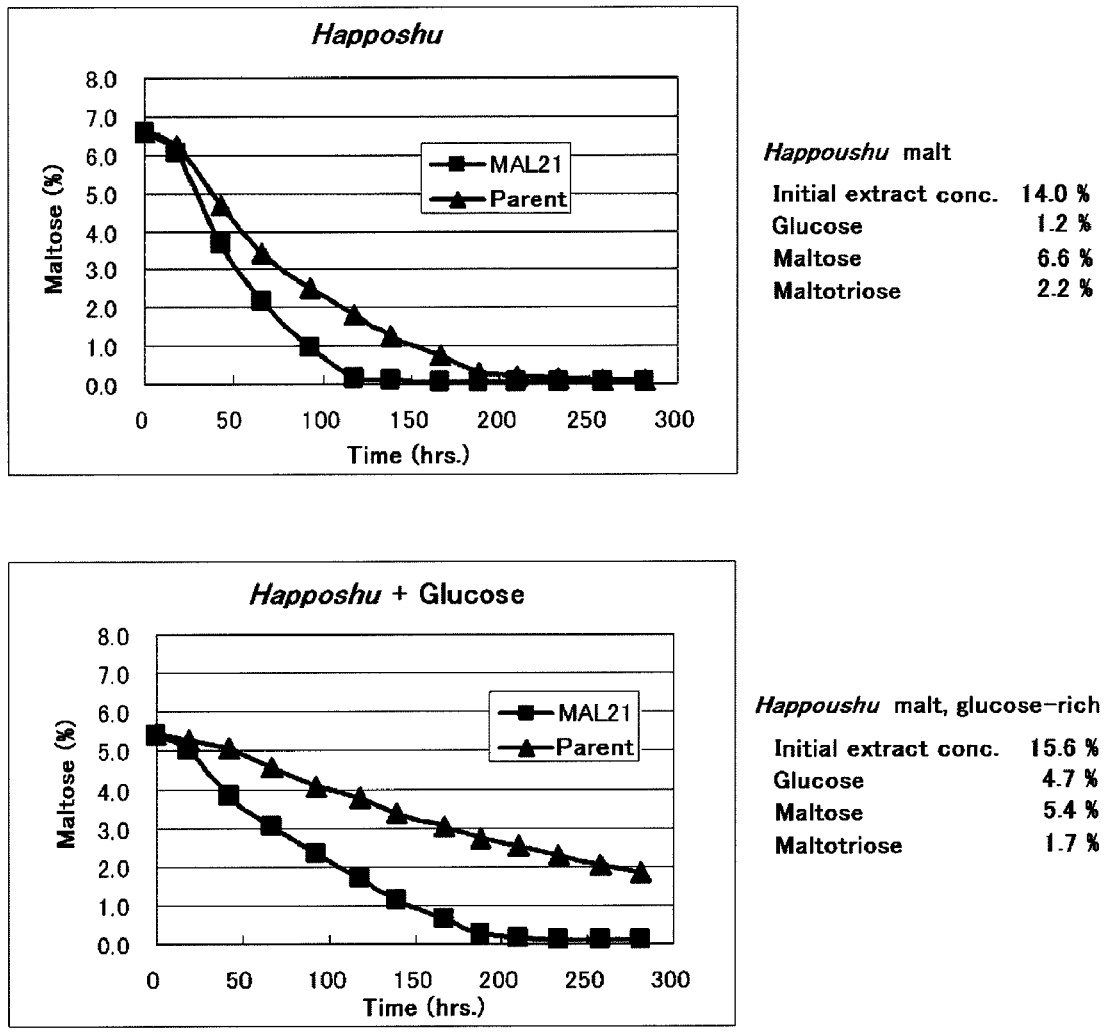
FIG. 11: Fermentation rate of maltose in happoshu (low-malt beer) with bottom-fermenting yeast where the MAL21 gene was highly expressed, or in happoshu

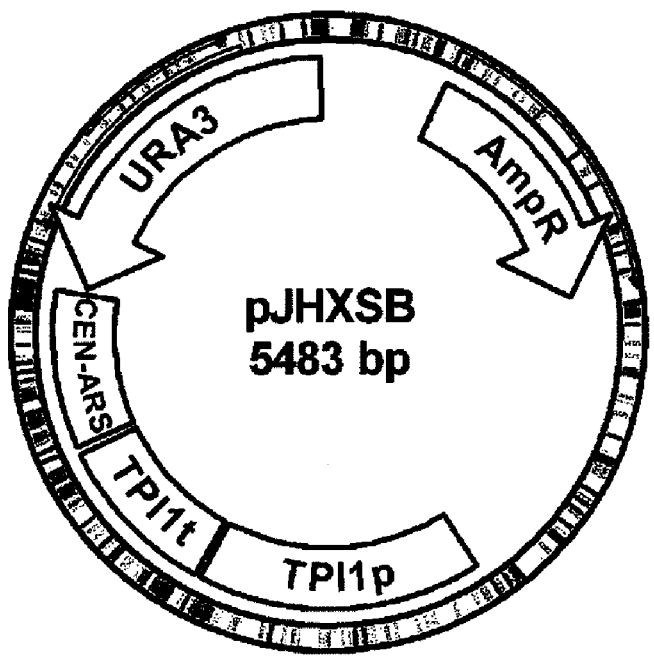
FIG. 12: Plasmid pJHXSB
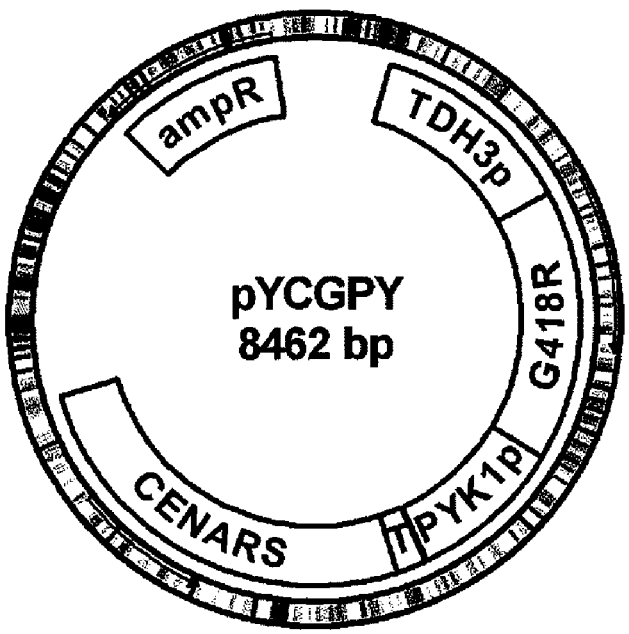
FIG. 13: Plasmid pYCGPY

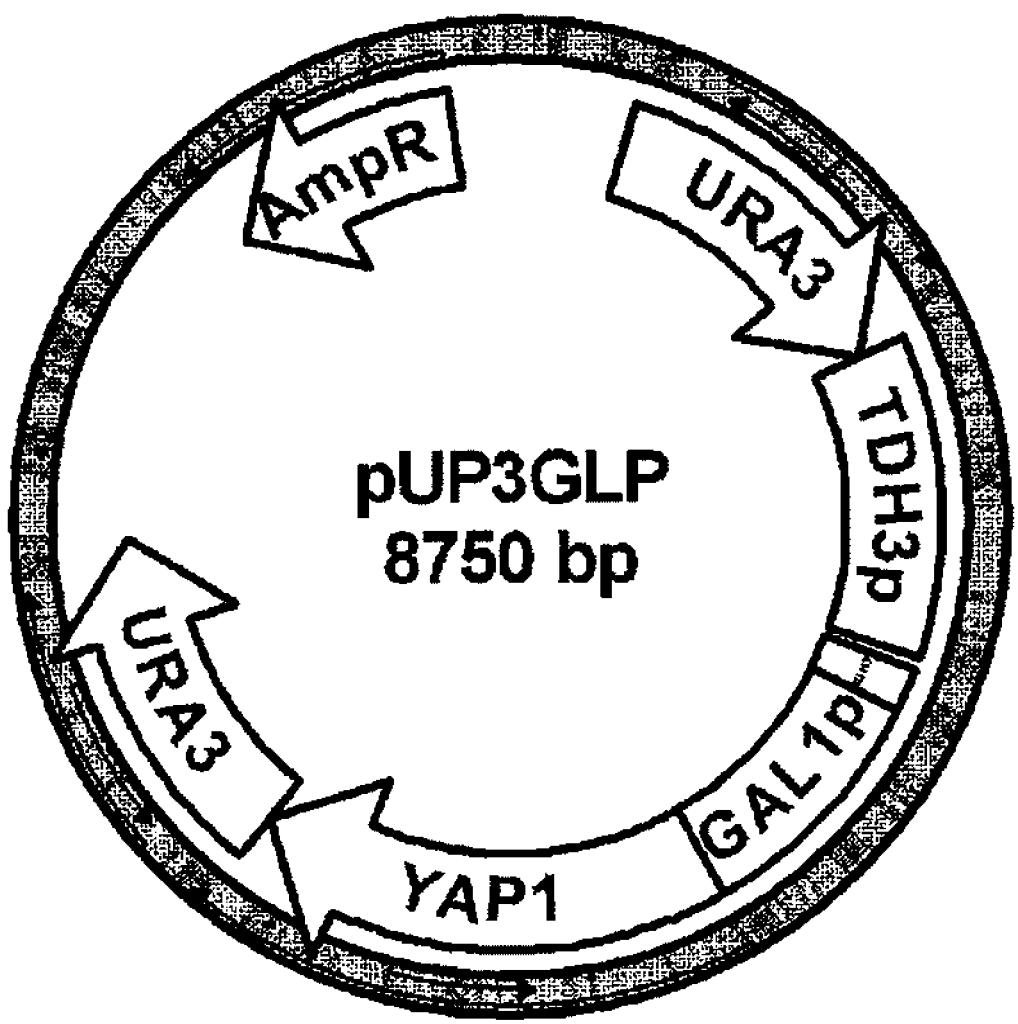
FIG. 14: Plasmid pUP3GLP

US 8,048,667 B2

HYBRID ALPHA-GLUCOSIDE TRANSPORTER

TECHNICAL FIELD

The present invention relates to alpha-glucoside transporters which can promote assimilation of maltose/maltotriose contained in wort, etc., and so on.

BACKGROUND ART

In the production of malt fermented beverages such as beer, happoshu (low-malt beer), whisky, etc., the major three sugars contained in wort prepared by mashing malt, etc. are glucose, maltose and maltotriose. The ratio of these malt-derived sugars can be somewhat varied depending on the mashing process but does not change significantly without addition of enzyme preparations, glycosylated starch, etc., which may be approximately 1:5:1. Among them, glucose is a monosaccharide and preferentially assimilated as a sugar most favored by yeast. Yeast has numerous genes suppressed in the presence of glucose during the transcription process. This control mechanism is called glucose repression. Several transporters required for uptake of maltose or maltotriose into yeast all undergo this repression. It is known that some of these gene products which undergo the gene repression are further inactivated in the presence of glucose after translation. Maltose transporters are also within this type and known to be rapidly degraded in the presence of glucose. The first step of assimilation of maltose or maltotriose is the uptake into yeast cells by these transporters and, when transporters are degraded, assimilation stops. This is the reason why the expression of transporter is called a rate-determining step.

Non-Patent Literature 1: Brondijk, T. H., van der Rest, M. E., Pluim, D., de Vries, Y. de., Stingl, K., Poolman, B., and Konings, W. N. (1998) J. Biol. Chem., 273 (25), 15352-15357

Non-Patent Literature 2: Medintz, I., Wang, X., Hradek, T., and Michels, C. A. (2000) Biochemistry, 39 (15), 4518-4526

Non-Patent Literature 3: Gadura, N., and Michels, C. A. (2006) Curr. Genet., 50 (2), 101-114

Non-Patent Literature 4: Han E. K., Cotty F., Sottas C., Jiang H., Michels C. A., (1995) Mol. Microbiol., 17(6), 1093-107

Accordingly, when a glucose concentration is high, for example, Agt1p in yeast cannot efficiently function upon incubation since its degradation rate is very rapid in the presence of glucose, which is considered as one of the problems.

DISCLOSURE OF INVENTION

Under such circumstances, it has been desired to provide oligosaccharide transporters that can accelerate the fermentation rate by yeast in fermented moromi mash containing oligosaccharides such as maltose, maltotriose, etc.

In particular, the present invention aims at providing alpha-glucoside transporter Agt1p which is less susceptible to glucose-induced inactivation or degradation, because it is expected that if glucose-induced degradation of alpha-glucoside transporter Agt1p after translation could be controlled, maltose/maltotriose could be assimilated into yeast even in the presence of glucose at a high level in a medium.

Based on this concept, the present inventors have made extensive efforts and as a result, succeeded in producing a plurality of hybrid genes of AGT1 known to be susceptible to glucose-induced inactivation/degradation and naturally occurring MAL21 resistant to glucose-induced inactivation/degradation and producing from the resulting hybrid genes a hybrid transporter less susceptible to glucose-induced inactivation/degradation and having the substrate specificity capable of taking up maltotriose like AGT1. The present invention has thus been accomplished.

In other words, the present invention provides a gene encoding a transporter resistant to glucose-induced inactivation/degradation, a transporter protein encoded by the gene, a transformant yeast in which expression of the gene is regulated, a method of producing an alcoholic beverage which comprises using the yeast bearing the expression-regulated gene, and so on. More specifically, the present invention provides the following polynucleotide, a vector comprising the polynucleotide, a transformant yeast into which the vector is introduced, a method of producing an alcoholic beverage which comprises using the vector-introduced transformant yeast, and so on.

(1) A polynucleotide encoding a transporter protein having a resistance to glucose-induced inactivation/degradation, containing a 12-transmembrane domain-coding region consisting of a polynucleotide according to any one of (a) to (d) below, in which the 5' side sequence and/or the 3' side sequence is recombined with a heterologous polynucleotide:

(a) a polynucleotide consisting of a sequence of nucleotides 307 to 1659 in SEQ ID NO: 3 or a sequence of nucleotides 283 to 1641 in SEQ ID NO: 5;

(b) a polynucleotide encoding a sequence of amino acids 103 to 553 in SEQ ID NO: 4 or a sequence of amino acids 95 to 547 in SEQ ID NO: 6;

(c) a polynucleotide encoding an amino acid sequence, wherein deletion, substitution, insertion and/or addition of 1 to 10 amino acids occurs in a sequence of amino acids 103 to 553 in SEQ ID NO: 4 or a sequence of amino acids 95 to 547 in SEQ ID NO: 6; and, (d) a polynucleotide encoding an amino acid sequence having at least 90% identity to a sequence of amino acids 103 to 553 in SEQ ID NO: 4 or a sequence of amino acids 95 to 547 in SEQ ID NO: 6.

(2) The polynucleotide according to (1), wherein a sequence of the heterologous polynucleotide is the 5' side sequence and/or the 3' side sequence to the 12-transmembrane domain in SEQ ID NO: 1.

(3) The polynucleotide according to (1), wherein the recombination position between the 12-transmembrane domain-coding region and the 5' side sequence is within the predicted TMD1 coding region of 12 transmembrane domains, and, the recombination position between the 12-transmembrane domain and the 3' side sequence is within a region from the start position of the predicted TMD12 coding region to within 96 nucleotides toward the 3' side from the end position of the predicted TMD12 coding region and is within a region having at least 80% identity in the corresponding amino acid sequences of SEQ ID NO: 2 and SEQ ID NO: 4.

(4) The polynucleotide according to (1), in which the recombination position between the 12-transmembrane domain-coding region and the 5' side sequence is within a region from nucleotide 175 of SEQ ID NO: 1 or SEQ ID NO: 5 to the end position of predicted TMD1 coding region, and the recombination position between the 12-transmembrane domain-coding region and the 3' side sequence is within a region from the start position of the predicted TMD12 coding region to within 180 nucleotides toward the 3' side from the end position of the predicted TMD12 coding region.

(5) The polynucleotide according to any one of (1) to (4), which comprises a polynucleotide consisting of the nucleotide sequence of SEQ ID NO: 13, 15 or 17.

(6) The polynucleotide according to any one of (1) to (4), which comprises a polynucleotide encoding a protein consisting of the amino acid sequence of SEQ ID NO: 14, 16 or 18.

(7) The polynucleotide according to any one of (1) to (6), which is a DNA.

(8) A protein encoded by the polynucleotide according to any one of (1) to (7).

(9) A vector comprising the polynucleotide according to any one of (1) to (7).

(10) A transformed yeast introduced with the vector according to (9).

(11) The yeast for brewing according to (10), wherein oligosaccharide assimilability is improved by introducing the vector according to (9).

(12) The yeast for brewing according to (11), wherein oligosaccharide assimilability is improved by increasing the expression level of the protein according to (8).

(13) A method of producing an alcoholic beverage, which comprises using the yeast according to any one of (10) to (12).

(14) The method of producing an alcoholic beverage according to (13), wherein the alcoholic beverage to be brewed is a malt beverage.

(15) The method of producing an alcoholic beverage according to (13), wherein the alcoholic beverage to be brewed is wine.

(16) An alcoholic beverage produced by the method according to any one of (13) to (15).

By using the yeast expressing the hybrid transporter gene modified in the present invention, the fermentation rate of moromi mash containing oligosaccharides such as maltose/maltotriose, etc. can be increased. The modified hybrid transporter gene can be introduced into any brewery yeast or laboratory yeast. It is more effective especially for the case where oligosaccharides such as maltose, maltotriose, turanose, trehalose, etc. that the modified transporter can take up are contained in such a crude fermentation liquor as abundantly containing monosaccharides such as glucose, fructose, etc.

BRIEF DESCRIPTION OF DRAWINGS

FIG. 1 shows the nucleotide sequence of MAL21 gene (SEQ ID NO: 33).

FIG. 2 shows the amino acid sequence of Mal21p (SEQ ID NO: 2).

FIG. 3 shows the alignment of the amino acid sequences of Mal21p (SEQ ID NO: 2) and Agt1p (SEQ ID NO: 4).

FIG. 4 shows the alignment of the amino acid sequences of Mal21p (SEQ ID NO: 2) and Mtt1p (SEQ ID NO: 6).

FIG. 5 shows the differences in substrate specificity between Agt1p and Mal21p.

FIG. 6 shows the degradation rates of Agt1p, Mal61p and Mal21p in the presence of glucose.

FIG. 7 schematically shows the sequences of AMMp, AAMp, AMAp, MAAp, MMAp and MAMp.

FIG. 8 shows the substrate specificity of transformed yeasts bearing each of the hybrid transporters AMMp, AAMp, AMAp, MAAp, MMAp and MAMp.

FIG. 9 shows the 2-DOG resistance of transformant yeast bearing each of the hybrid transporter genes AMMp, AAMp, AMAp, MAAp, MMAp and MAMp.

FIG. 10 shows measurement of the degradation rates of MMAp, MAAp and MAMp.

FIG. 11 shows the fermentation rate of maltose in happoshu (low-malt beer) or in happoshu (glucose-rich) wort with bottom-fermenting beer yeast strain where the MAL21 gene was highly expressed.

FIG. 12 shows pJHXSB.

FIG. 13 shows pYCGPY.

FIG. 14 shows pUP3GLP.

BEST MODES FOR CARRYING OUT THE INVENTION

Based on the idea that if glucose-induced inactivation or degradation of a post-translational transporter can be regulated, maltose and maltotriose can be more efficiently assimilated into a yeast in the presence of glucose, the present inventors have made extensive efforts and as a result, found Mal21p from the natural world, which is an α-glucoside transporter less susceptible to degradation, and confirmed that the degradation rate of Mal21p is extremely slow when compared to other transporters.

By highly expressing the hybrid transporter less susceptible to glucose-induced inactivation or degradation which is newly prepared in the present invention, the growth rate was successfully increased actually in a maltose medium. In addition, the assimilation rate of maltose could be increased in beer brewing. Based on this idea and achievements of the research, the present invention has been accomplished.

The genes obtained in the present invention, their nucleotide sequences and the amino acid sequences of the transporter proteins encoded by these genes are given below.

[SEQ ID NO: 1] Nucleotide sequence of MAL21
[SEQ ID NO: 2] Amino acid sequence of Mal21p α-glucoside transporter
[SEQ ID NO: 3] Nucleotide sequence of AGT1
[SEQ ID NO: 4] Amino acid sequence of Agt1p α-glucoside transporter
[SEQ ID NO: 5] Nucleotide sequence of MTT1
[SEQ ID NO: 6] Amino acid sequence of Mtt1p α-glucoside transporter
[SEQ ID NO: 7] Nucleotide sequence of AAM
[SEQ ID NO: 8] Amino acid sequence of AAMp
[SEQ ID NO: 9] Nucleotide sequence of AMA
[SEQ ID NO: 10] Amino acid sequence of AMAp
[SEQ ID NO: 11] Nucleotide sequence of AMM
[SEQ ID NO: 12] Amino acid sequence of AMMp
[SEQ ID NO: 13] Nucleotide sequence of MAA
[SEQ ID NO: 14] Amino acid sequence of MAAp
[SEQ ID NO: 15] Nucleotide sequence of MAM
[SEQ ID NO: 16] Amino acid sequence of MAMp
[SEQ ID NO: 17] Nucleotide sequence of MMA
[SEQ ID NO: 18] Amino acid sequence of MMAp As used herein, the term "α-glucoside transporter" refers to a protein associated with α-glucoside transmembrane transport and such α-glucoside transporters include a maltose transporter, a maltotriose transporter, etc.

1. Polynucleotide of the Invention

First of all, the present invention is directed to the polynucleotide encoding a transporter protein having the resistance to glucose-induced inactivation/degradation, and provides: (a) a polynucleotide comprising a polynucleotide consisting of the sequence of nucleotides 307 to 1659 in SEQ ID NO: 3 or the sequence of nucleotides 283 to 1641 of SEQ ID NO: 5, and (b) a polynucleotide containing a 12-transmembrane domain-coding region consisting of a polynucleotide encoding the sequence of amino acids 103 to 553 of SEQ ID NO: 4 or the sequence of amino acids 95 to 547 in SEQ ID NO: 6, in which the 5' side and/or 3' side sequence is recombined with a heterologous polynucleotide. The polynucleotide may be DNA or RNA.

The 12-transmembrane domain means a span from TMD1 to TMD12 which has 12 transmembrane domains and include the respective transmembrane domains TMD1, TMD2, . . . , TMD12 and the respective intervening sequences. Each number affixed to TMD such as TMD1, TMD12, etc. indicates the number of transmembrane domains counted from the N terminus of amino acid sequence. Accordingly, the 12-transmembrane domain-coding region refers to a nucleotide sequence encoding the amino acid sequence extending from TMD1 to TMD12, and the TMD1 coding region refers to a nucleotide sequence encoding the amino acid sequence of TMD1.

The present invention relates to a recombinant transporter protein in which the N-terminal and/or C-terminal sequence of alpha-glucoside transporter protein having 12-transmembrane domain is recombined with the N-terminal and/or C-terminal sequence of other transporter protein having 12-transmembrane domain, or a polynucleotide encoding the recombinant transporter protein. Therefore, the term "heterologous polynucleotide" as used herein refers to a polynucleotide that encodes a transporter protein different from a transporter protein prior to the recombination. In the case of recombining with the heterologous polynucleotide, it is preferred to confirm the alignment of nucleotide sequences and/or amino acid sequences between the target polynucleotide and the heterologous polynucleotide to be recombined, whereby the recombination can be made between the corresponding regions.

The 5' side sequence and/or the 3' side sequence refers to a sequence in the vicinity of a certain gene or DNA sequence, namely, a sequence present on the 5' side and/or the 3' side. For example, the 5' side sequence to the 12-transmembrane domain-coding region contains a sequence to initiate translation of the region encoding a protein having the 12-transmembrane domain at the center, and the 3' side sequence to the 12-transmembrane domain-coding region contains a sequence to terminate translation of the region encoding a protein having the 12-transmembrane domain at the center. In the present invention, the 5' side sequence and the 3' side sequence refer to the 5' side sequence and the 3' side sequence between which the 12-transmembrane domain are inserted. The recombination position on the 5' side may be, for example, in the region within TMD1 or upstream of the 5' side from the start position for TMD1.

The polynucleotide preferred in the present invention includes a polynucleotide encoding the transporter protein having the resistance to glucose-induced inactivation/degradation in which the 5' side and/or 3' side sequence to the 12 transmembrane domain-coding region consisting of a polynucleotide consisting of the sequence of nucleotides 307 to 1659 in SEQ ID NO: 3 or a sequence of nucleotides 283 to 1641 in SEQ ID NO: 5 or a polynucleotide encoding the sequence of amino acids 103 to 553 in SEQ ID NO: 4, or the sequence of amino acids 95 to 547 in SEQ ID NO: 6 is recombined with the 5' side and/or 3' side sequence to the 12 transmembrane domain-coding region of SEQ ID NO: 1.

The polynucleotide intended in the present invention is not limited to the polynucleotides encoding the proteins having the sequences described above but includes other polynucleotides encoding proteins functionally equivalent to the proteins having the above sequences. The functionally equivalent proteins include, for example, (c) a transporter protein comprising an amino acid sequence in which 1 to 10 (preferably 1 to 9, 1 to 8, 1 to 7, 1 to 6, 1 to 5, 1 to 4, 1 to 3, 1 to 2 or 1) amino acids are deleted, substituted, inserted and/or added in the sequence of amino acids 103 to 553 of SEQ ID NO: 4 or in the sequence of amino acids 95 to 547 in SEQ ID NO: 6, and having the resistance to glucose-induced inactivation/degradation.

Such a protein includes a transporter protein comprising an amino acid sequence in which, for example, 1 to 10, 1 to 9, 1 to 8, 1 to 7, 1 to 6 (1 to several), 1 to 5, 1 to 4, 1 to 3, 1 to 2 or 1 amino acid residue is deleted, substituted, inserted and/or added in the sequence of amino acids 103 to 553 of SEQ ID NO: 4 or in the sequence of amino acids 95 to 547 in SEQ ID NO: 6, and having the resistance to glucose-induced inactivation/degradation. Generally it is more preferred as the number of the deletion, substitution, insertion and/or addition of the amino acid residues above becomes smaller.

Such proteins include transporter proteins having (d) an amino acid sequence having an identity of at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8% and at least about 99.9%, with the sequence of amino acids 103 to 553 in SEQ ID NO: 4 or with the sequence of amino acids 95 to 547 in SEQ ID NO: 6, and having the resistance to glucose-induced inactivation/degradation. In general, the numerical value of the homology described above is more preferable as the number becomes larger.

<Evaluation of the Resistance to Glucose-Induced Inactivation/Degradation>

According to the present invention, the resistance to glucose-induced inactivation/degradation can be evaluated, for example, by the following procedures. First, it is confirmed that a strain expressing each transporter protein is able to grow in a 0 to 2 mM 2-deoxyglucose-containing maltose, etc.—supplemented minimum medium (6.7 g/L of yeast nitrogen base w/o amino acids, 20 g/L of maltose, etc.; also containing the required nutrients if the transformant is auxotrophic) or in a 0 to 2 mM 2-deoxyglucose-containing maltose, etc.—supplemented synthetic complete medium (SCM) (6.7 g/L of yeast nitrogen base w/o amino acids, 20 g/L of maltose, 20 mg/ml of adenine sulfate, 20 mg/ml of uracil, 20 mg/ml of L-tryptophan, 20 mg/ml of L-histidine hydrochloride, 20 mg/ml of L-arginine hydrochloride, 20 mg/ml of L-methionine, 30 mg/ml of L-tyrosine, 30 mg/ml of L-leucine, 30 mg/ml of L-isoleucine, 30 mg/ml of L-lysine hydrochloride, 50 mg/ml of L-phenylalanine, 100 mg/ml of L-glutamic acid, 100 mg/ml of L-aspartic acid, 150 mg/ml of L-valine, 200 mg/ml of L-threonine and 400 mg/ml of L-serine), to select the strain in which the transporter retains the maltose uptake activity in yeasts even where the signal of glucose-induced inactivation/degradation generates. Next, this strain is inoculated into YPD (10 g/L of yeast extract, 20 g/L of polypeptone and 20 g/L of glucose) followed by shaking the culture at 30° C. overnight. The culture broth is inoculated into a YPM medium (10 g/L of yeast extract, 20 g/L of polypeptone and 5 g/L of maltose) to reach OD660=1.0 followed by shaking the culture at 30° C. for 2.5 hours. The cells are then collected. The 60 OD660 units of cells are measured and suspended in 30 ml of a medium for degradation rate measurement (1.7 g/L of yeast nitrogen base w/o amino acids and ammonia, 20 g/L of glucose and 25 µg/L of cycloheximide) preincubated at 30° C., followed by incubation at 30° C. The cell suspension is monitored by means of 5 ml sampling at an appropriate time (0, 10, 20, 30 and 40 minutes or 0, 30, 60, 90 and 120 minutes). After the suspension is centrifuged immediately thereafter, the supernatant is discarded and the cells are frozen using an ethanol-dry ice. The transporter protein is detected from the frozen cells in a conventional manner and the intensity of the protein band is measured to determine the half life from its diminution rate. The transporter protein preferred in the present invention has the half life of, for example, 2 times or more, 3 times or more, 4 times or more, 5 times or more, 6 times or more or 8 times or more, than that of Agt1p.

<Guidelines of Transmembrane Domains of Protein>

In the present invention, "the sequence of nucleotides 307 to 1659 in SEQ ID NO: 3 or the sequence of nucleotides 283 to 1641 in SEQ ID NO: 5" defined in (a) above and "the sequence of amino acids 103 to 553 in SEQ ID NO: 4 or the sequence of amino acids 95 to 547 in SEQ ID NO: 6" defined in (b) above is the region predicted as the 12-transmembrane domain of Agt1p or Mtt1p in yeast. The transmembrane domains of these proteins can be predicted using the topology prediction program TopPred2 at the Stockholm University Theoretical Chemistry Protein Prediction Server (bioweb.pasteur.fr/seqanal/interfaces/toppred.html) or the transmembrane regions detection program TMPRED: Transmembrane Regions Detection at EMBnet (EMBnet ch.embnet.org/index.html) (accessed Aug. 29, 2008), or others. The predicted transmembrane domains of Mal61p are described in Cheng, Q. and Michels, C. A. (1989) Genetics 123(3), 477-484. Herein, TopPred2 at the Stockholm University Theoretical Chemistry Protein Prediction Server (bioweb.pasteur.fr/seqanal/interfaces/toppred.html) was used to predict TMD1 to 12 below.

The alignments of the amino acid sequences of Mal21p and Agt1p and the alignments of the amino acid sequences of Mal21p and Mtt1p are shown in FIGS. 3 and 4, respectively. In each of the figures, information including identical amino acids (light gray), amino acids with homology (dark gray), amino acids without homology, gaps (–), etc. is shown.

The present invention also provides the polynucleotide encoding a transporter protein having the resistance to glucose-induced inactivation/degradation, in which the recombination position between the 12-transmembrane domain-coding region and the 5' side sequence is within the predicted TMD1 coding region, the recombination position between the 12-transmembrane domain-coding region and the 3' side sequence is within a region from the start position of the predicted TMD12 coding region to within 96 nucleotides toward the 3' side from the end position of the predicted TMD12 coding region and is within a region having at least 80% identity with the corresponding amino acid sequences of SEQ ID NO: 2 and SEQ ID NO: 4.

Referring to FIG. 3 for the "predicted TMD1" described above, the amino acids 95 to 115 in Mal21p (SEQ ID NO: 2) and the amino acids 103 to 123 in Agt1p (SEQ ID NO: 4) are shown as the predicted positions (in FIG. 3, the predicted position for TMD1 indicates the predicted position for Agt1p). Accordingly, the nucleotide sequences encoding the respective amino acid sequences are the region from nucleotides 283 to 345 in MAL21 (SEQ ID NO: 1) and the region from nucleotides 307 to 369 in AGT1 (SEQ ID NO: 3). Likewise, referring to FIG. 3 for the "predicted TMD12" described above, the amino acids in the region from amino acids 526 to 546 in Mal21p (SEQ ID NO: 2) and the amino acids in the region from amino acids 533 to 553 in Agt1p (SEQ ID NO: 4) are shown as the predicted positions (in FIG. 3, the predicted position of TMD12 indicates the predicted position for Agt1p). Thus, the respective predicted TMD12 coding regions are the region from nucleotides 1576 to 1638 in MAL21 (SEQ ID NO: 1) and the region from nucleotides 1597 to 1659 in AGT1 (SEQ ID NO: 3). Therefore, the term "region from the start position of the predicted TMD12 coding region to within 96 nucleotides from the end position of the predicted TMD12 coding region" refers to a region from nucleotides 1576 to 1734 in MAL21 (SEQ ID NO: 1) and the region from nucleotides 1597 to 1755 in AGT1 (SEQ ID NO: 3). The "region within 96 nucleotides from the end position of the predicted TMD12 coding region" described above is preferably a region within 96 nucleotides, more preferably within 81 nucleotides and most preferably within 72 nucleotides, from the end position of the predicted TMD12 coding region. One example for each of the corresponding sequence locations is shown in TABLE 1 below. In this regard, however, these numerical values may vary in several orders, depending upon the prediction programs described above.

TABLE 1

| Name | SEQ ID NO: | Predicted TMD1 | 5'-Side Recombination Region Predicted TMD12 | 3'-Side Recombination Region +32aa |
|------|------------|----------------|----------------------------------------------|-------------------------------------|
| MAL21 | 1 (full length: 1842 nucleotides) | 283-345 | 1576-1638 | 1639-1734 |
| Mal21p | 2 (full length: 614 amino acids) | 95-115 | 526-546 | 547-578 |
| AGT1 | 3 (full length: 1848 nucleotides) | 307-369 | 1597-1659 | 1660-1755 |
| Agt1p | 4 (full length: 616 amino acids) | 103-123 | 533-553 | 554-585 |

The present invention further provides the polynucleotide encoding a transporter protein having the resistance to glucose-induced inactivation/degradation, in which the recombination position between the 12-transmembrane domain-coding region and the 5' side sequence is within the region from nucleotide 175 of SEQ ID NO: 1 to the end position of the predicted TMD1 coding region of the 12-transmembrane domain, and the recombination position between the 12-transmembrane domain and the 3' side sequence is within a region from the start position of the predicted TMD12 coding region to nucleotide 180 from the end position of the predicted TMD12 coding region.

Referring to FIG. 4 for the "predicted TMD1" described above, amino acids 95 to 115 in Mal21p (SEQ ID NO: 2) and Mtt1p (SEQ ID NO: 6) are shown as the predicted positions (i.e., no gap). Accordingly, the nucleotide sequence corresponding to the "predicted TMD1 coding region" is the region from nucleotides 283 to 345 in MAL21 (SEQ ID NO: 1) and MTT1 (SEQ ID NO: 5). Thus, the "region from nucleotide 175 of SEQ ID NO: 1 or SEQ ID NO: 5 to the end position of the predicted TMD1 coding region" refers to nucleotides 175 to 345 in SEQ ID NO: 1 or SEQ ID NO: 5. Since the two amino acid sequences within this span completely match in the region from nucleotide 175 to the end position of the predicted TMD1 coding region, any position within this span can be selected as a recombination position (see FIG. 4).

Similarly in the "predicted TMD12," the amino acids in the region from 526 to 546 in Mal21p (SEQ ID NO: 2) and the amino acids in the region from 527 to 547 in Mtt1p (SEQ ID NO: 6) are shown as the predicted positions. Accordingly, the "region from the start position of the predicted TMD12 coding region to within 180 nucleotides from the end position of the predicted TMD12 coding region" refers to a region from 1576 to 1818 in MAL21 (SEQ ID NO: 1) and a region from 1579 to 1821 in MTT1 (SEQ ID NO: 5), in terms of nucleotide sequence. In the region within 180 nucleotides from the end position of the predicted TMD12 coding region, the two amino acid sequences completely match within this span and any position within this span can be selected as a recombination position (see FIG. 4). For each of the corresponding sequence locations, reference is made to TABLE 2 below. In this regard, however, these numerical values may vary in several orders, depending upon the prediction programs described above.

TABLE 2

| Name | SEQ ID NO: | 5'-Side Recombination Region | | 3'-Side Recombination Region | |
|---|---|---|---|---|---|
| | | (−36aa) | Predicted TMD1 | Predicted TMD12 | (+60aa) |
| MAL21 | 1 (full length: 1842 nucleotides) | 175-282 | 283-345 | 1576-1638 | 1639-1818 |
| Mal21p | 2 (full length: 614 amino acids) | 59-94 | 95-115 | 526-546 | 547-606 |
| MTT1 | 5 (full length: 1845 nucleotides) | 175-282 | 283-345 | 1579-1641 | 1642-1821 |
| Mtt1p | 6 (full length: 615 amino acids) | 59-94 | 95-115 | 527-547 | 548-607 |

The present invention further encompasses polynucleotides comprising a polynucleotide consisting of the nucleotide sequence of SEQ ID NO: 13, 15 or 17, or polynucleotides comprising a polynucleotide encoding the protein consisting of the amino acid sequence of SEQ ID NO: 14, 16 or 18. The present invention also encompasses polynucleotides comprising a polynucleotide which hybridizes, under stringent conditions, to the polynucleotide described in (1) through (4) above or a polynucleotide consisting of a nucleotide sequence complementary to the nucleotide sequence of SEQ ID NO: 13, 15 or 17 and encodes a transporter protein having the resistance to glucose-induced inactivation/degradation.

The polynucleotides which are preferred in the present invention are the polynucleotides defined in (1) through (4) above, the polynucleotides comprising a polynucleotide encoding the protein consisting of the amino acid sequence of SEQ ID NO: 14, 16 or 18, and the polynucleotide comprising the polynucleotide consisting of the nucleotide sequence of SEQ ID NO: 13, 15 or 17, more preferably the polynucleotide specified by SEQ ID NO: 13, 15 or 17.

As used herein, the term "polynucleotide (DNA) which hybridizes under stringent conditions" refers to, for example, a DNA consisting of a nucleotide sequence complementary to the nucleotide sequence of SEQ ID NO: 1 or 3, or a DNA obtained by the colony hybridization technique, the plaque hybridization technique, the Southern hybridization technique or the like, using as a probe all or a part of DNA encoding the amino acid sequence of SEQ ID NO: 2 or 4. For the hybridization, there may be used methods described in, for example, Molecular Cloning, 3rd Ed., Current Protocols in Molecular Biology, John Wiley & Sons 1987-1997, etc.

As used herein, the term "stringent conditions" may be any of low stringent conditions, medium stringent conditions and high stringent conditions. The term "low stringent conditions" refers to conditions of, e.g., 5×SSC, 5×Denhardt's solution, 0.5% SDS, 50% formamide and 32° C. The term "medium stringent conditions" refers to conditions of, e.g., 5×SSC, 5×Denhardt's solution, 0.5% SDS, 50% formamide and 42° C. The term "high stringent conditions" refers to conditions of, e.g., 5×SSC, 5×Denhardt's solution, 0.5% SDS, 50% formamide and 50° C. It can be expected under these conditions that DNAs having a higher homology can be efficiently obtained as the temperature becomes higher. However, there are several factors that might affect the stringency of hybridization to be considered and such factors include temperature, probe concentration, probe length, ionic strength, time, salt concentration, etc. Those skilled in the art can suitably choose these factors to achieve the same stringencies.

When a commercially available kit is used for hybridization, for example, Alkphos Direct Labeling Reagents (manufactured by Amersham Pharmacia) can be used. In this case, according to the attached protocol, after incubation with a labeled probe overnight, the membrane is washed with a primary wash buffer containing 0.1% (w/v) SDS at 55° C., whereby the hybridized DNA can be detected.

Other DNAs that can be hybridized include DNAs having about 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher or 99.9% or higher identity with the DNA encoding the amino acid sequence of SEQ ID NO: 2 or 8 as calculated by a homology search software such as FASTA, BLAST, etc. using default parameters.

Identity between amino acid sequences or nucleotide sequences can be determined using algorithm BLAST by Karlin and Altschul (Proc. Natl. Acad. Sci. USA, 87: 2264-2268, 1990; Proc. Natl. Acad. Sci. USA, 90: 5873, 1993). Programs called BLASTN and BLASTX based on BLAST algorithm have been developed (Altschul, S. F., et al., J. Mol. Biol., 215: 403, 1990). When a nucleotide sequence is analyzed using BLASTN, the parameters are set to, for example, score=100 and word length=12. When an amino acid sequence is analyzed using BLASTX, the parameters are set to, for example, score=50 and word length=3. When BLAST and Gapped BLAST programs are used, default parameters for each of the programs are employed.

2. Protein of the Present Invention

The present invention also provides proteins encoded by any of the polynucleotides (1) to (6) described above. The proteins preferred in the present invention include transporter proteins consisting of the amino acid sequence of SEQ ID NO: 14, 16 or 18, wherein 1 to 10 (preferably 1 to 9, 1 to 8, 1 to 7, 1 to 6, 1 to 5, 1 to 4, 1 to 3, 1 to 2, or 1) amino acids are deleted, substituted, inserted and/or added, and having the resistance to glucose-induced inactivation/degradation. Such proteins include transporter proteins consisting of the amino acid sequence of SEQ ID NO: 14, 16 or 18, wherein the number of amino acid residues as described above is deleted, substituted, inserted and/or added, and having the resistance to glucose-induced inactivation/degradation. Also, such proteins include transporter proteins having the above-described homology to the amino acid sequence of SEQ ID NO: 14, 16 or 18, and having the resistance to glucose-induced inactivation/degradation. These proteins can be obtained by site-directed mutagenesis described, for example, in MOLECULAR CLOMNG 3rd ed., CURRENT PROTOCOLS IN MOLECULAR BIOLOGY, Nuc. Acids. Res., 10: 6487 (1982), Proc. Natl. Acad Sci. USA, 79: 6409 (1982), Gene 34: 315 (1985), Nuc. Acids. Res., 13: 4431 (1985), Proc. Natl. Acad. Sci. USA, 82: 488 (1985), etc.

The term deletion, substitution, insertion and/or addition of 1 to 10 (preferably 1 to 9, 1 to 8, 1 to 7, 1 to 6, 1 to 5, 1 to 4, 1 to 3, 1 to 2, or 1) amino acid residues in the amino acid sequence of the protein in accordance with the polynucleotide of the present invention is used to means that 1 to 10, 1 to 9, 1 to 8, 1 to 7, 1 to 6, 1 to 5, 1 to 4, 1 to 3, 1 to 2, or 1 amino acid residue is deleted, substituted, inserted and/or added at optional positions of 1 to 10, 1 to 9, 1 to 8, 1 to 7, 1 to 6, 1 to 5, 1 to 4, 1 to 3, 1 to 2, or 1 amino acid residue in the same sequence. Two or more types of the deletion, substitution, insertion and/or addition may occur concurrently.

Hereinafter, examples of mutually substitutable amino acid residues are shown. Amino acid residues in the same group are mutually substitutable. Group A: leucine, isoleucine, norleucine, valine, norvaline, alanine, 2-aminobutanoic acid, methionine, o-methylserine, t-butylglycine, t-butylalanine and cyclohexylalanine; Group B: aspartic acid, glutamic acid, isoaspartic acid, isoglutamic acid, 2-aminoadipic acid and 2-aminosuberic acid; Group C: asparagine and glutamine; Group D: lysine, arginine, ornithine, 2,4-diaminobutanoic acid and 2,3-diaminopropionic acid; Group E: proline, 3-hydroxyproline and 4-hydroxyproline; Group F: serine, threonine and homoserine; and Group G: phenylalanine and tyrosine.

The protein of the present invention can also be produced by chemical synthesis methods such as Fmoc method (fluorenylmethyloxycarbonyl method), tBoc method (t-butyloxycarbonyl method) and the like. In addition, peptide synthesizers available from, for example, Advanced ChemTech, Perkin Elmer, Pharmacia, Protein Technology Instrument, Synthecell-Vega, PerSeptive, Shimadzu Corp., etc. can also be used for chemical synthesis.

3. Vector of the Present Invention and Yeast Transformed with the Vector

Next, the present invention provides a vector comprising the polynucleotide described above. The vector of the present invention preferably includes the polynucleotide (DNA) described in any one of (1) to (4) above, a polynucleotide consisting of the nucleotide sequence of SEQ ID NO: 13, 15 or 17, or a polynucleotide encoding a protein consisting of the nucleotide sequence of SEQ ID NO: 14, 16 or 18. Generally, the vector of the present invention is so constructed as to contain an expression cassette comprising as the constituent elements (x) a promoter that can be transcribed in a yeast cell; (y) the polynucleotide described in any one described above that is linked to the promoter in a sense or antisense direction; and (z) a signal that functions in the yeast with respect to transcription termination and polyadenylation of RNA molecule. When it is intended to express the protein of the present invention described above at a high level, it is preferred to introduce these polynucleotides in a sense direction to the promoter in order to promote the expression of the polynucleotide (DNA) described in any one of (a) through (i) above.

As the vector used to introduce into the yeast, any of a multicopy type (YEp type), a single copy type (YCp type), or a chromosome integration type (YIp type) may be available. For example, YEp24 (J. R. Broach et al., Experimental Manipulation of Gene Expression, Academic Press, New York, 83, 1983) is known as a YEp type vector, YCp50 (M. D. Rose et al., Gene, 60, 237, 1987) is known as a YCp type vector, and YIp5 (K. Struhl, et al., Proc. Natl. Acad. Sci. USA, 76, 1035, 1979) is known as a YIp type vector, all of which are readily available. In addition, a chromosome integrative vector such as pUP3GLP (Omura, F., et al., FEMS Microbiol. Lett., 194, 207, 2001) (FIG. 14) or pJHIXSB, or a single-copy replicating plasmid such as pYCGPY (Kodama, Y., et al., Appl. Environ. Microbiol., 67, 3455, 2001) (FIG. 13), pJHXSB (FIG. 12), etc. can also be used.

Promoters/terminators for regulating gene expression in a yeast may be in any combination as long as they function in a brewery yeast and are not affected by the concentration of constituents such as sugars, amino acids, etc., in moromi mash. For example, a promoter for glyceraldehyde-3-phosphate dehydrogenase gene (TDH3), a promoter for 3-phosphoglycerate kinase gene (PGK1), etc. can be used. These genes were already cloned and described in detail, for example, in M. F. Tuite et al., EMBO J., 1, 603 (1982), which are readily available by known methods. In expression vectors, promoters to be used can be effectively replaced to those having a suitable transcription activity depending on the sugar composition or sugar concentration of fermented moromi mash, the combination of a plurality of transporters, etc.

As a selection marker for transformation, auxotrophic markers cannot be used for the brewery yeasts; therefore, a geneticin-resistant gene (G418r), a copper-resistant gene (CUP1) (Marin et al., Proc. Natl. Acad. Sci. USA, 81, 337 1984), a cerulenin-resistant gene (fas2m, PDR4) (Junji Inokoshi et al., Biochemistry, 64, 660, 1992; and Hussain, et al., Gene, 101: 149, 1991, respectively), or others may be used as such markers. The vector constructed as described above is introduced into a host yeast. The host yeast includes any yeast which can be used for brewing, e.g., brewery yeasts for beer, wine, sake, etc. Specifically, yeasts belonging to the *Saccharomyces* genus are used. According to the present invention, beer yeasts, for example, *Saccharomyces pastorianus* W34/70, etc., *Saccharomyces carlsbergensis* NCYC453, NCYC456, etc., or *Saccharomyces cerevisiae* NBRC 1951, NBRC 1952, NBRC 1953, NBRC 1954, etc., can be used. In addition, whisky yeasts such as *Saccharomyces cerevisiae* NCYC90, etc., wine yeasts such as Kyokai Wine Yeast Nos. 1, 3 and 4, etc. from the Brewing Society of Japan, sake yeasts such as Kyokai Sake Yeast Nos. 7 and 9, etc. from the Brewing Society of Japan can also be used but are not limited thereto. In the present invention, lager brewing yeasts such as *Saccharomyces pastorianus* is preferably used.

The chromosomal DNA used to prepare each transporter gene described herein is not limited to the strains such as *Saccharomyces cerevisiae* ATCC 20598, ATCC 96955, etc., but may be prepared from any yeast strains so long as it belongs to *Saccharomyces cerevisiae* bearing each gene Known methods conventionally used are available for yeast transformation. For example, the following methods can be used, including, but not limited to, the electroporation method described in Meth. Enzym., 194, 182 (1990), the spheroplast method described in Proc. Natl. Acad. Sci. USA, 75, 1929 (1978), the lithium acetate method described in J. Bacteriology, 153, 163 (1983), the methods described in Proc. Natl. Acad. Sci. USA, 75, 1929 (1978), Methods in Yeast Genetics, 2000 Edition: A Cold Spring Harbor Laboratory Course Manual, etc.

The transformant can be selected on a uracil-free agar medium by incorporating a gene complementing the auxotrophy of a host such as URA3 into an expression plasmid. Alternatively by incorporating into an expression plasmid a drug resistant gene, e.g., YAP1 that is a gene resistant to cycloheximide, or G418R that is a gene resistant to geneticin, the transformants can be selected on an agar medium supplemented with cycloheximide (e.g., 0.3 µg/ml) or geneticin (e.g., 300 µg/ml).

More specifically, a host yeast is cultured in a standard yeast nutrient medium (such as the YEPD medium described in Genetic Engineering, vol. 1, Plenum Press, New York, 117 (1979), etc.) such that the OD at 600 nm value is between 1 and 6. The cultured cells are then collected by centrifugation, washed, and pre-treated with alkali metal ions, preferably lithium ions, at a concentration of about 1 to 2 M. The cells are allowed to stand at about 30° C. for about 60 minutes, and then allowed to stand together with the DNA to be introduced (about 1 to 20 µg) at about 30° C. for about 60 minutes. Polyethylene glycol, preferably a polyethylene glycol of about 4,000 daltons, is added to reach the final concentration of about 20% to 50%. After the cells are allowed to stand at about 30° C. for about 30 minutes, the cells are heat-treated at about 42° C. for about 5 minutes. Preferably, the cell suspension is washed with a standard yeast nutrient medium, inoculated into a predetermined amount of a fresh standard yeast nutrient medium, and then allowed to stand at about 30° C. for about 60 minutes. Thereafter, the resulting culture is spreaded on a standard agar medium supplemented with an antibiotic or the like to be used as a selection marker to obtain transformants.

Other general cloning techniques can be found in, for example, Molecular Cloning, 3rd edition, Methods in Yeast Genetics, A Laboratory Manual (Cold Spring Harbor Laboratory Press; Cold Spring Harbor, N.Y.). etc.

4. Method of Producing the Alcoholic Beverages of the Present Invention and the Alcoholic Beverages Produced by the Method By introducing the vector of the present invention described above into a yeast suitable for brewing the targeted alcoholic beverages and using the resulting yeast, alcoholic beverages having a characteristic amino acid composition can be produced. The alcoholic beverages targeted include, but not limited to, beer, wine, whisky, sake, etc.

In producing these alcoholic beverages, known methods can be used except that the brewery yeast obtained in the present invention is used in place of the parent strain. Accordingly, raw materials, manufacturing facilities, manufacturing control, etc. can be exactly the same as those according to conventional methods and there is no increase in costs for producing alcoholic beverages whose fermentation period is shortened. In other words, the alcoholic beverages can be produced using the existing facilities, without increasing costs.

5. Method for Evaluation of Yeast

An expression vector comprising the polynucleotide produced in the present invention is constructed and introduced into a yeast in a conventional manner. The resulting transformant is first cultured in a maltose/maltotriose medium supplemented with 2-deoxyglucose to select a yeast containing a glucose-induced inactivation-resistant transporter protein using its growth level as an indicator. Next, the yeast is cultured in an oligosaccharide medium (e.g., a maltose/maltotriose medium). During the incubation, the resistance to glucose-induced inactivation/degradation of the transporter contained in the yeast, the oligosaccharide assimilability, growth rate and wort fermentation rate of the yeast, etc. are measured, whereby aptitude of the yeast can be evaluated. The resistance to glucose-induced inactivation/degradation, oligosaccharide assimilability, growth rate and wort fermentation rate, etc. can be evaluated by the methods used in EXAMPLES later described.

EXAMPLES

Hereinafter, the present invention will be described in more detail by referring to EXAMPLES but it should be noted that the present invention is not deemed to be limited thereto.

Testing Methods:

Test items and testing methods used in EXAMPLES are shown below. The testing methods in EXAMPLES were performed in accordance with the methods below, unless otherwise indicated.

<Obtaining of the MAL21 and AGT1 Genes>

The AGT1 gene of *Saccharomyces cerevisiae* is already cloned and its nucleotide sequence is reported. AGT1 (SEQ ID NO: 3) described herein was obtained from the *Saccharomyces* Genome Database (Accession No. YGR289C). The AGT1 gene was obtained by amplifying by PCR based on the sequence information using as a template the chromosomal DNA, which was prepared from a yeast of *Saccharomyces cerevisiae* bearing the AGT1 gene, and then isolating the same.

Also, MAL21 was known to be encoded by chromosome III, but its DNA sequence was unknown. However, as MAL31 encoded by chromosome II and MAL61 encoded by chromosome VIII had the identity of 99% or more, it was expected that MAL21 would also have a considerably high identity.

Actually the inventors designed primers (5'AGAGCTCAGCATATAAAGAGACA 3' (SEQ ID NO: 19) and 5'TGGATCCGTATCTACCTACTGG 3' (SEQ ID NO: 20)) based on the DNA sequence of MAL61 acquired from GenBank (Accession No. X17391). Using as a template chromosomal DNA of the yeast bearing the MAL21 gene but no other α-glucoside transporter genes, MAL21 could be obtained by PCR (its nucleotide sequence is shown by SEQ ID NO: 1 and the amino acid sequence is shown by SEQ ID NO: 2). AGT1 was obtained using the primers (5'TGAGCTCACATAGAAGAACATCAAA 3' (SEQ ID NO: 21) and 5'ATGGATCCATATGAAAAATATCATT 3' (SEQ ID NO: 22)). Specifically, AGT1 was obtained by PCR from *Saccharomyces cerevisiae* S288C (ATCC 204508 (Rose, M. D., Winston, F. and Hieter, P. (1990): Methods in Yeast Genetics: A Laboratory Course Manual, Cold Spring Harbor Laboratory Press, Cold Spring Harbor, N.Y.)), and MAL21 from *Saccharomyces cerevisiae* ATCC 20598. The DNA fragment thus obtained was inserted into vector pCR (registered trademark) 2.1-TOPO using TOPO TA cloning kit available from Invitrogen Inc. and then subjected to DNA sequencing to verify the inserted gene sequence.

It was confirmed that the nucleotide sequence of AGT1 is identical with that registered in the Data Bank Accession No. YGR289c. With respect to MAL21, 10 clones or more were sequenced independently to verify the nucleotide sequence (SEQ ID NO: 1).

The primers used contain the XbaI or SacI site upstream of the initiation codon and the BamHI site downstream of the termination codon and are designed to integrate into the expression vector. Amplification of the target gene by PCR using chromosomal DNA and subsequent isolation can be performed by methods well known to those skilled in the art, including preparation of PCR primers. The nucleotide sequence of MAL 21 is shown in FIG. 1 and its amino acid sequence is shown in FIG. 2.

<Expression Plasmid>

In the present invention, the 3 expression vectors (1) to (3) were used.
(1) pJHXSB (FIG. 12)
(2) pYCGPY (FIG. 13)
(3) pUP3GLP (FIG. 14)

<Yeast Strains>

In the present invention, the strains (1) to (3) were used to obtain transporter genes, the strains (4) and (5) were used for expression of the transpoter genes and comparison among the strains, and the strain (6) was used to confirm the fermentation rate.
(1) S. cerevisiae S288C (ATCC204508) (MATalpha SUC2 mal mel gal2 CUP1)
(2) S. cerevisiae ATCC 96955 (MATa MAL61 MAL62 MAL63 mal64 mal11 MAL12 mal13 ura3-52 leu2-3 leu2-112 trp1 his)
(3) S. cerevisiae ATCC 20598 (MATa suc MAL2 MEL1 his4 leu2)
(4) S. cerevisiae HH1001 (MATa SUC2 mal mel gal2 CUP1 TPI1::TPI1pr-MAL32-G418R ura3)
(5) S. cerevisiae Δ152 (MATa mal61Δ::TRP1 MAL62 MAL63 mal64 mal11 MAL12 mal13 ura3-52 leu2-3 leu2-112 trp1 his)
(6) bottom-fermenting beer yeast Weihenstephan 194

<Introduction of Restriction Enzyme Recognition Sites>

PCR was performed using primers having the sequences of restriction enzyme recognition sites to introduce the restriction enzyme recognition sites. The DNA sequences of primers are shown in TABLE 3. Specifically, PCR was performed using AGT1 or MAL21 gene-introduced plasmid pCR (registered trademark) 2.1-TOPO as a template in the combination of primers shown in TABLE 4 to obtain 5 DNA fragments of AGT1-SaS, AGT1-SaK, AGT1-SK, AGT1-SB and AGT1-KB for the AGT1 gene and 5 DNA fragments of MAL21-SaS, MAL21-SaK, MAL21-SK, MAL21-SB and MAL21-KB for the MAL21 gene. The schematic diagram of each fragment is given in TABLES 2 and 3 below. The DNA fragments obtained were inserted into plasmid pCR (registered trademark) 2.1-TOPO and sequenced to confirm that any nucleotide substituted from the original gene other than the introduced restriction enzyme site was not found. The respective DNA fragments were excised from the plasmid using restriction enzymes SadI, SalI, KpnI, BamHI, etc. and used to construct the hybrid transporter genes described below.

<Construction of Hybrid Transporter Genes>

Six hybrid transporter genes of AAM, AMA, AMM, MAA, MAM and MMA shown in FIG. 7 were constructed. Each hybrid transporter was obtained by incorporating each fragment obtained above into expression vector pYCGPY at the SacI-BamHI site in the combination shown in FIG. 7. In more details, pYCGPY was digested with Sad and BamHI, the digestion product was subjected to dephosphorylation treatment with bacterial alkali phosphatase and its linearized vector was ligated with the DNA fragment described above. Then, the ligation product was transformed into E. coli DH5α. A plasmid was prepared from several colonies which became ampicillin-resistant. By digesting with the combination of restriction enzymes present only in the MAL21 or AGT1 gene and then performing agarose gel electrophoresis, it was confirmed from the size of the detected fragment that the target hybrid transporter gene was incorporated into the vector pYCGPY. In pYCGPY, the transporter gene is transcribed from PYK1 promoter. Also, each hybrid transporter was excised from pYCGPY using SacI-BamHI and incorporated into the SacI-BamHI site in expression vector pJHXSB. In pJHXSB, the transporter gene is transcribed from TPI1 promoter.

The notation for the mutants such as MMA, MAA, MAM, etc. used in the present invention means a nucleotide sequence containing the following nucleotide sequences consecutively, in the notation of which the first letter indicates a nucleotide sequence encoding an amino acid sequence derived from the N-terminal domain (5' side) to the 12-transmembrane domain, the second letter indicates a nucleotide sequence encoding an amino acid sequence derived from the 12-transmembrane domain, and the third letter indicates a nucleotide sequence encoding an amino acid sequence derived from the C-terminal domain (3' side) to the 12-transmembrane domain. The letter M means that the mutant is derived from MAL21 and the letter A means that the mutant is derived from AGT1. In other words, wild-type AGT1 can be designated AAA, and the hybrid mutant in which the N-terminal domain to the 12-transmembrane domain of AGT1 is replaced by the corresponding domain of MAL21 can be designated MAA.

<Transformation of Yeast>

A yeast was transformed with a plasmid capable of expressing the native or hybrid transporter gene obtained by the method described above. The transformant (a strain bearing no alpha-glucoside transporter gene was used as a host) was selected for pYCGPY on YPD medium containing 300 μg/ml of G418, depending on a marker for the plasmid used. In the case where a ura-strain such as HH1001, etc. was used as a host, the transformant was selected for pJHXSB on a uracil-free synthetic medium, for example, minimal medium (6.7 g/L of Yeast Nitrogen Base w/o amino acids and 20 g/L of glucose), etc.

<Evaluation of the Maltose or Maltotriose Uptake Activity of Transporter Protein>

Expression of the introduced transporter gene in the transformant (a strain bearing no alpha-glucoside transporter gene was used as a host) of the native transporter or the hybrid transporter constructed can be evaluated in terms of the presence or absence of growth in minimal medium containing 0.5% maltose or maltotriose as the only carbon source (when the transformant is auxotrophic, containing its nutrients). For example, one platinum loop of a sample strain was taken from a YPD plate (10 g/L of yeast extract, 20 g/L of polypeptone and 20 g/L of glucose). After washing once with 1 ml of sterile water, the strain was resuspended in sterile water to adjust to OD660=0.2. The cells were collected and suspended again in 1 ml of sterile water. The cell suspension was directly streaked on a test medium using maltose or maltotriose as the only carbon source and its growth was confirmed, whereby it was confirmed to have the maltose or maltotriose uptake activity.

<Evaluation of Transporter Protein on 2-Deoxyglucose Resistance>

2-Deoxyglucose (2-DOG) is a sugar analog that is metabolized to 2-DOG-6-phosphate but not any further and thus cannot be a carbon source. However, it is known that 2-DOG induces glucose repression or glucose-induced inactivation to the same level as that of glucose. It is thus highly probable that a strain grown on this plate would have an α-glucoside transporter less susceptible to glucose-induced inactivation. To determine the resistance to 2-DOG, the following 2 media were used: 0 to 2.0 mM 2-deoxyglucose-containing maltose, etc., minimal medium (6.7 g/L of yeast nitrogen base w/o amino acids, 20 g/L of maltose (when the transformant is auxotrophic, containing its nutrients)), or 0 to 2.0 mM 2-deoxyglucose-containing maltose synthetic complete medium (SCM) (6.7 g/L of yeast nitrogen base w/o amino acids and 20 g/L of maltose, 20 mg/ml of adenine sulfate, 20 mg/ml of uracil, 20 mg/ml of L-tryptophan, 20 mg/ml of L-histidine hydrochloride, 20 mg/ml of L-arginine hydrochloride, 20 mg/ml of L-methionine, 30 mg/ml of L-tyrosine, 30 mg/ml of L-leucine, 30 mg/ml of L-isoleucine, 30 mg/ml of L-lysine hydrochloride, 50 mg/ml of L-phenylalanine, 100 mg/ml of L-glutamic acid, 100 mg/ml of L-aspartic acid, 150 mg/ml of L-valine, 200 mg/ml of L-threonine and 400 mg/ml of L-serine). The resistance was determined by spotting the serial dilution of cell suspension of each transporter-expressed strain indicating OD660=0.2 by 3 µl each onto any plate and culturing at 30° C. for 2 to 3 days.

<Measurement of Level of Transporter Protein Accumulated in Cells>

The level of transporter protein accumulated in cells can be assayed by, e.g., Western blotting. For example, a test strain is harvested from 10 ml of culture broth during the logarithmic growth phase and disrupted in a lysis buffer (8 M urea, 5% (w/v) SDS, 40 mM Tris-HCl (pH 6.8), 0.1 mM EDTA, 1% β-mercaptoethanol) by stirring with glass beads to give the cell extract. A sample of 60 µg total protein was developed by SDS-gel electrophoresis and transferred onto a nitrocellulose membrane followed by Western blotting using rabbit polyclonal anti-Mal61p antibody.

The rabbit polyclonal anti-Mal61p antibody was obtained as follows. The procedures involve inserting a DNA encoding the N-terminal region (Met1-Leu181) of Mal61p at the downstream of GST tag in the pET Expression vector (Novagen Corp.), transforming the resulting plasmid into *Escherichia coli* BL21 (DE3), applying a cell lysate of the transformant to a GST bind resin column and eluting the protein bound to the column. Full details are given in manual attached to Novagen's pET Expression System, GST-Bind™ Affinity Resins (Novagen Corp.). The fused protein thus prepared was applied to SDS-PAGE to confirm the purity. Then, rabbit was immunized using the fused protein as an immunogen to obtain the polyclonal antibody. Effectiveness of the antibody was confirmed by culturing the α-glucoside transporter geneexpressed yeast strain and its host strain free of the gene in a YPM medium (10 g/L of yeast extract, 20 g/L of polypeptone and 5.0 g/L of maltose) and performing Western blotting for the cell lysate using this antibody by the method described above. By using this antibody, Positive bands consistent with the molecular weight of α-glucoside transporter of 68 kDa were detected only in the lysate of the yeast strain in which the α-glucoside transporter gene was expressed. Among the hybrid transporters, only the transporters MMAp, MAMp and MAAp where the N-terminal end is Mal21p type can be detected by this antibody.

The level of Agt1p accumulated in the cells was determined by constructing a gene encoding the fused protein bearing two tandem hematoagglutinin tags at the C-terminal end of Agt1p, obtaining a strain expressing the gene by the procedure described above and using the resulting strain. Mouse monoclonal anti-hematoagglutinin antibody (Covance, Research, Products, Inc.) was used as the antibody.

<Measurement of Degradation Rate of Transporter Protein>

The strain expressing each transporter protein was inoculated into YPD followed by shaking culture at 30° C. overnight. The culture was inoculated into a YPM medium to OD660=1.0, shakeing the culture at 30° C. for 2.5 hours and then the cells were collected. The 60 OD660 units of cells were measured and suspended in 30 ml of a medium for degradation rate measurement (1.7 g/L of yeast nitrogen base w/o amino acids and ammonia, 20 g/L of glucose and 25 mg/L of cycloheximide) preincubated at 30° C., followed by incubation at 30° C. The cell suspension was sampled by 5 ml at an appropriate time (0, 10, 20, 30 and 40 minutes or 0, 30, 60, 90 and 120 minutes) immediately followed by centrifugation. The supernatant was discarded and the cells were frozen using an ethanol-dry ice. The transporter protein was detected from the frozen cells by the method described above and the intensity of the protein band was measured to determine the half life from its diminution rate.

<Evaluation of Maltose Assimilability>

Assimilation of maltose by a yeast constitutively expressing the transporter can be evaluated by aerobically culturing or fermenting a yeast under conditions suitable for the yeast and measuring the amount of maltose in a medium. Sugars can be measured by methods well known to those skilled in the art, for example, liquid chromatography using an IR detector.

Example 1

Degradation Rate of Mal21p and Agt1p in the Presence of Glucose

The MAL21 gene and AGT1 gene obtained by PCR were inserted into an expression vector pYCGPY and transformed into yeast Δ152. The transformant was streaked onto minimal medium (MM) containing 0.5% maltose or maltotriose as the only carbon source and further containing 20 mg/L of uracil, 20 mg/L of histidine, 30 mg/L of leucine and 300 µg/ml of geneticin (FIG. 5). The strain bearing MAL21 could grow only on a maltose medium but the strain bearing AGT1 grew in either medium containing maltose or maltotriose; it was thus confirmed that only AGT1 could take up both sugars. Next, a gene AGT1-2HA encoding a fusion protein in which two hematoagglutinin tags are connected in tandem to the C-terminal domain of Agt1p was constructed and inserted into an expression vector pJHXSB. MAL61 and MAL21 were both inserted into pJHXSB. These constructs were transformed into yeast HH1001. Using the two transformants, the degradation rate was determined by Western blotting in the presence of glucose according to the procedure described in the testing method. The results are shown in FIG. 6. It was found that Agt1-2HAp had a shorter half life as compared to that of Mal61p or Mal21p (see FIG. 6; Agt1-2HAp: 14 minutes, Mal61p: 25 minutes and Mal21p: 118 minutes). It was also found that even with the same α-glucoside transporter, Mal21p had a much longer half life than that of Mal61p (Mal61p: 25 minutes and Mal21p: 118 minutes).

Example 2

Construction of Hybrid Transporter and Confirmation of its Substrate Specificity Agt1p and Mal21p belong to the family of the MFS (major facilitated sugar transporter) and are considered to have 12 transmembrane domains, and N-terminal and C terminal domains are suspected to be cytoplasmic domains on the basis of similarities of its amino acid sequence. Sites involved in the substrate specificity or activity of Agt1p and Mal are unknown. In view of alignments of the two amino acid sequences, the site suspected of being cytoplasmic domains at the N terminus and C terminus has a low similarity, whereas the central 12-transmembrane domain show a high similarity (see FIG. 3). The inventors therefore thought that the central 12-transmembrane domain may have the uptake activity or may affect substrate specificity. The AGT1 and MAL21 genes were obtained by PCR, respectively, in the form of the N-terminal or C-terminal cytoplasmic domain-coding region and the central 12-transmembrane-coding region containing restriction enzyme sites at the both ends. The primers used are shown in TABLE 3 and the relationship between the fragments obtained and primer pairs are shown in TABLE 4. These fragments were used in combination to construct several hybrid transporter genes. The recombination positions used are shown by the cross marks in FIG. 3 and the name and schematic diagram of each hybrid are shown in FIG. 7. The details are described in the testing methods. The expression vector pYCGPY shown in FIG. 7, into which each hybrid transporter gene was inserted, was transformed to yeast Δ152. The transformant was streaked onto minimal medium (MM) (MM: 6.7 g/L of Yeast Nitrogen Base w/o amino acids, 5 g/L of maltose or maltotriose, 20 mg/L of histidine, 30 mg/L of leucine, 20 mg/L of uracil and 300 μg/ml of geneticin) containing 0.5% maltose or maltotriose as the only carbon source and further containing 20 mg/L of uracil, 20 mg/L of histidine, 30 mg/L of leucine and 300 μg/ml of geneticin (FIG. 8). The results reveal that the 3 hybrid transporters AAMp, MAMp and MAAp wherein the central 12-transmembrane domain are derived from Agt1p has the maltotriose uptake activity.

TABLE 3

Primers for introducing cleavage sites with restriction enzymes

| Primer | Primer Sequence |
|---|---|
| M12(-20)primer | 5'-gtaaaacgac ggccagt-3' |
| M13 Reverse primer | 5'-ggaaacagct atgaccatg-3' |
| AGTNSF | 5'-tgtcgactac cctggttatg-3' |
| AGTNSR | 5'-agtcgacact aatatggacc a |
| AGTCKF | 5'-gggtacctgc cagaaaattt-3' |
| AGTCKR | 5'-aggtaccccc tggttgaaaa-3' |
| Mal21NSF | 5'-tgtcgacaac attgattcaa gag-3' |
| MAL21NSR | 5'-tgtcgacact aatagtgacc aag-3' |
| MAL21CKF | 5'-gggtaccagc aagaaagttc aa-3' |
| MAL21CKR | 5'-tggtacccca agtctaaaca att-3' |

(The sequences above are shown by SEQ ID NOS: 23 through 32)

TABLE 4

PCR primer pairs used to obtain fragments

| | Primer used for PCR | |
|---|---|---|
| Fragment | Forward | Reverse |
| AGT1-SaS | M13(-20)primer | AGTNSR |
| AGT1-SaK | M13(-20)primer | AGTCKR |
| AGT1-SK | AGTNSF | AGTCKR |
| AGT1-SB | AGTNSF | M13 Reverse primer |
| AGT1-KB | AGTCKF | M13 Reverse primer |
| MAL21-SaS | M13(-20)primer | MAL21NSR |
| MAL21-SaK | M13(-20)primer | MAL21CKR |
| MAL21-SK | MAL21NSF | MAL21CKR |
| MAL21-SB | MAL21NSF | M13 Reverse primer |
| MAL21-KB | MAL21CKF | M13 Reverse primer |

Example 3

2-Deoxyglucose Resistance of Hybrid Transporter

The hybrid transporter gene described in EXAMPLE 2 was excised from pYCGPY using SacI-BamHI and incorporated into the SacI-BamHI of pJHXSB. Each expression vector thus constructed was transformed into HH1001. HH1001 is a ura3-sibling of the mal-strain X2180-1A and constitutively expresses maltase since TPI1p::MAL32 (which encodes maltase gene) is incorporated therein. A plate of 2% maltose-containing synthetic complete medium (SCM) supplemented with 0 mM to 2 mM of 2-deoxyglucose (2-DOG) was prepared. As described in the testing method, the 2-DOG resistance of each transformant was examined. 2-DOG is a sugar analog that is metabolized to 2-DOG-6-phosphate but not any further and thus cannot be a carbon source. However, it is known that 2-DOG induces glucose repression or glucose-induced inactivation to the same level as glucose. It is therefore highly probable that a strain grown on this plate would have an α-glucoside transporter less susceptible to glucose-induced inactivation. The results are shown in FIG. 9. The hybrid transporters MMAp and MAAp having the MAL21-derived N-terminal cytoplasmic domain grew even in the medium supplemented with 1 mM of 2-DOG. Also, MAMp grew in the medium supplemented with 2 mM of 2-DOG and was found to have the same 2-DOG resistance as that of native Mal21p and be less susceptible to glucose-induced degradation.

Example 4

Degradation Rate of Hybrid Transporter in the Presence of Glucose

As demonstrated in EXAMPLE 3, it is considered that the hybrid transporters MMAp, MAAp and MAMp which have N-terminus cytoplasmic domain derived from Mal21p would be less susceptible to glucose-induced degradation. To verify this, the degradation rates of MMAp, MAAp and MAMp in the presence of glucose were measured by the procedures shown in the testing method (FIG. 10). Any of the hybrid transporters had a longer half life than that of Agt1-2HAp. In particular, MAMp had a half life of 119 minutes, i.e., almost the same half life as that of Mal21p (118 minutes). Thus, it became possible that Agt1p which was rapidly degradated by glucose was modified to construct the transporter less susceptible to degradation.

Reference Example 1

Test on Happoshu (Low-Malt Beer) Wort Fermentation by Bottom-Fermenting Beer Yeast where MAL21 was Highly Expressed The transporter MAL21 having the resistance to glucose-induced degradation was incorporated into plasmid pUP3GLP at the XbaI (or SacI)-BamHI site. pUP3GLP is shown in FIG. 14. pUP3GLP is a Yip-type plasmid, in which the transporter gene is expressed from glyceraldehyde triphosphate dehydrogenase promoter (TDH3p). After each plasmid was digested at the EcoRV site in URA3, the digested product was transformed into bottom-fermenting beer yeast (Weihenstephan 194) and the transformant was spread onto a YGP plate (10 g/L of yeast extract, 20 g/L of polypeptone and 20 g/L of galactose) supplemented with 0.3 μg/ml of cycloheximide. It was confirmed by PCR that the objective expression cassette was inserted into the URA3 gene on the chromosome of Weihenstephan 194.

Weihenstephan 194 (URA3::TDH3p::MAL21) and parent strain Weihenstephan 194 were inoculated into two kinds of happoshu wort. The happoshu wort is a wort with less than 25% malt content in the raw materials except for water, in which glycosylated starch, hops, etc. are used. One of the worts for happoshu has an initial extract concentration of 14.0% and contains sugars in proportions of 1.2% of glucose, 6.6% of maltose and 2.2% of maltotriose. Another glucose-rich happoshu wort has an initial extract concentration of 15.6% and contains sugars in proportions of 4.7% of glucose, 5.4% of maltose and 1.7% of maltotriose. Each wort was prepared by adding glycosylated starch having different sugar proportions to the same volume of wort (final concentration, less than 25% malt content). Wet cells were pitched into the wort adjusting to 7.5 g/L, which was allowed to ferment at 15° C. The maltose content in the moromi mash during the fermentation was measured. The results are shown in FIG. 11.

In any of the happoshu worts, the assimilation rate of maltose in the MAL21-highly expressed strains was markedly faster than in the parent strain Weihenstephan 194. Especially in the case of glucose-rich happoshu wort, its effect was remarkable. The high initial extract concentration means that the glucose content is high and in this case, the effect of the transporter having the resistance to glucose-induced degradation was well observed. Accordingly, in the yeast into which the hybrid transporter MAAp or MAMp, it is fully expected from the results of, e.g., FIGS. 10 and 11 to facilitate the maltotriose assimilation with high concentrations of monosaccharides such as glucose, etc.

INDUSTRIAL APPLICABILITY

As described above, it has been found that Agt1p which is an alpha-glucoside transporter has a shorter half life in the presence of glucose than that of other α-glucoside transporters. It has also been found that even among the same α-glucoside transporters, Mal21p is hardly degraded by glucose, unlike Mal61p. As a result of 6 hybrid transporters being constructed, it has been found that the hybrid transporters AAMp, MAAp and MAMp in which the central 12-transmembrane domain is of Agt1p type can all take up maltotriose. It has also been found that the hybrid transporters MAAp, MMAp and MAMp, in which the N-terminal cytoplasmic domain is of Mal21p type, are all less susceptible to degradation in the presence of glucose, than Agt1p. Among them, the hybrid transporter MAM in which both N-terminal and C-terminal cytoplasmic domains are of Mal21p and only the central 12-transmembrane domain is of Agt1p type has a half life as long as in Mal21p and can take up maltotriose. By using a yeast expressing its mutant transporter (irrespective of laboratory yeast or brewery yeast), assimilation of sugars in moromi mash, such as maltotriose, etc. that the transporter can take up can be accelerated. It is more effective especially where the concentration of monosaccharides such as glucose is high.

The invention claimed is:

1. An isolated polynucleotide encoding an α-glucoside transporter protein having a resistance to glucose-induced inactivation and/or degradation, said polynucleotide comprising (a) the nucleotide sequence of SEQ ID NO: 13 or SEQ ID NO: 15 or (b) a nucleotide sequence encoding a protein consisting of the amino acid sequence of SEQ ID NO:14 or SEQ ID NO: 16.

2. The polynucleotide according to claim 1, wherein said polynucleotide comprising the nucleotide sequence of SEQ ID NO: 13 or SEQ ID NO: 15.

3. The polynucleotide according to claim 1, wherein said polynucleotide comprising a nucleotide sequence encoding a protein consisting of the amino acid sequence of SEQ ID NO: 14 or SEQ ID NO: 16.

4. The polynucleotide according to claim 1, which is a DNA.

5. A vector comprising the polynucleotide according to claim 1.

6. A yeast transfected with the vector according to claim 5.

7. The yeast according to claim 6, wherein said vector is an expression vector.

* * * * *

SEQUENCE LISTING

```
<160> NUMBER OF SEQ ID NOS: 33

<210> SEQ ID NO 1
<211> LENGTH: 1842
<212> TYPE: DNA
<213> ORGANISM: Saccharomyces cerevisiae
<220> FEATURE:
<221> NAME/KEY: CDS
<222> LOCATION: (1)..(1842)
<223> OTHER INFORMATION: Mal21p

<400> SEQUENCE: 1 atg aag gga tta tcc tca tta ata aac aga aaa aaa gac agg aac gac      48
Met Lys Gly Leu Ser Ser Leu Ile Asn Arg Lys Lys Asp Arg Asn Asp
1               5                   10                  15 tca cac tta gat gag atc gag aat ggc gtg aac gct acc gaa ttc aac      96
Ser His Leu Asp Glu Ile Glu Asn Gly Val Asn Ala Thr Glu Phe Asn
            20                  25                  30 tcg ata gag atg gag gag caa ggt aag aaa agt gat ttt ggt ctt tcc     144
Ser Ile Glu Met Glu Glu Gln Gly Lys Lys Ser Asp Phe Gly Leu Ser
        35                  40                  45 cat cat gag tac ggt cca ggt tca cta ata cca aac gat aat aat gaa     192
His His Glu Tyr Gly Pro Gly Ser Leu Ile Pro Asn Asp Asn Asn Glu
    50                  55                  60 gaa gtc ccc gac ctt ctc gat gaa gct atg cag gac gcc aaa gag gca     240
Glu Val Pro Asp Leu Leu Asp Glu Ala Met Gln Asp Ala Lys Glu Ala
65                  70                  75                  80 gat gaa agt gag agg gga atg cca ctc atg aca gct ttg aag aca tat     288
Asp Glu Ser Glu Arg Gly Met Pro Leu Met Thr Ala Leu Lys Thr Tyr
                85                  90                  95 cca aaa gct gct gct tgg tca cta tta gtt tcc aca aca ttg att caa     336
Pro Lys Ala Ala Ala Trp Ser Leu Leu Val Ser Thr Thr Leu Ile Gln
            100                 105                 110
```

| | | |
|---|---|---|
| gag ggt tat gac aca gcc att cta gga gct ttc tat gcc ctg cct gtt<br>Glu Gly Tyr Asp Thr Ala Ile Leu Gly Ala Phe Tyr Ala Leu Pro Val<br>115 120 125 | | 384 |
| ttt caa aaa aaa tat ggt tct ttg aat agc aat aca gga gat tat gaa<br>Phe Gln Lys Lys Tyr Gly Ser Leu Asn Ser Asn Thr Gly Asp Tyr Glu<br>130 135 140 | | 432 |
| att tca gtt tct tgg caa atc ggt cta tgt cta tgc tac atg gca ggt<br>Ile Ser Val Ser Trp Gln Ile Gly Leu Cys Leu Cys Tyr Met Ala Gly<br>145 150 155 160 | | 480 |
| gaa att gtg ggg cta cag cta acg ggg ccc tcc gtg gat ctt gtt gga<br>Glu Ile Val Gly Leu Gln Leu Thr Gly Pro Ser Val Asp Leu Val Gly<br>165 170 175 | | 528 |
| aat cgt tac aca ttg atc atg gcg ttg ttc ttt tta gcg gct ttc att<br>Asn Arg Tyr Thr Leu Ile Met Ala Leu Phe Phe Leu Ala Ala Phe Ile<br>180 185 190 | | 576 |
| ttc att ctg tat ttt tgc aag agt ttg ggt atg att gcc gtg gga cag<br>Phe Ile Leu Tyr Phe Cys Lys Ser Leu Gly Met Ile Ala Val Gly Gln<br>195 200 205 | | 624 |
| gca ttg tgt ggt atg cca tgg ggt tgt ttc caa tgt ttg acc gtt tct<br>Ala Leu Cys Gly Met Pro Trp Gly Cys Phe Gln Cys Leu Thr Val Ser<br>210 215 220 | | 672 |
| tat gct tct gaa att tgt cct ttg gcc cta aga tac tat ttg acg act<br>Tyr Ala Ser Glu Ile Cys Pro Leu Ala Leu Arg Tyr Tyr Leu Thr Thr<br>225 230 235 240 | | 720 |
| tat tct aat tta tgt tgg acg ttc ggt caa ctt ttc gct gct ggt att<br>Tyr Ser Asn Leu Cys Trp Thr Phe Gly Gln Leu Phe Ala Ala Gly Ile<br>245 250 255 | | 768 |
| atg aaa aat tcc cag aac aaa tat gcc aac tca gaa cta gga tat aag<br>Met Lys Asn Ser Gln Asn Lys Tyr Ala Asn Ser Glu Leu Gly Tyr Lys<br>260 265 270 | | 816 |
| cta cct ttt gct ttg cag tgg atc tgg ccc ctt cct ttg gcg gta ggt<br>Leu Pro Phe Ala Leu Gln Trp Ile Trp Pro Leu Pro Leu Ala Val Gly<br>275 280 285 | | 864 |
| att ttt ttt gca cca gag tct cca tgg tgg ctg gtt aaa aaa gga agg<br>Ile Phe Phe Ala Pro Glu Ser Pro Trp Trp Leu Val Lys Lys Gly Arg<br>290 295 300 | | 912 |
| att gat caa gcg agg aga tca ctt gaa aga aca tta agt ggt aaa gga<br>Ile Asp Gln Ala Arg Arg Ser Leu Glu Arg Thr Leu Ser Gly Lys Gly<br>305 310 315 320 | | 960 |
| ccc gag aaa gaa tta cta gtg act atg gaa ctc gat aaa atc aaa act<br>Pro Glu Lys Glu Leu Leu Val Thr Met Glu Leu Asp Lys Ile Lys Thr<br>325 330 335 | | 1008 |
| act ata gaa aag gag cag aaa atg tct gat gaa gga act tac tgg gat<br>Thr Ile Glu Lys Glu Gln Lys Met Ser Asp Glu Gly Thr Tyr Trp Asp<br>340 345 350 | | 1056 |
| tgt gtg aaa gat ggt att aac agg aga aga acg aga ata gct tgt tta<br>Cys Val Lys Asp Gly Ile Asn Arg Arg Arg Thr Arg Ile Ala Cys Leu<br>355 360 365 | | 1104 |
| tgt tgg atc ggt caa tgc tcc tgt ggt gca tca tta att ggt tat tca<br>Cys Trp Ile Gly Gln Cys Ser Cys Gly Ala Ser Leu Ile Gly Tyr Ser<br>370 375 380 | | 1152 |
| act tac ttt tat gaa aaa gct ggt gtt agc act gat acg gct ttt act<br>Thr Tyr Phe Tyr Glu Lys Ala Gly Val Ser Thr Asp Thr Ala Phe Thr<br>385 390 395 400 | | 1200 |
| ttc agt att atc caa tat tgt ctt ggt att gct gca acg ttt gta tcc<br>Phe Ser Ile Ile Gln Tyr Cys Leu Gly Ile Ala Ala Thr Phe Val Ser<br>405 410 415 | | 1248 |
| tgg tgg gct tca aaa tat tgt ggc aga ttt gac ctt tat gct ttt ggg<br>Trp Trp Ala Ser Lys Tyr Cys Gly Arg Phe Asp Leu Tyr Ala Phe Gly<br>420 425 430 | | 1296 |

```
ctg gct ttt cag gct att atg ttc ttc att atc ggt ggt tta gga tgt   1344
Leu Ala Phe Gln Ala Ile Met Phe Phe Ile Ile Gly Gly Leu Gly Cys
        435                 440                 445 tca gac act cat ggc gct aaa atg ggt agt ggt gct ctt cta atg gtt   1392
Ser Asp Thr His Gly Ala Lys Met Gly Ser Gly Ala Leu Leu Met Val
450                 455                 460 gtc gcg ttc ttt tac aac ctc ggt att gca cct gtt gtt ttt tgc tta   1440
Val Ala Phe Phe Tyr Asn Leu Gly Ile Ala Pro Val Val Phe Cys Leu
465                 470                 475                 480 gtg tct gaa atg ccg tct tca agg cta aga acc aaa aca att att ttg   1488
Val Ser Glu Met Pro Ser Ser Arg Leu Arg Thr Lys Thr Ile Ile Leu
                485                 490                 495 gct cgt aat gct tac aat gtg atc caa gtt gta gtt aca gtt ttg att   1536
Ala Arg Asn Ala Tyr Asn Val Ile Gln Val Val Val Thr Val Leu Ile
            500                 505                 510 atg tac caa ttg aac tca gag aaa tgg aat tgg ggt gct aaa tca ggc   1584
Met Tyr Gln Leu Asn Ser Glu Lys Trp Asn Trp Gly Ala Lys Ser Gly
        515                 520                 525 ttt ttc tgg gga gga ttt tgt ctg gcc act tta gct tgg gct gtt gtc   1632
Phe Phe Trp Gly Gly Phe Cys Leu Ala Thr Leu Ala Trp Ala Val Val
530                 535                 540 gat tta cca gaa acc gct ggc agg act ttt att gag ata aat gaa ttg   1680
Asp Leu Pro Glu Thr Ala Gly Arg Thr Phe Ile Glu Ile Asn Glu Leu
545                 550                 555                 560 ttt aga ctt ggt gtt cca gca aga aag ttc aag tcg act aaa gtc gac   1728
Phe Arg Leu Gly Val Pro Ala Arg Lys Phe Lys Ser Thr Lys Val Asp
                565                 570                 575 cct ttt gca gct gcc aaa gca gca gct gca gaa att aat gtt aaa gat   1776
Pro Phe Ala Ala Ala Lys Ala Ala Ala Ala Glu Ile Asn Val Lys Asp
            580                 585                 590 ccg aag gaa gat ttg gaa act tct gtg gta gat gaa ggg cga aac acc   1824
Pro Lys Glu Asp Leu Glu Thr Ser Val Val Asp Glu Gly Arg Asn Thr
        595                 600                 605 tca tct gtt gtg aac aaa                                           1842
Ser Ser Val Val Asn Lys
    610

<210> SEQ ID NO 2
<211> LENGTH: 614
<212> TYPE: PRT
<213> ORGANISM: Saccharomyces cerevisiae

<400> SEQUENCE: 2

Met Lys Gly Leu Ser Ser Leu Ile Asn Arg Lys Lys Asp Arg Asn Asp
1               5                   10                  15

Ser His Leu Asp Glu Ile Glu Asn Gly Val Asn Ala Thr Glu Phe Asn
            20                  25                  30

Ser Ile Glu Met Glu Glu Gln Gly Lys Lys Ser Asp Phe Gly Leu Ser
        35                  40                  45

His His Glu Tyr Gly Pro Gly Ser Leu Ile Pro Asn Asp Asn Asn Glu
    50                  55                  60

Glu Val Pro Asp Leu Leu Asp Glu Ala Met Gln Asp Ala Lys Glu Ala
65                  70                  75                  80

Asp Glu Ser Glu Arg Gly Met Pro Leu Met Thr Ala Leu Lys Thr Tyr
                85                  90                  95

Pro Lys Ala Ala Ala Trp Ser Leu Leu Val Ser Thr Thr Leu Ile Gln
            100                 105                 110

Glu Gly Tyr Asp Thr Ala Ile Leu Gly Ala Phe Tyr Ala Leu Pro Val
        115                 120                 125
```

```
Phe Gln Lys Lys Tyr Gly Ser Leu Asn Ser Asn Thr Gly Asp Tyr Glu
    130                 135                 140

Ile Ser Val Ser Trp Gln Ile Gly Leu Cys Leu Cys Tyr Met Ala Gly
145                 150                 155                 160

Glu Ile Val Gly Leu Gln Leu Thr Gly Pro Ser Val Asp Leu Val Gly
                165                 170                 175

Asn Arg Tyr Thr Leu Ile Met Ala Leu Phe Leu Ala Ala Phe Ile
                180                 185                 190

Phe Ile Leu Tyr Phe Cys Lys Ser Leu Gly Met Ile Ala Val Gly Gln
        195                 200                 205

Ala Leu Cys Gly Met Pro Trp Gly Cys Phe Gln Cys Leu Thr Val Ser
    210                 215                 220

Tyr Ala Ser Glu Ile Cys Pro Leu Ala Leu Arg Tyr Tyr Leu Thr Thr
225                 230                 235                 240

Tyr Ser Asn Leu Cys Trp Thr Phe Gly Gln Leu Phe Ala Ala Gly Ile
                245                 250                 255

Met Lys Asn Ser Gln Asn Lys Tyr Ala Asn Ser Glu Leu Gly Tyr Lys
                260                 265                 270

Leu Pro Phe Ala Leu Gln Trp Ile Trp Pro Leu Pro Leu Ala Val Gly
            275                 280                 285

Ile Phe Phe Ala Pro Glu Ser Pro Trp Trp Leu Val Lys Lys Gly Arg
    290                 295                 300

Ile Asp Gln Ala Arg Arg Ser Leu Glu Arg Thr Leu Ser Gly Lys Gly
305                 310                 315                 320

Pro Glu Lys Glu Leu Leu Val Thr Met Glu Leu Asp Lys Ile Lys Thr
                325                 330                 335

Thr Ile Glu Lys Glu Gln Lys Met Ser Asp Gly Tyr Trp Asp
                340                 345                 350

Cys Val Lys Asp Gly Ile Asn Arg Arg Arg Thr Arg Ile Ala Cys Leu
        355                 360                 365

Cys Trp Ile Gly Gln Cys Ser Cys Gly Ala Ser Leu Ile Gly Tyr Ser
    370                 375                 380

Thr Tyr Phe Tyr Glu Lys Ala Gly Val Ser Thr Asp Thr Ala Phe Thr
385                 390                 395                 400

Phe Ser Ile Ile Gln Tyr Cys Leu Gly Ile Ala Ala Thr Phe Val Ser
                405                 410                 415

Trp Trp Ala Ser Lys Tyr Cys Gly Arg Phe Asp Leu Tyr Ala Phe Gly
                420                 425                 430

Leu Ala Phe Gln Ala Ile Met Phe Phe Ile Ile Gly Gly Leu Gly Cys
            435                 440                 445

Ser Asp Thr His Gly Ala Lys Met Gly Ser Gly Ala Leu Leu Met Val
    450                 455                 460

Val Ala Phe Phe Tyr Asn Leu Gly Ile Ala Pro Val Val Phe Cys Leu
465                 470                 475                 480

Val Ser Glu Met Pro Ser Ser Arg Leu Arg Thr Lys Thr Ile Ile Leu
                485                 490                 495

Ala Arg Asn Ala Tyr Asn Val Ile Gln Val Val Thr Val Leu Ile
                500                 505                 510

Met Tyr Gln Leu Asn Ser Glu Lys Trp Asn Trp Gly Ala Lys Ser Gly
            515                 520                 525

Phe Phe Trp Gly Gly Phe Cys Leu Ala Thr Leu Ala Trp Ala Val Val
    530                 535                 540

Asp Leu Pro Glu Thr Ala Gly Arg Thr Phe Ile Glu Ile Asn Glu Leu
```

```
                545                 550                 555                 560
            Phe Arg Leu Gly Val Pro Ala Arg Lys Phe Lys Ser Thr Lys Val Asp
                            565                 570                 575
            Pro Phe Ala Ala Ala Lys Ala Ala Ala Ala Glu Ile Asn Val Lys Asp
                        580                 585                 590
            Pro Lys Glu Asp Leu Glu Thr Ser Val Val Asp Glu Gly Arg Asn Thr
                    595                 600                 605
            Ser Ser Val Val Asn Lys
                610

<210> SEQ ID NO 3
<211> LENGTH: 1848
<212> TYPE: DNA
<213> ORGANISM: Saccharomyces cerevisiae
<220> FEATURE:
<221> NAME/KEY: CDS
<222> LOCATION: (1)..(1848)
<223> OTHER INFORMATION: Agt1p

<400> SEQUENCE: 3 atg aaa aat atc att tca ttg gta agc aag aag aag gct gcc tca aaa         48
Met Lys Asn Ile Ile Ser Leu Val Ser Lys Lys Lys Ala Ala Ser Lys
1               5                  10                  15 aat gag gat aaa aac att tct gag tct tca aga gat att gta aac caa         96
Asn Glu Asp Lys Asn Ile Ser Glu Ser Ser Arg Asp Ile Val Asn Gln
            20                  25                  30 cag gag gtt ttc aat act gaa gat ttt gaa gaa ggg aaa aag gat agt        144
Gln Glu Val Phe Asn Thr Glu Asp Phe Glu Glu Gly Lys Lys Asp Ser
        35                  40                  45 gcc ttt gag cta gac cac tta gag ttc acc acc aat tca gcc cag tta        192
Ala Phe Glu Leu Asp His Leu Glu Phe Thr Thr Asn Ser Ala Gln Leu
    50                  55                  60 gga gat tct gac gaa gat aac gag aat gtg att aat gag atg aac gct        240
Gly Asp Ser Asp Glu Asp Asn Glu Asn Val Ile Asn Glu Met Asn Ala
65                  70                  75                  80 act gat gat gca aat gaa gct aac agc gag gaa aaa agc atg act ttg        288
Thr Asp Asp Ala Asn Glu Ala Asn Ser Glu Glu Lys Ser Met Thr Leu
                85                  90                  95 aag cag gcg ttg cta aaa tat cca aaa gca gcc ctg tgg tcc ata tta        336
Lys Gln Ala Leu Leu Lys Tyr Pro Lys Ala Ala Leu Trp Ser Ile Leu
            100                 105                 110 gtg tct act acc ctg gtt atg gaa ggt tat gat acc gca cta ctg agc        384
Val Ser Thr Thr Leu Val Met Glu Gly Tyr Asp Thr Ala Leu Leu Ser
        115                 120                 125 gca ctg tat gcc ctg cca gtt ttt cag aga aaa ttc ggt act ttg aac        432
Ala Leu Tyr Ala Leu Pro Val Phe Gln Arg Lys Phe Gly Thr Leu Asn
    130                 135                 140 ggg gag ggt tct tac gaa att act tcc caa tgg cag att ggt tta aac        480
Gly Glu Gly Ser Tyr Glu Ile Thr Ser Gln Trp Gln Ile Gly Leu Asn
145                 150                 155                 160 atg tgt gtc ctt tgt ggt gag atg att ggt ttg caa atc acg act tat        528
Met Cys Val Leu Cys Gly Glu Met Ile Gly Leu Gln Ile Thr Thr Tyr
                165                 170                 175 atg gtt gaa ttt atg ggg aat cgt tat acg atg att aca gca ctt ggt        576
Met Val Glu Phe Met Gly Asn Arg Tyr Thr Met Ile Thr Ala Leu Gly
            180                 185                 190 ttg tta act gct tat atc ttt atc ctc tac tac tgt aaa agt tta gct        624
Leu Leu Thr Ala Tyr Ile Phe Ile Leu Tyr Tyr Cys Lys Ser Leu Ala
        195                 200                 205 atg att gct gtg gga caa att ctc tca gct ata cca tgg ggt tgt ttc        672
Met Ile Ala Val Gly Gln Ile Leu Ser Ala Ile Pro Trp Gly Cys Phe
```

-continued

|  |  |  |  | 210 |  |  |  | 215 |  |  |  | 220 |  |  |  |
|---|---|---|---|---|---|---|---|---|---|---|---|---|---|---|---|
| caa | agt | ttg | gct | gtt | act | tat | gct | tcg | gaa | gtt | tgc | cct | tta | gca | tta | 720 |
| Gln | Ser | Leu | Ala | Val | Thr | Tyr | Ala | Ser | Glu | Val | Cys | Pro | Leu | Ala | Leu |
| 225 |  |  |  | 230 |  |  |  | 235 |  |  |  | 240 |  |  |  |

| aga | tat | tac | atg | acc | agt | tac | tcc | aac | att | tgt | tgg | tta | ttt | ggt | caa | 768 |
|---|---|---|---|---|---|---|---|---|---|---|---|---|---|---|---|---|
| Arg | Tyr | Tyr | Met | Thr | Ser | Tyr | Ser | Asn | Ile | Cys | Trp | Leu | Phe | Gly | Gln |
|  |  |  |  | 245 |  |  |  | 250 |  |  |  | 255 |  |  |  |

| atc | ttc | gcc | tct | ggt | att | atg | aaa | aac | tca | caa | gag | aat | tta | ggg | aac | 816 |
|---|---|---|---|---|---|---|---|---|---|---|---|---|---|---|---|---|
| Ile | Phe | Ala | Ser | Gly | Ile | Met | Lys | Asn | Ser | Gln | Glu | Asn | Leu | Gly | Asn |
|  |  |  | 260 |  |  |  | 265 |  |  |  | 270 |  |  |  |  |

| tcc | gac | ttg | ggc | tat | aaa | ttg | cca | ttt | gct | tta | caa | tgg | att | tgg | cct | 864 |
|---|---|---|---|---|---|---|---|---|---|---|---|---|---|---|---|---|
| Ser | Asp | Leu | Gly | Tyr | Lys | Leu | Pro | Phe | Ala | Leu | Gln | Trp | Ile | Trp | Pro |
|  |  | 275 |  |  |  | 280 |  |  |  | 285 |  |  |  |  |  |

| gct | cct | tta | atg | atc | ggt | atc | ttt | ttc | gct | cct | gag | tcg | ccc | tgg | tgg | 912 |
|---|---|---|---|---|---|---|---|---|---|---|---|---|---|---|---|---|
| Ala | Pro | Leu | Met | Ile | Gly | Ile | Phe | Phe | Ala | Pro | Glu | Ser | Pro | Trp | Trp |
|  | 290 |  |  |  | 295 |  |  |  | 300 |  |  |  |  |  |  |

| ttg | gtg | aga | aag | gat | agg | gtc | gct | gag | gca | aga | aaa | tct | tta | agc | aga | 960 |
|---|---|---|---|---|---|---|---|---|---|---|---|---|---|---|---|---|
| Leu | Val | Arg | Lys | Asp | Arg | Val | Ala | Glu | Ala | Arg | Lys | Ser | Leu | Ser | Arg |
| 305 |  |  |  | 310 |  |  |  | 315 |  |  |  | 320 |  |  |  |

| att | ttg | agt | ggt | aaa | ggc | gcc | gag | aag | gac | att | caa | gtt | gat | ctt | act | 1008 |
|---|---|---|---|---|---|---|---|---|---|---|---|---|---|---|---|---|
| Ile | Leu | Ser | Gly | Lys | Gly | Ala | Glu | Lys | Asp | Ile | Gln | Val | Asp | Leu | Thr |
|  |  |  | 325 |  |  |  | 330 |  |  |  | 335 |  |  |  |  |

| tta | aag | cag | att | gaa | ttg | act | att | gaa | aaa | gaa | aga | ctt | tta | gca | tct | 1056 |
|---|---|---|---|---|---|---|---|---|---|---|---|---|---|---|---|---|
| Leu | Lys | Gln | Ile | Glu | Leu | Thr | Ile | Glu | Lys | Glu | Arg | Leu | Leu | Ala | Ser |
|  |  | 340 |  |  |  | 345 |  |  |  | 350 |  |  |  |  |  |

| aaa | tca | gga | tca | ttc | ttt | aat | tgt | ttc | aag | gga | gtt | aat | gga | aga | aga | 1104 |
|---|---|---|---|---|---|---|---|---|---|---|---|---|---|---|---|---|
| Lys | Ser | Gly | Ser | Phe | Phe | Asn | Cys | Phe | Lys | Gly | Val | Asn | Gly | Arg | Arg |
|  | 355 |  |  |  | 360 |  |  |  | 365 |  |  |  |  |  |  |

| acg | aga | ctt | gca | tgt | tta | act | tgg | gta | gct | caa | aat | agt | agc | ggt | gcc | 1152 |
|---|---|---|---|---|---|---|---|---|---|---|---|---|---|---|---|---|
| Thr | Arg | Leu | Ala | Cys | Leu | Thr | Trp | Val | Ala | Gln | Asn | Ser | Ser | Gly | Ala |
| 370 |  |  |  | 375 |  |  |  | 380 |  |  |  |  |  |  |  |

| gtt | tta | ctt | ggt | tac | tcg | aca | tat | ttt | ttt | gaa | aga | gca | ggt | atg | gcc | 1200 |
|---|---|---|---|---|---|---|---|---|---|---|---|---|---|---|---|---|
| Val | Leu | Leu | Gly | Tyr | Ser | Thr | Tyr | Phe | Phe | Glu | Arg | Ala | Gly | Met | Ala |
| 385 |  |  |  | 390 |  |  |  | 395 |  |  |  | 400 |  |  |  |

| acc | gac | aag | gcg | ttt | act | ttt | tct | cta | att | cag | tac | tgt | ctt | ggg | tta | 1248 |
|---|---|---|---|---|---|---|---|---|---|---|---|---|---|---|---|---|
| Thr | Asp | Lys | Ala | Phe | Thr | Phe | Ser | Leu | Ile | Gln | Tyr | Cys | Leu | Gly | Leu |
|  |  |  | 405 |  |  |  | 410 |  |  |  | 415 |  |  |  |  |

| gcg | ggt | aca | ctt | tgc | tcc | tgg | gta | ata | tct | ggc | cgt | gtt | ggt | aga | tgg | 1296 |
|---|---|---|---|---|---|---|---|---|---|---|---|---|---|---|---|---|
| Ala | Gly | Thr | Leu | Cys | Ser | Trp | Val | Ile | Ser | Gly | Arg | Val | Gly | Arg | Trp |
|  | 420 |  |  |  | 425 |  |  |  | 430 |  |  |  |  |  |  |

| aca | ata | ctg | acc | tat | ggt | ctt | gca | ttt | caa | atg | gtc | tgc | tta | ttt | att | 1344 |
|---|---|---|---|---|---|---|---|---|---|---|---|---|---|---|---|---|
| Thr | Ile | Leu | Thr | Tyr | Gly | Leu | Ala | Phe | Gln | Met | Val | Cys | Leu | Phe | Ile |
| 435 |  |  |  | 440 |  |  |  | 445 |  |  |  |  |  |  |  |

| att | ggt | gga | atg | ggt | ttt | ggt | tct | gga | agc | agc | gct | agt | aat | ggt | gcc | 1392 |
|---|---|---|---|---|---|---|---|---|---|---|---|---|---|---|---|---|
| Ile | Gly | Gly | Met | Gly | Phe | Gly | Ser | Gly | Ser | Ser | Ala | Ser | Asn | Gly | Ala |
|  |  | 450 |  |  |  | 455 |  |  |  | 460 |  |  |  |  |  |

| ggt | ggt | tta | ttg | ctg | gct | tta | tca | ttc | ttt | tac | aat | gct | ggt | atc | ggt | 1440 |
|---|---|---|---|---|---|---|---|---|---|---|---|---|---|---|---|---|
| Gly | Gly | Leu | Leu | Leu | Ala | Leu | Ser | Phe | Phe | Tyr | Asn | Ala | Gly | Ile | Gly |
| 465 |  |  |  | 470 |  |  |  | 475 |  |  |  | 480 |  |  |  |

| gca | gtt | gtt | tac | tgt | atc | gtt | gct | gaa | att | cca | tca | gcg | gag | ttg | aga | 1488 |
|---|---|---|---|---|---|---|---|---|---|---|---|---|---|---|---|---|
| Ala | Val | Val | Tyr | Cys | Ile | Val | Ala | Glu | Ile | Pro | Ser | Ala | Glu | Leu | Arg |
|  |  |  | 485 |  |  |  | 490 |  |  |  | 495 |  |  |  |  |

| act | aag | act | ata | gtg | ctg | gcc | cgt | att | tgc | tac | aat | ctc | atg | gcc | gtt | 1536 |
|---|---|---|---|---|---|---|---|---|---|---|---|---|---|---|---|---|
| Thr | Lys | Thr | Ile | Val | Leu | Ala | Arg | Ile | Cys | Tyr | Asn | Leu | Met | Ala | Val |
|  |  | 500 |  |  |  | 505 |  |  |  | 510 |  |  |  |  |  |

| att | aac | gct | ata | tta | acg | ccc | tat | atg | cta | aac | gtg | agc | gat | tgg | aac | 1584 |
|---|---|---|---|---|---|---|---|---|---|---|---|---|---|---|---|---|
| Ile | Asn | Ala | Ile | Leu | Thr | Pro | Tyr | Met | Leu | Asn | Val | Ser | Asp | Trp | Asn |
|  | 515 |  |  |  | 520 |  |  |  | 525 |  |  |  |  |  |  |

| tgg | ggt | gcc | aaa | act | ggt | cta | tac | tgg | ggt | ggt | ttc | aca | gca | gtc | act | 1632 |
|---|---|---|---|---|---|---|---|---|---|---|---|---|---|---|---|---|
| Trp | Gly | Ala | Lys | Thr | Gly | Leu | Tyr | Trp | Gly | Gly | Phe | Thr | Ala | Val | Thr |

-continued

```
          530                 535                 540
tta gct tgg gtc atc atc gat ctg cct gag aca act ggt aga acc ttc    1680
Leu Ala Trp Val Ile Ile Asp Leu Pro Glu Thr Thr Gly Arg Thr Phe
545                 550                 555                 560 agt gaa att aat gaa ctt ttc aac caa ggg gtt cct gcc aga aaa ttt    1728
Ser Glu Ile Asn Glu Leu Phe Asn Gln Gly Val Pro Ala Arg Lys Phe
                565                 570                 575 gca tct act gtg gtt gat cca ttc gga aag gga aaa act caa cat gat    1776
Ala Ser Thr Val Val Asp Pro Phe Gly Lys Gly Lys Thr Gln His Asp
            580                 585                 590 tcg cta gct gat gag agt atc agt cag tcc tca agc ata aaa cag cga    1824
Ser Leu Ala Asp Glu Ser Ile Ser Gln Ser Ser Ser Ile Lys Gln Arg
        595                 600                 605 gaa tta aat gca gct gat aaa tgt                                    1848
Glu Leu Asn Ala Ala Asp Lys Cys
    610             615

<210> SEQ ID NO 4
<211> LENGTH: 616
<212> TYPE: PRT
<213> ORGANISM: Saccharomyces cerevisiae

<400> SEQUENCE: 4

Met Lys Asn Ile Ile Ser Leu Val Ser Lys Lys Ala Ala Ser Lys
1               5                   10                  15

Asn Glu Asp Lys Asn Ile Ser Glu Ser Ser Arg Asp Ile Val Asn Gln
            20                  25                  30

Gln Glu Val Phe Asn Thr Glu Asp Phe Glu Gly Lys Lys Asp Ser
        35                  40                  45

Ala Phe Glu Leu Asp His Leu Glu Phe Thr Thr Asn Ser Ala Gln Leu
    50                  55                  60

Gly Asp Ser Asp Glu Asp Asn Glu Asn Val Ile Asn Glu Met Asn Ala
65                  70                  75                  80

Thr Asp Asp Ala Asn Glu Ala Asn Ser Glu Glu Lys Ser Met Thr Leu
                85                  90                  95

Lys Gln Ala Leu Leu Lys Tyr Pro Lys Ala Ala Leu Trp Ser Ile Leu
            100                 105                 110

Val Ser Thr Thr Leu Val Met Glu Gly Tyr Asp Thr Ala Leu Leu Ser
        115                 120                 125

Ala Leu Tyr Ala Leu Pro Val Phe Gln Arg Lys Phe Gly Thr Leu Asn
    130                 135                 140

Gly Glu Gly Ser Tyr Glu Ile Thr Ser Gln Trp Gln Ile Gly Leu Asn
145                 150                 155                 160

Met Cys Val Leu Cys Gly Glu Met Ile Gly Leu Gln Ile Thr Thr Tyr
                165                 170                 175

Met Val Glu Phe Met Gly Asn Arg Tyr Thr Met Ile Thr Ala Leu Gly
            180                 185                 190

Leu Leu Thr Ala Tyr Ile Phe Ile Leu Tyr Tyr Cys Lys Ser Leu Ala
        195                 200                 205

Met Ile Ala Val Gly Gln Ile Leu Ser Ala Ile Pro Trp Gly Cys Phe
    210                 215                 220

Gln Ser Leu Ala Val Thr Tyr Ala Ser Glu Val Cys Pro Leu Ala Leu
225                 230                 235                 240

Arg Tyr Tyr Met Thr Ser Tyr Ser Asn Ile Cys Trp Leu Phe Gly Gln
                245                 250                 255

Ile Phe Ala Ser Gly Ile Met Lys Asn Ser Gln Glu Asn Leu Gly Asn
            260                 265                 270
```

```
Ser Asp Leu Gly Tyr Lys Leu Pro Phe Ala Leu Gln Trp Ile Trp Pro
        275                 280                 285

Ala Pro Leu Met Ile Gly Ile Phe Phe Ala Pro Glu Ser Pro Trp Trp
        290                 295                 300

Leu Val Arg Lys Asp Arg Val Ala Glu Ala Arg Lys Ser Leu Ser Arg
305                 310                 315                 320

Ile Leu Ser Gly Lys Gly Ala Glu Lys Asp Ile Gln Val Asp Leu Thr
                325                 330                 335

Leu Lys Gln Ile Glu Leu Thr Ile Glu Lys Glu Arg Leu Leu Ala Ser
            340                 345                 350

Lys Ser Gly Ser Phe Phe Asn Cys Phe Lys Gly Val Asn Gly Arg Arg
        355                 360                 365

Thr Arg Leu Ala Cys Leu Thr Trp Val Ala Gln Asn Ser Ser Gly Ala
        370                 375                 380

Val Leu Leu Gly Tyr Ser Thr Tyr Phe Phe Glu Arg Ala Gly Met Ala
385                 390                 395                 400

Thr Asp Lys Ala Phe Thr Phe Ser Leu Ile Gln Tyr Cys Leu Gly Leu
                405                 410                 415

Ala Gly Thr Leu Cys Ser Trp Val Ile Ser Gly Arg Val Gly Arg Trp
            420                 425                 430

Thr Ile Leu Thr Tyr Gly Leu Ala Phe Gln Met Val Cys Leu Phe Ile
        435                 440                 445

Ile Gly Gly Met Gly Phe Gly Ser Gly Ser Ala Ser Asn Gly Ala
        450                 455                 460

Gly Gly Leu Leu Leu Ala Leu Ser Phe Phe Tyr Asn Ala Gly Ile Gly
465                 470                 475                 480

Ala Val Val Tyr Cys Ile Val Ala Glu Ile Pro Ser Ala Glu Leu Arg
                485                 490                 495

Thr Lys Thr Ile Val Leu Ala Arg Ile Cys Tyr Asn Leu Met Ala Val
            500                 505                 510

Ile Asn Ala Ile Leu Thr Pro Tyr Met Leu Asn Val Ser Asp Trp Asn
        515                 520                 525

Trp Gly Ala Lys Thr Gly Leu Tyr Trp Gly Gly Phe Thr Ala Val Thr
        530                 535                 540

Leu Ala Trp Val Ile Ile Asp Leu Pro Glu Thr Thr Gly Arg Thr Phe
545                 550                 555                 560

Ser Glu Ile Asn Glu Leu Phe Asn Gln Gly Val Pro Ala Arg Lys Phe
                565                 570                 575

Ala Ser Thr Val Val Asp Pro Phe Gly Lys Gly Lys Thr Gln His Asp
            580                 585                 590

Ser Leu Ala Asp Glu Ser Ile Ser Gln Ser Ser Ile Lys Gln Arg
        595                 600                 605

Glu Leu Asn Ala Ala Asp Lys Cys
    610                 615

<210> SEQ ID NO 5
<211> LENGTH: 1845
<212> TYPE: DNA
<213> ORGANISM: Saccharomyces cerevisiae
<220> FEATURE:
<221> NAME/KEY: CDS
<222> LOCATION: (1)..(1845)
<223> OTHER INFORMATION: Mtt1p

<400> SEQUENCE: 5 atg aag gga tta tcc tca tta ata aac aga aaa aaa gac agg aac gac     48
```

|  |  |
|---|---|
| Met Lys Gly Leu Ser Ser Leu Ile Asn Arg Lys Lys Asp Arg Asn Asp<br>1               5                   10                  15 | |
| tca cac tta gat gag atc gag aat ggc gtg aac gct acc gaa ttc aac<br>Ser His Leu Asp Glu Ile Glu Asn Gly Val Asn Ala Thr Glu Phe Asn<br>            20                  25                  30 | 96 |
| tcg ata gag atg gag gag caa ggt aag aaa agt gat ttt gat ctt tcc<br>Ser Ile Glu Met Glu Glu Gln Gly Lys Lys Ser Asp Phe Asp Leu Ser<br>        35                  40                  45 | 144 |
| cat cat gag tac ggt cca ggt tca cta aca cca aac gat aat aat gaa<br>His His Glu Tyr Gly Pro Gly Ser Leu Thr Pro Asn Asp Asn Asn Glu<br>    50                  55                  60 | 192 |
| gaa gtc ccc gac ctt ctc gat gaa gct atg cag gac gcc aaa gag gca<br>Glu Val Pro Asp Leu Leu Asp Glu Ala Met Gln Asp Ala Lys Glu Ala<br>65                  70                  75                  80 | 240 |
| gat gaa agt gag agg gga atg cca ctc atg aca gct ttg aag aca tat<br>Asp Glu Ser Glu Arg Gly Met Pro Leu Met Thr Ala Leu Lys Thr Tyr<br>                85                  90                  95 | 288 |
| cca aaa gct gct gct tgg tca cta tta gtt tcc aca aca ttg att caa<br>Pro Lys Ala Ala Ala Trp Ser Leu Leu Val Ser Thr Thr Leu Ile Gln<br>            100                 105                 110 | 336 |
| gag ggt tat gac aca gcc att cta gga tct ttc tat gcc ctg cct gtt<br>Glu Gly Tyr Asp Thr Ala Ile Leu Gly Ser Phe Tyr Ala Leu Pro Val<br>        115                 120                 125 | 384 |
| ttt caa aaa aaa tat ggt tct ttg aat agc aat aca gga gat tat gaa<br>Phe Gln Lys Lys Tyr Gly Ser Leu Asn Ser Asn Thr Gly Asp Tyr Glu<br>    130                 135                 140 | 432 |
| att tca gct tcc tgg caa att ggc ttg tcc tta tgc gtt acg gct ggt<br>Ile Ser Ala Ser Trp Gln Ile Gly Leu Ser Leu Cys Val Thr Ala Gly<br>145                 150                 155                 160 | 480 |
| gaa att gta ggt ttg caa atg act ggg cct ttt gta gat tat atg ggt<br>Glu Ile Val Gly Leu Gln Met Thr Gly Pro Phe Val Asp Tyr Met Gly<br>                165                 170                 175 | 528 |
| aat cgc tat aca ttg att ttg gca ttg att ctt ctt gct gca ttc acc<br>Asn Arg Tyr Thr Leu Ile Leu Ala Leu Ile Leu Leu Ala Ala Phe Thr<br>            180                 185                 190 | 576 |
| ttt att ctg tat ttt tgc aag ggt ttg ggt atg att gct gtg gga caa<br>Phe Ile Leu Tyr Phe Cys Lys Gly Leu Gly Met Ile Ala Val Gly Gln<br>        195                 200                 205 | 624 |
| gta ttg tgt ggt atg cca tgg ggt tgt ttc caa tgt ttg acc gtt tct<br>Val Leu Cys Gly Met Pro Trp Gly Cys Phe Gln Cys Leu Thr Val Ser<br>    210                 215                 220 | 672 |
| tat gct tct gaa att tgt cct atg gcc cta aga tac tat ttg acg act<br>Tyr Ala Ser Glu Ile Cys Pro Met Ala Leu Arg Tyr Tyr Leu Thr Thr<br>225                 230                 235                 240 | 720 |
| tat tct aat tta tgt tgg acg ttc ggt caa ctt ttc gct gct ggt att<br>Tyr Ser Asn Leu Cys Trp Thr Phe Gly Gln Leu Phe Ala Ala Gly Ile<br>                245                 250                 255 | 768 |
| atg aaa aac tcc caa aat aag tac cct aac tca gaa cta gga tat aag<br>Met Lys Asn Ser Gln Asn Lys Tyr Pro Asn Ser Glu Leu Gly Tyr Lys<br>            260                 265                 270 | 816 |
| cta cct ttt gct ttg cag tgg atc tgg cct gct cct ctt gca ata ggt<br>Leu Pro Phe Ala Leu Gln Trp Ile Trp Pro Ala Pro Leu Ala Ile Gly<br>        275                 280                 285 | 864 |
| att ttt ttt gca cca gag tct cca tgg tgg ctg gtt aaa aaa gga agg<br>Ile Phe Phe Ala Pro Glu Ser Pro Trp Trp Leu Val Lys Lys Gly Arg<br>    290                 295                 300 | 912 |
| att gat caa gca agg aga tca ctt gaa aga aca ttg agt ggt aaa gga<br>Ile Asp Gln Ala Arg Arg Ser Leu Glu Arg Thr Leu Ser Gly Lys Gly<br>305                 310                 315                 320 | 960 |
| ccc gag aag gaa tta ctg gta agt atg gag cta gat aat atc aaa gta | 1008 |

```
                Pro Glu Lys Glu Leu Leu Val Ser Met Glu Leu Asp Asn Ile Lys Val
                                325                 330                 335 acc att gaa aag gaa aaa aag ctg tca gac tca gaa ggt tcc tat tgg            1056
Thr Ile Glu Lys Glu Lys Lys Leu Ser Asp Ser Glu Gly Ser Tyr Trp
            340                 345                 350 gat tgt ctg aag gac agt gtt aat agg aga aga acg aga ata gct tgt            1104
Asp Cys Leu Lys Asp Ser Val Asn Arg Arg Arg Thr Arg Ile Ala Cys
        355                 360                 365 tta tgt tgg gtc ggt caa acc acc tgt ggt aca tca tta att ggt aat            1152
Leu Cys Trp Val Gly Gln Thr Thr Cys Gly Thr Ser Leu Ile Gly Asn
    370                 375                 380 tca act tac ttt tat gaa aaa gct gga gtt ggt act gat acg gct ttc            1200
Ser Thr Tyr Phe Tyr Glu Lys Ala Gly Val Gly Thr Asp Thr Ala Phe
385                 390                 395                 400 act ttc agt att atc caa tat tgt ctt ggt att gcc gca aca ttt ctt            1248
Thr Phe Ser Ile Ile Gln Tyr Cys Leu Gly Ile Ala Ala Thr Phe Leu
                405                 410                 415 tct tgg tgg gct tca aaa tat ttt ggt agg ttt gac ctt tac gca ttt            1296
Ser Trp Trp Ala Ser Lys Tyr Phe Gly Arg Phe Asp Leu Tyr Ala Phe
            420                 425                 430 gga ttg gct ata caa aca gtt tca ttg ttt atc ata gga ggt ttg gga            1344
Gly Leu Ala Ile Gln Thr Val Ser Leu Phe Ile Ile Gly Gly Leu Gly
        435                 440                 445 tgc tcc gac tcg cat ggc gct gaa atg gga agt ggt tct ctt tta atg            1392
Cys Ser Asp Ser His Gly Ala Glu Met Gly Ser Gly Ser Leu Leu Met
    450                 455                 460 gtt ctt tcc ttc ttc tac aat ttg ggt att gct ccc gtt gtg ttt tgc            1440
Val Leu Ser Phe Phe Tyr Asn Leu Gly Ile Ala Pro Val Val Phe Cys
465                 470                 475                 480 tta gtg tcc gaa ata cca tcc tca agg cta aga act aaa tcg att att            1488
Leu Val Ser Glu Ile Pro Ser Ser Arg Leu Arg Thr Lys Ser Ile Ile
                485                 490                 495 ctg gct cgt aac gca tat aat atg gca tct att gta act act gtt ttg            1536
Leu Ala Arg Asn Ala Tyr Asn Met Ala Ser Ile Val Thr Thr Val Leu
            500                 505                 510 atc atg tac caa ttg aac tca gaa aaa tgg aac tgg ggt gcc aag tcg            1584
Ile Met Tyr Gln Leu Asn Ser Glu Lys Trp Asn Trp Gly Ala Lys Ser
        515                 520                 525 ggc ttt ttc tgg gga ggg tta tgt ttt gcc act cta gtt tgg gcc gta            1632
Gly Phe Phe Trp Gly Gly Leu Cys Phe Ala Thr Leu Val Trp Ala Val
    530                 535                 540 att gac cta cca gaa act gct ggc agg act ttt att gag ata aat gaa            1680
Ile Asp Leu Pro Glu Thr Ala Gly Arg Thr Phe Ile Glu Ile Asn Glu
545                 550                 555                 560 ttg ttt aga ctt ggt gtt cca gca aga aag ttc aag tcg act aaa gtc            1728
Leu Phe Arg Leu Gly Val Pro Ala Arg Lys Phe Lys Ser Thr Lys Val
                565                 570                 575 gac cct ttt gca gct gcc aaa gca gca gct gaa att aat gtt aaa            1776
Asp Pro Phe Ala Ala Ala Lys Ala Ala Ala Glu Ile Asn Val Lys
            580                 585                 590 gat ccg aag gaa gat ttg gaa act tct gtg gta gat gaa ggg cga agc            1824
Asp Pro Lys Glu Asp Leu Glu Thr Ser Val Val Asp Glu Gly Arg Ser
        595                 600                 605 acc cca tct gtt gtg aac aaa                                                1845
Thr Pro Ser Val Val Asn Lys
    610                 615

<210> SEQ ID NO 6
<211> LENGTH: 615
<212> TYPE: PRT
<213> ORGANISM: Saccharomyces cerevisiae
```

```
<400> SEQUENCE: 6

Met Lys Gly Leu Ser Ser Leu Ile Asn Arg Lys Asp Arg Asn Asp
1               5                   10                  15

Ser His Leu Asp Glu Ile Glu Asn Gly Val Asn Ala Thr Glu Phe Asn
                20                  25                  30

Ser Ile Glu Met Glu Glu Gln Gly Lys Lys Ser Asp Phe Asp Leu Ser
            35                  40                  45

His His Glu Tyr Gly Pro Gly Ser Leu Thr Pro Asn Asp Asn Asn Glu
50                  55                  60

Glu Val Pro Asp Leu Leu Asp Glu Ala Met Gln Asp Ala Lys Glu Ala
65                  70                  75                  80

Asp Glu Ser Glu Arg Gly Met Pro Leu Met Thr Ala Leu Lys Thr Tyr
                85                  90                  95

Pro Lys Ala Ala Ala Trp Ser Leu Leu Val Ser Thr Thr Leu Ile Gln
                100                 105                 110

Glu Gly Tyr Asp Thr Ala Ile Leu Gly Ser Phe Tyr Ala Leu Pro Val
            115                 120                 125

Phe Gln Lys Lys Tyr Gly Ser Leu Asn Ser Asn Thr Gly Asp Tyr Glu
130                 135                 140

Ile Ser Ala Ser Trp Gln Ile Gly Leu Ser Leu Cys Val Thr Ala Gly
145                 150                 155                 160

Glu Ile Val Gly Leu Gln Met Thr Gly Pro Phe Val Asp Tyr Met Gly
                165                 170                 175

Asn Arg Tyr Thr Leu Ile Leu Ala Leu Ile Leu Ala Ala Phe Thr
            180                 185                 190

Phe Ile Leu Tyr Phe Cys Lys Gly Leu Gly Met Ile Ala Val Gly Gln
            195                 200                 205

Val Leu Cys Gly Met Pro Trp Gly Cys Phe Gln Cys Leu Thr Val Ser
                210                 215                 220

Tyr Ala Ser Glu Ile Cys Pro Met Ala Leu Arg Tyr Tyr Leu Thr Thr
225                 230                 235                 240

Tyr Ser Asn Leu Cys Trp Thr Phe Gly Gln Leu Phe Ala Ala Gly Ile
            245                 250                 255

Met Lys Asn Ser Gln Asn Lys Tyr Pro Asn Ser Glu Leu Gly Tyr Lys
                260                 265                 270

Leu Pro Phe Ala Leu Gln Trp Ile Trp Pro Ala Pro Leu Ala Ile Gly
            275                 280                 285

Ile Phe Phe Ala Pro Glu Ser Pro Trp Trp Leu Val Lys Lys Gly Arg
290                 295                 300

Ile Asp Gln Ala Arg Arg Ser Leu Glu Arg Thr Leu Ser Gly Lys Gly
305                 310                 315                 320

Pro Glu Lys Glu Leu Leu Val Ser Met Glu Leu Asp Asn Ile Lys Val
                325                 330                 335

Thr Ile Glu Lys Glu Lys Leu Ser Asp Ser Glu Gly Ser Tyr Trp
            340                 345                 350

Asp Cys Leu Lys Asp Ser Val Asn Arg Arg Thr Arg Ile Ala Cys
            355                 360                 365

Leu Cys Trp Val Gly Gln Thr Thr Cys Gly Thr Ser Leu Ile Gly Asn
            370                 375                 380

Ser Thr Tyr Phe Tyr Glu Lys Ala Gly Val Gly Thr Asp Thr Ala Phe
385                 390                 395                 400

Thr Phe Ser Ile Ile Gln Tyr Cys Leu Gly Ile Ala Ala Thr Phe Leu
                405                 410                 415
```

```
Ser Trp Trp Ala Ser Lys Tyr Phe Gly Arg Phe Asp Leu Tyr Ala Phe
        420                 425                 430

Gly Leu Ala Ile Gln Thr Val Ser Leu Phe Ile Ile Gly Gly Leu Gly
            435                 440                 445

Cys Ser Asp Ser His Gly Ala Glu Met Gly Ser Gly Ser Leu Leu Met
450                 455                 460

Val Leu Ser Phe Phe Tyr Asn Leu Gly Ile Ala Pro Val Val Phe Cys
465                 470                 475                 480

Leu Val Ser Glu Ile Pro Ser Ser Arg Leu Arg Thr Lys Ser Ile Ile
                485                 490                 495

Leu Ala Arg Asn Ala Tyr Asn Met Ala Ser Ile Val Thr Thr Val Leu
                500                 505                 510

Ile Met Tyr Gln Leu Asn Ser Glu Lys Trp Asn Trp Gly Ala Lys Ser
            515                 520                 525

Gly Phe Phe Trp Gly Leu Cys Phe Ala Thr Leu Val Trp Ala Val
        530                 535                 540

Ile Asp Leu Pro Glu Thr Ala Gly Arg Thr Phe Ile Glu Ile Asn Glu
545                 550                 555                 560

Leu Phe Arg Leu Gly Val Pro Ala Arg Lys Phe Lys Ser Thr Lys Val
                565                 570                 575

Asp Pro Phe Ala Ala Lys Ala Ala Ala Glu Ile Asn Val Lys
                580                 585                 590

Asp Pro Lys Glu Asp Leu Glu Thr Ser Val Val Asp Glu Gly Arg Ser
                595                 600                 605

Thr Pro Ser Val Val Asn Lys
        610                 615

<210> SEQ ID NO 7
<211> LENGTH: 1860
<212> TYPE: DNA
<213> ORGANISM: Artificial Sequence
<220> FEATURE:
<223> OTHER INFORMATION: Description of Artificial Sequence: Synthetic
      AAM polynucleotide
<220> FEATURE:
<221> NAME/KEY: CDS
<222> LOCATION: (1)..(1860)
<223> OTHER INFORMATION: AAMp

<400> SEQUENCE: 7 atg aaa aat atc att tca ttg gta agc aag aag aag gct gcc tca aaa      48
Met Lys Asn Ile Ile Ser Leu Val Ser Lys Lys Lys Ala Ala Ser Lys
1               5                   10                  15 aat gag gat aaa aac att tct gag tct tca aga gat att gta aac caa      96
Asn Glu Asp Lys Asn Ile Ser Glu Ser Ser Arg Asp Ile Val Asn Gln
            20                  25                  30 cag gag gtt ttc aat act gaa gat ttt gaa gaa ggg aaa aag gat agt      144
Gln Glu Val Phe Asn Thr Glu Asp Phe Glu Glu Gly Lys Lys Asp Ser
        35                  40                  45 gcc ttt gag cta gac cac tta gag ttc acc acc aat tca gcc cag tta      192
Ala Phe Glu Leu Asp His Leu Glu Phe Thr Thr Asn Ser Ala Gln Leu
    50                  55                  60 gga gat tct gac gaa gat aac gag aat gtg att aat gag atg aac gct      240
Gly Asp Ser Asp Glu Asp Asn Glu Asn Val Ile Asn Glu Met Asn Ala
65                  70                  75                  80 act gat gat gca aat gaa gct aac agc gag gaa aaa agc atg act ttg      288
Thr Asp Asp Ala Asn Glu Ala Asn Ser Glu Glu Lys Ser Met Thr Leu
                85                  90                  95 aag cag gcg ttg cta aaa tat cca aaa gca gcc ctg tgg tcc ata tta      336
```

-continued

| | | | | | | | | | | | | | | | |
|---|---|---|---|---|---|---|---|---|---|---|---|---|---|---|---|
| Lys | Gln | Ala | Leu | Leu | Lys | Tyr | Pro | Lys | Ala | Ala | Leu | Trp | Ser | Ile | Leu |
| | | | 100 | | | | 105 | | | | 110 | | | | |

| gtg | tct | act | acc | ctg | gtt | atg | gaa | ggt | tat | gat | acc | gca | cta | ctg | agc | 384 |
|---|---|---|---|---|---|---|---|---|---|---|---|---|---|---|---|---|
| Val | Ser | Thr | Thr | Leu | Val | Met | Glu | Gly | Tyr | Asp | Thr | Ala | Leu | Leu | Ser | |
| | | 115 | | | | 120 | | | | 125 | | | | | | |

| gca | ctg | tat | gcc | ctg | cca | gtt | ttt | cag | aga | aaa | ttc | ggt | act | ttg | aac | 432 |
|---|---|---|---|---|---|---|---|---|---|---|---|---|---|---|---|---|
| Ala | Leu | Tyr | Ala | Leu | Pro | Val | Phe | Gln | Arg | Lys | Phe | Gly | Thr | Leu | Asn | |
| | 130 | | | | 135 | | | | 140 | | | | | | | |

| ggg | gag | ggt | tct | tac | gaa | att | act | tcc | caa | tgg | cag | att | ggt | tta | aac | 480 |
|---|---|---|---|---|---|---|---|---|---|---|---|---|---|---|---|---|
| Gly | Glu | Gly | Ser | Tyr | Glu | Ile | Thr | Ser | Gln | Trp | Gln | Ile | Gly | Leu | Asn | |
| 145 | | | | 150 | | | | 155 | | | | 160 | | | | |

| atg | tgt | gtc | ctt | tgt | ggt | gag | atg | att | ggt | ttg | caa | atc | acg | act | tat | 528 |
|---|---|---|---|---|---|---|---|---|---|---|---|---|---|---|---|---|
| Met | Cys | Val | Leu | Cys | Gly | Glu | Met | Ile | Gly | Leu | Gln | Ile | Thr | Thr | Tyr | |
| | | | 165 | | | | 170 | | | | 175 | | | | | |

| atg | gtt | gaa | ttt | atg | ggg | aat | cgt | tat | acg | atg | att | aca | gca | ctt | ggt | 576 |
|---|---|---|---|---|---|---|---|---|---|---|---|---|---|---|---|---|
| Met | Val | Glu | Phe | Met | Gly | Asn | Arg | Tyr | Thr | Met | Ile | Thr | Ala | Leu | Gly | |
| | 180 | | | | 185 | | | | 190 | | | | | | | |

| tta | act | gct | tat | atc | ttt | atc | ctc | tac | tac | tgt | aaa | agt | tta | gct | | 624 |
|---|---|---|---|---|---|---|---|---|---|---|---|---|---|---|---|---|
| Leu | Leu | Thr | Ala | Tyr | Ile | Phe | Ile | Leu | Tyr | Tyr | Cys | Lys | Ser | Leu | Ala | |
| 195 | | | | 200 | | | | 205 | | | | | | | | |

| atg | att | gct | gtg | gga | caa | att | ctc | tca | gct | ata | cca | tgg | ggt | tgt | ttc | 672 |
|---|---|---|---|---|---|---|---|---|---|---|---|---|---|---|---|---|
| Met | Ile | Ala | Val | Gly | Gln | Ile | Leu | Ser | Ala | Ile | Pro | Trp | Gly | Cys | Phe | |
| 210 | | | | 215 | | | | 220 | | | | | | | | |

| caa | agt | ttg | gct | gtt | act | tat | gct | tcg | gaa | gtt | tgc | cct | tta | gca | tta | 720 |
|---|---|---|---|---|---|---|---|---|---|---|---|---|---|---|---|---|
| Gln | Ser | Leu | Ala | Val | Thr | Tyr | Ala | Ser | Glu | Val | Cys | Pro | Leu | Ala | Leu | |
| 225 | | | | 230 | | | | 235 | | | | 240 | | | | |

| aga | tat | tac | atg | acc | agt | tac | tcc | aac | att | tgt | tgg | tta | ttt | ggt | caa | 768 |
|---|---|---|---|---|---|---|---|---|---|---|---|---|---|---|---|---|
| Arg | Tyr | Tyr | Met | Thr | Ser | Tyr | Ser | Asn | Ile | Cys | Trp | Leu | Phe | Gly | Gln | |
| | | | 245 | | | | 250 | | | | 255 | | | | | |

| atc | ttc | gcc | tct | ggt | att | atg | aaa | aac | tca | caa | gag | aat | tta | ggg | aac | 816 |
|---|---|---|---|---|---|---|---|---|---|---|---|---|---|---|---|---|
| Ile | Phe | Ala | Ser | Gly | Ile | Met | Lys | Asn | Ser | Gln | Glu | Asn | Leu | Gly | Asn | |
| | | 260 | | | | 265 | | | | 270 | | | | | | |

| tcc | gac | ttg | ggc | tat | aaa | ttg | cca | ttt | gct | tta | caa | tgg | att | tgg | cct | 864 |
|---|---|---|---|---|---|---|---|---|---|---|---|---|---|---|---|---|
| Ser | Asp | Leu | Gly | Tyr | Lys | Leu | Pro | Phe | Ala | Leu | Gln | Trp | Ile | Trp | Pro | |
| | 275 | | | | 280 | | | | 285 | | | | | | | |

| gct | cct | tta | atg | atc | ggt | atc | ttt | ttc | gct | cct | gag | tcg | ccc | tgg | tgg | 912 |
|---|---|---|---|---|---|---|---|---|---|---|---|---|---|---|---|---|
| Ala | Pro | Leu | Met | Ile | Gly | Ile | Phe | Phe | Ala | Pro | Glu | Ser | Pro | Trp | Trp | |
| 290 | | | | 295 | | | | 300 | | | | | | | | |

| ttg | gtg | aga | aag | gat | agg | gtc | gct | gag | gca | aga | aaa | tct | tta | agc | aga | 960 |
|---|---|---|---|---|---|---|---|---|---|---|---|---|---|---|---|---|
| Leu | Val | Arg | Lys | Asp | Arg | Val | Ala | Glu | Ala | Arg | Lys | Ser | Leu | Ser | Arg | |
| 305 | | | | 310 | | | | 315 | | | | 320 | | | | |

| att | ttg | agt | ggt | aaa | ggc | gcc | gag | aag | gac | att | caa | gtt | gat | ctt | act | 1008 |
|---|---|---|---|---|---|---|---|---|---|---|---|---|---|---|---|---|
| Ile | Leu | Ser | Gly | Lys | Gly | Ala | Glu | Lys | Asp | Ile | Gln | Val | Asp | Leu | Thr | |
| | | | 325 | | | | 330 | | | | 335 | | | | | |

| tta | aag | cag | att | gaa | ttg | act | att | gaa | aaa | gaa | aga | ctt | tta | gca | tct | 1056 |
|---|---|---|---|---|---|---|---|---|---|---|---|---|---|---|---|---|
| Leu | Lys | Gln | Ile | Glu | Leu | Thr | Ile | Glu | Lys | Glu | Arg | Leu | Leu | Ala | Ser | |
| | | 340 | | | | 345 | | | | 350 | | | | | | |

| aaa | tca | gga | tca | ttc | ttt | aat | tgt | ttc | aag | gga | gtt | aat | gga | aga | aga | 1104 |
|---|---|---|---|---|---|---|---|---|---|---|---|---|---|---|---|---|
| Lys | Ser | Gly | Ser | Phe | Phe | Asn | Cys | Phe | Lys | Gly | Val | Asn | Gly | Arg | Arg | |
| | 355 | | | | 360 | | | | 365 | | | | | | | |

| acg | aga | ctt | gca | tgt | tta | act | tgg | gta | gct | caa | aat | agt | agc | ggt | gcc | 1152 |
|---|---|---|---|---|---|---|---|---|---|---|---|---|---|---|---|---|
| Thr | Arg | Leu | Ala | Cys | Leu | Thr | Trp | Val | Ala | Gln | Asn | Ser | Ser | Gly | Ala | |
| 370 | | | | 375 | | | | 380 | | | | | | | | |

| gtt | tta | ctt | ggt | tac | tcg | aca | tat | ttt | ttt | gaa | aga | gca | ggt | atg | gcc | 1200 |
|---|---|---|---|---|---|---|---|---|---|---|---|---|---|---|---|---|
| Val | Leu | Leu | Gly | Tyr | Ser | Thr | Tyr | Phe | Phe | Glu | Arg | Ala | Gly | Met | Ala | |
| 385 | | | | 390 | | | | 395 | | | | 400 | | | | |

| acc | gac | aag | gcg | ttt | act | ttt | tct | cta | att | cag | tac | tgt | ctt | ggg | tta | 1248 |
|---|---|---|---|---|---|---|---|---|---|---|---|---|---|---|---|---|
| Thr | Asp | Lys | Ala | Phe | Thr | Phe | Ser | Leu | Ile | Gln | Tyr | Cys | Leu | Gly | Leu | |
| | | | 405 | | | | 410 | | | | 415 | | | | | |

| gcg | ggt | aca | ctt | tgc | tcc | tgg | gta | ata | tct | ggc | cgt | gtt | ggt | aga | tgg | 1296 |

-continued

```
            Ala Gly Thr Leu Cys Ser Trp Val Ile Ser Gly Arg Val Gly Arg Trp
                420                 425                 430 aca ata ctg acc tat ggt ctt gca ttt caa atg gtc tgc tta ttt att       1344
Thr Ile Leu Thr Tyr Gly Leu Ala Phe Gln Met Val Cys Leu Phe Ile
        435                 440                 445 att ggt gga atg ggt ttt ggt tct gga agc agc gct agt aat ggt gcc       1392
Ile Gly Gly Met Gly Phe Gly Ser Gly Ser Ser Ala Ser Asn Gly Ala
    450                 455                 460 ggt ggt tta ttg ctg gct tta tca ttc ttt tac aat gct ggt atc ggt       1440
Gly Gly Leu Leu Leu Ala Leu Ser Phe Phe Tyr Asn Ala Gly Ile Gly
465                 470                 475                 480 gca gtt gtt tac tgt atc gtt gct gaa att cca tca gcg gag ttg aga       1488
Ala Val Val Tyr Cys Ile Val Ala Glu Ile Pro Ser Ala Glu Leu Arg
                485                 490                 495 act aag act ata gtg ctg gcc cgt att tgc tac aat ctc atg gcc gtt       1536
Thr Lys Thr Ile Val Leu Ala Arg Ile Cys Tyr Asn Leu Met Ala Val
        500                 505                 510 att aac gct ata tta acg ccc tat atg cta aac gtg agc gat tgg aac       1584
Ile Asn Ala Ile Leu Thr Pro Tyr Met Leu Asn Val Ser Asp Trp Asn
    515                 520                 525 tgg ggt gcc aaa act ggt cta tac tgg ggt ggt ttc aca gca gtc act       1632
Trp Gly Ala Lys Thr Gly Leu Tyr Trp Gly Gly Phe Thr Ala Val Thr
530                 535                 540 tta gct tgg gtc atc atc gat ctg cct gag aca act ggt aga acc ttc       1680
Leu Ala Trp Val Ile Ile Asp Leu Pro Glu Thr Thr Gly Arg Thr Phe
545                 550                 555                 560 agt gaa att aat gaa ctt ttc aac caa ggg gta cca gca aga aag ttc       1728
Ser Glu Ile Asn Glu Leu Phe Asn Gln Gly Val Pro Ala Arg Lys Phe
                565                 570                 575 aag tcg act aaa gtc gac cct ttt gca gct gcc aaa gca gca gct gca       1776
Lys Ser Thr Lys Val Asp Pro Phe Ala Ala Ala Lys Ala Ala Ala Ala
        580                 585                 590 gaa att aat gtt aaa gat ccg aag gaa gat ttg gaa act tct gtg gta       1824
Glu Ile Asn Val Lys Asp Pro Lys Glu Asp Leu Glu Thr Ser Val Val
    595                 600                 605 gat gaa ggg cga aac acc tca tct gtt gtg aac aaa                       1860
Asp Glu Gly Arg Asn Thr Ser Ser Val Val Asn Lys
610                 615                 620

<210> SEQ ID NO 8
<211> LENGTH: 620
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Lys Asn Ile Ile Ser Leu Val Ser Lys Lys Ala Ala Ser Lys
1               5                   10                  15

Asn Glu Asp Lys Asn Ile Ser Glu Ser Ser Arg Asp Ile Val Asn Gln
            20                  25                  30

Gln Glu Val Phe Asn Thr Glu Asp Phe Glu Glu Gly Lys Lys Asp Ser
        35                  40                  45

Ala Phe Glu Leu Asp His Leu Glu Phe Thr Thr Asn Ser Ala Gln Leu
    50                  55                  60

Gly Asp Ser Asp Glu Asn Glu Asn Val Ile Asn Glu Met Asn Ala
65                  70                  75                  80

Thr Asp Asp Ala Asn Glu Ala Asn Ser Glu Glu Lys Ser Met Thr Leu
                85                  90                  95
```

```
Lys Gln Ala Leu Leu Lys Tyr Pro Lys Ala Ala Leu Trp Ser Ile Leu
                100                 105                 110

Val Ser Thr Thr Leu Val Met Glu Gly Tyr Asp Thr Ala Leu Leu Ser
            115                 120                 125

Ala Leu Tyr Ala Leu Pro Val Phe Gln Arg Lys Phe Gly Thr Leu Asn
        130                 135                 140

Gly Glu Gly Ser Tyr Glu Ile Thr Ser Gln Trp Gln Ile Gly Leu Asn
145                 150                 155                 160

Met Cys Val Leu Cys Gly Glu Met Ile Gly Leu Gln Ile Thr Thr Tyr
                165                 170                 175

Met Val Glu Phe Met Gly Asn Arg Tyr Thr Met Ile Thr Ala Leu Gly
            180                 185                 190

Leu Leu Thr Ala Tyr Ile Phe Ile Leu Tyr Tyr Cys Lys Ser Leu Ala
        195                 200                 205

Met Ile Ala Val Gly Gln Ile Leu Ser Ala Ile Pro Trp Gly Cys Phe
210                 215                 220

Gln Ser Leu Ala Val Thr Tyr Ala Ser Glu Val Cys Pro Leu Ala Leu
225                 230                 235                 240

Arg Tyr Tyr Met Thr Ser Tyr Ser Asn Ile Cys Trp Leu Phe Gly Gln
                245                 250                 255

Ile Phe Ala Ser Gly Ile Met Lys Asn Ser Gln Glu Asn Leu Gly Asn
            260                 265                 270

Ser Asp Leu Gly Tyr Lys Leu Pro Phe Ala Leu Gln Trp Ile Trp Pro
        275                 280                 285

Ala Pro Leu Met Ile Gly Ile Phe Phe Ala Pro Glu Ser Pro Trp Trp
290                 295                 300

Leu Val Arg Lys Asp Arg Val Ala Glu Ala Arg Lys Ser Leu Ser Arg
305                 310                 315                 320

Ile Leu Ser Gly Lys Gly Ala Glu Lys Asp Ile Gln Val Asp Leu Thr
                325                 330                 335

Leu Lys Gln Ile Glu Leu Thr Ile Glu Lys Glu Arg Leu Leu Ala Ser
            340                 345                 350

Lys Ser Gly Ser Phe Phe Asn Cys Phe Lys Gly Val Asn Gly Arg Arg
        355                 360                 365

Thr Arg Leu Ala Cys Leu Thr Trp Val Ala Gln Asn Ser Ser Gly Ala
370                 375                 380

Val Leu Leu Gly Tyr Ser Thr Tyr Phe Phe Glu Arg Ala Gly Met Ala
385                 390                 395                 400

Thr Asp Lys Ala Phe Thr Phe Ser Leu Ile Gln Tyr Cys Leu Gly Leu
                405                 410                 415

Ala Gly Thr Leu Cys Ser Trp Val Ile Ser Gly Arg Val Gly Arg Trp
            420                 425                 430

Thr Ile Leu Thr Tyr Gly Leu Ala Phe Gln Met Val Cys Leu Phe Ile
        435                 440                 445

Ile Gly Gly Met Gly Phe Gly Ser Gly Ser Ala Ser Asn Gly Ala
450                 455                 460

Gly Gly Leu Leu Leu Ala Leu Ser Phe Phe Tyr Asn Ala Gly Ile Gly
465                 470                 475                 480

Ala Val Val Tyr Cys Ile Val Ala Glu Ile Pro Ser Ala Glu Leu Arg
                485                 490                 495

Thr Lys Thr Ile Val Leu Ala Arg Ile Cys Tyr Asn Leu Met Ala Val
            500                 505                 510

Ile Asn Ala Ile Leu Thr Pro Tyr Met Leu Asn Val Ser Asp Trp Asn
        515                 520                 525
```

```
Trp Gly Ala Lys Thr Gly Leu Tyr Trp Gly Gly Phe Thr Ala Val Thr
    530                 535                 540

Leu Ala Trp Val Ile Ile Asp Leu Pro Glu Thr Thr Gly Arg Thr Phe
545                 550                 555                 560

Ser Glu Ile Asn Glu Leu Phe Asn Gln Gly Val Pro Ala Arg Lys Phe
                565                 570                 575

Lys Ser Thr Lys Val Asp Pro Phe Ala Ala Lys Ala Ala Ala
            580                 585                 590

Glu Ile Asn Val Lys Asp Pro Lys Glu Asp Leu Glu Thr Ser Val Val
                595                 600                 605

Asp Glu Gly Arg Asn Thr Ser Ser Val Val Asn Lys
    610                 615                 620

<210> SEQ ID NO 9
<211> LENGTH: 1851
<212> TYPE: DNA
<213> ORGANISM: Artificial Sequence
<220> FEATURE:
<223> OTHER INFORMATION: Description of Artificial Sequence: Synthetic
      AMA polynucleotide
<220> FEATURE:
<221> NAME/KEY: CDS
<222> LOCATION: (1)..(1851)
<223> OTHER INFORMATION: AMAp

<400> SEQUENCE: 9 atg aaa aat atc att tca ttg gta agc aag aag aag gct gcc tca aaa      48
Met Lys Asn Ile Ile Ser Leu Val Ser Lys Lys Lys Ala Ala Ser Lys
1               5                   10                  15 aat gag gat aaa aac att tct gag tct tca aga gat att gta aac caa      96
Asn Glu Asp Lys Asn Ile Ser Glu Ser Ser Arg Asp Ile Val Asn Gln
            20                  25                  30 cag gag gtt ttc aat act gaa gat ttt gaa gaa ggg aaa aag gat agt     144
Gln Glu Val Phe Asn Thr Glu Asp Phe Glu Glu Gly Lys Lys Asp Ser
        35                  40                  45 gcc ttt gag cta gac cac tta gag ttc acc acc aat tca gcc cag tta     192
Ala Phe Glu Leu Asp His Leu Glu Phe Thr Thr Asn Ser Ala Gln Leu
    50                  55                  60 gga gat tct gac gaa gat aac gag aat gtg att aat gag atg aac gct     240
Gly Asp Ser Asp Glu Asp Asn Glu Asn Val Ile Asn Glu Met Asn Ala
65                  70                  75                  80 act gat gat gca aat gaa gct aac agc gag gaa aaa agc atg act ttg     288
Thr Asp Asp Ala Asn Glu Ala Asn Ser Glu Glu Lys Ser Met Thr Leu
                85                  90                  95 aag cag gcg ttg cta aaa tat cca aaa gca gcc ctg tgg tcc ata tta     336
Lys Gln Ala Leu Leu Lys Tyr Pro Lys Ala Ala Leu Trp Ser Ile Leu
            100                 105                 110 gtg tcg aca aca ttg att caa gag ggt tat gac aca gcc att cta gga     384
Val Ser Thr Thr Leu Ile Gln Glu Gly Tyr Asp Thr Ala Ile Leu Gly
        115                 120                 125 gct ttc tat gcc ctg cct gtt ttt caa aaa aaa tat ggt tct ttg aat     432
Ala Phe Tyr Ala Leu Pro Val Phe Gln Lys Lys Tyr Gly Ser Leu Asn
    130                 135                 140 agc aat aca gga gat tat gaa att tca gtt tct tgg caa atc ggt cta     480
Ser Asn Thr Gly Asp Tyr Glu Ile Ser Val Ser Trp Gln Ile Gly Leu
145                 150                 155                 160 tgt cta tgc tac atg gca ggt gaa att gtg ggg cta cag cta acg ggg     528
Cys Leu Cys Tyr Met Ala Gly Glu Ile Val Gly Leu Gln Leu Thr Gly
                165                 170                 175 ccc tcc gtg gat ctt gtt gga aat cgt tac aca ttg atc atg gcg ttg     576
Pro Ser Val Asp Leu Val Gly Asn Arg Tyr Thr Leu Ile Met Ala Leu
```

```
                 180               185                190
ttc ttt tta gcg gct ttc att ttc att ctg tat ttt tgc aag agt ttg    624
Phe Phe Leu Ala Ala Phe Ile Phe Ile Leu Tyr Phe Cys Lys Ser Leu
            195                 200                205 ggt atg att gcc gtg gga cag gca ttg tgt ggt atg cca tgg ggt tgt    672
Gly Met Ile Ala Val Gly Gln Ala Leu Cys Gly Met Pro Trp Gly Cys
210                 215                 220 ttc caa tgt ttg acc gtt tct tat gct tct gaa att tgt cct ttg gcc    720
Phe Gln Cys Leu Thr Val Ser Tyr Ala Ser Glu Ile Cys Pro Leu Ala
225                 230                 235                 240 cta aga tac tat ttg acg act tat tct aat tta tgt tgg acg ttc ggt    768
Leu Arg Tyr Tyr Leu Thr Thr Tyr Ser Asn Leu Cys Trp Thr Phe Gly
            245                 250                 255 caa ctt ttc gct gct ggt att atg aaa aat tcc cag aac aaa tat gcc    816
Gln Leu Phe Ala Ala Gly Ile Met Lys Asn Ser Gln Asn Lys Tyr Ala
            260                 265                 270 aac tca gaa cta gga tat aag cta cct ttt gct ttg cag tgg atc tgg    864
Asn Ser Glu Leu Gly Tyr Lys Leu Pro Phe Ala Leu Gln Trp Ile Trp
            275                 280                 285 ccc ctt cct ttg gcg gta ggt att ttt ttt gca cca gag tct cca tgg    912
Pro Leu Pro Leu Ala Val Gly Ile Phe Phe Ala Pro Glu Ser Pro Trp
            290                 295                 300 tgg ctg gtt aaa aaa gga agg att gat caa gcg agg aga tca ctt gaa    960
Trp Leu Val Lys Lys Gly Arg Ile Asp Gln Ala Arg Arg Ser Leu Glu
305                 310                 315                 320 aga aca tta agt ggt aaa gga ccc gag aaa gaa tta cta gtg act atg    1008
Arg Thr Leu Ser Gly Lys Gly Pro Glu Lys Glu Leu Leu Val Thr Met
            325                 330                 335 gaa ctc gat aaa atc aaa act act ata gaa aag gag cag aaa atg tct    1056
Glu Leu Asp Lys Ile Lys Thr Thr Ile Glu Lys Glu Gln Lys Met Ser
            340                 345                 350 gat gaa gga act tac tgg gat tgt gtg aaa gat ggt att aac agg aga    1104
Asp Glu Gly Thr Tyr Trp Asp Cys Val Lys Asp Gly Ile Asn Arg Arg
            355                 360                 365 aga acg aga ata gct tgt tta tgt tgg atc ggt caa tgc tcc tgt ggt    1152
Arg Thr Arg Ile Ala Cys Leu Cys Trp Ile Gly Gln Cys Ser Cys Gly
370                 375                 380 gca tca tta att ggt tat tca act tac ttt tat gaa aaa gct ggt gtt    1200
Ala Ser Leu Ile Gly Tyr Ser Thr Tyr Phe Tyr Glu Lys Ala Gly Val
385                 390                 395                 400 agc act gat acg gct ttt act ttc agt att atc caa tat tgt ctt ggt    1248
Ser Thr Asp Thr Ala Phe Thr Phe Ser Ile Ile Gln Tyr Cys Leu Gly
            405                 410                 415 att gct gca acg ttt gta tcc tgg tgg gct tca aaa tat tgt ggc aga    1296
Ile Ala Ala Thr Phe Val Ser Trp Trp Ala Ser Lys Tyr Cys Gly Arg
            420                 425                 430 ttt gac ctt tat gct ttt ggg ctg gct ttt cag gct att atg ttc ttc    1344
Phe Asp Leu Tyr Ala Phe Gly Leu Ala Phe Gln Ala Ile Met Phe Phe
            435                 440                 445 att atc ggt ggt tta gga tgt tca gac act cat ggc gct aaa atg ggt    1392
Ile Ile Gly Gly Leu Gly Cys Ser Asp Thr His Gly Ala Lys Met Gly
450                 455                 460 agt ggt gct ctt cta atg gtt gtc gcg ttc ttt tac aac ctc ggt att    1440
Ser Gly Ala Leu Leu Met Val Val Ala Phe Phe Tyr Asn Leu Gly Ile
465                 470                 475                 480 gca cct gtt gtt ttt tgc tta gtg tct gaa atg ccg tct tca agg cta    1488
Ala Pro Val Val Phe Cys Leu Val Ser Glu Met Pro Ser Ser Arg Leu
            485                 490                 495 aga acc aaa aca att att ttg gct cgt aat gct tac aat gtg atc caa    1536
Arg Thr Lys Thr Ile Ile Leu Ala Arg Asn Ala Tyr Asn Val Ile Gln
```

```
                         500                 505                 510
gtt gta gtt aca gtt ttg att atg tac caa ttg aac tca gag aaa tgg      1584
Val Val Val Thr Val Leu Ile Met Tyr Gln Leu Asn Ser Glu Lys Trp
            515                 520                 525 aat tgg ggt gct aaa tca ggc ttt ttc tgg gga gga ttt tgt ctg gcc      1632
Asn Trp Gly Ala Lys Ser Gly Phe Phe Trp Gly Gly Phe Cys Leu Ala
530                 535                 540 act tta gct tgg gct gtt gtc gat tta cca gaa acc gct ggc agg act      1680
Thr Leu Ala Trp Ala Val Val Asp Leu Pro Glu Thr Ala Gly Arg Thr
545                 550                 555                 560 ttt att gag ata aat gaa ttg ttt aga ctt ggg gta cct gcc aga aaa      1728
Phe Ile Glu Ile Asn Glu Leu Phe Arg Leu Gly Val Pro Ala Arg Lys
                565                 570                 575 ttt gca tct act gtg gtt gat cca ttc gga aag gga aaa act caa cat      1776
Phe Ala Ser Thr Val Val Asp Pro Phe Gly Lys Gly Lys Thr Gln His
            580                 585                 590 gat tcg cta gct gat gag agt atc agt cag tcc tca agc ata aaa cag      1824
Asp Ser Leu Ala Asp Glu Ser Ile Ser Gln Ser Ser Ser Ile Lys Gln
        595                 600                 605 cga gaa tta aat gca gct gat aaa tgt                                  1851
Arg Glu Leu Asn Ala Ala Asp Lys Cys
    610                 615

<210> SEQ ID NO 10
<211> LENGTH: 617
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Lys Asn Ile Ile Ser Leu Val Ser Lys Lys Ala Ala Ser Lys
1               5                   10                  15

Asn Glu Asp Lys Asn Ile Ser Glu Ser Ser Arg Asp Ile Val Asn Gln
            20                  25                  30

Gln Glu Val Phe Asn Thr Glu Asp Phe Glu Glu Gly Lys Lys Asp Ser
        35                  40                  45

Ala Phe Glu Leu Asp His Leu Glu Phe Thr Thr Asn Ser Ala Gln Leu
    50                  55                  60

Gly Asp Ser Asp Glu Asp Asn Glu Asn Val Ile Asn Glu Met Asn Ala
65                  70                  75                  80

Thr Asp Asp Ala Asn Glu Ala Asn Ser Glu Glu Lys Ser Met Thr Leu
                85                  90                  95

Lys Gln Ala Leu Leu Lys Tyr Pro Lys Ala Ala Leu Trp Ser Ile Leu
            100                 105                 110

Val Ser Thr Thr Leu Ile Gln Glu Gly Tyr Asp Thr Ala Ile Leu Gly
        115                 120                 125

Ala Phe Tyr Ala Leu Pro Val Phe Gln Lys Lys Tyr Gly Ser Leu Asn
    130                 135                 140

Ser Asn Thr Gly Asp Tyr Glu Ile Ser Val Ser Trp Gln Ile Gly Leu
145                 150                 155                 160

Cys Leu Cys Tyr Met Ala Gly Glu Ile Val Gly Leu Gln Leu Thr Gly
                165                 170                 175

Pro Ser Val Asp Leu Val Gly Asn Arg Tyr Thr Leu Ile Met Ala Leu
            180                 185                 190

Phe Phe Leu Ala Ala Phe Ile Phe Ile Leu Tyr Phe Cys Lys Ser Leu
        195                 200                 205
```

```
Gly Met Ile Ala Val Gly Gln Ala Leu Cys Gly Met Pro Trp Gly Cys
    210                 215                 220
Phe Gln Cys Leu Thr Val Ser Tyr Ala Ser Glu Ile Cys Pro Leu Ala
225                 230                 235                 240
Leu Arg Tyr Tyr Leu Thr Thr Tyr Ser Asn Leu Cys Trp Thr Phe Gly
                245                 250                 255
Gln Leu Phe Ala Ala Gly Ile Met Lys Asn Ser Gln Asn Lys Tyr Ala
            260                 265                 270
Asn Ser Glu Leu Gly Tyr Lys Leu Pro Phe Ala Leu Gln Trp Ile Trp
        275                 280                 285
Pro Leu Pro Leu Ala Val Gly Ile Phe Phe Ala Pro Glu Ser Pro Trp
    290                 295                 300
Trp Leu Val Lys Lys Gly Arg Ile Asp Gln Ala Arg Arg Ser Leu Glu
305                 310                 315                 320
Arg Thr Leu Ser Gly Lys Gly Pro Glu Lys Glu Leu Leu Val Thr Met
                325                 330                 335
Glu Leu Asp Lys Ile Lys Thr Thr Ile Glu Lys Glu Gln Lys Met Ser
            340                 345                 350
Asp Glu Gly Thr Tyr Trp Asp Cys Val Lys Asp Gly Ile Asn Arg Arg
        355                 360                 365
Arg Thr Arg Ile Ala Cys Leu Cys Trp Ile Gly Gln Cys Ser Cys Gly
    370                 375                 380
Ala Ser Leu Ile Gly Tyr Ser Thr Tyr Phe Tyr Glu Lys Ala Gly Val
385                 390                 395                 400
Ser Thr Asp Thr Ala Phe Thr Phe Ser Ile Ile Gln Tyr Cys Leu Gly
                405                 410                 415
Ile Ala Ala Thr Phe Val Ser Trp Trp Ala Ser Lys Tyr Cys Gly Arg
            420                 425                 430
Phe Asp Leu Tyr Ala Phe Gly Leu Ala Phe Gln Ala Ile Met Phe Phe
        435                 440                 445
Ile Ile Gly Gly Leu Gly Cys Ser Asp Thr His Gly Ala Lys Met Gly
    450                 455                 460
Ser Gly Ala Leu Leu Met Val Ala Phe Phe Tyr Asn Leu Gly Ile
465                 470                 475                 480
Ala Pro Val Val Phe Cys Leu Val Ser Glu Met Pro Ser Ser Arg Leu
                485                 490                 495
Arg Thr Lys Thr Ile Ile Leu Ala Arg Asn Ala Tyr Asn Val Ile Gln
            500                 505                 510
Val Val Val Thr Val Leu Ile Met Tyr Gln Leu Asn Ser Glu Lys Trp
        515                 520                 525
Asn Trp Gly Ala Lys Ser Gly Phe Phe Trp Gly Gly Phe Cys Leu Ala
    530                 535                 540
Thr Leu Ala Trp Ala Val Val Asp Leu Pro Glu Thr Ala Gly Arg Thr
545                 550                 555                 560
Phe Ile Glu Ile Asn Glu Leu Phe Arg Leu Gly Val Pro Ala Arg Lys
                565                 570                 575
Phe Ala Ser Thr Val Val Asp Pro Phe Gly Lys Gly Lys Thr Gln His
            580                 585                 590
Asp Ser Leu Ala Asp Glu Ser Ile Ser Gln Ser Ser Ile Lys Gln
        595                 600                 605
Arg Glu Leu Asn Ala Ala Asp Lys Cys
    610                 615

<210> SEQ ID NO 11
```

<211> LENGTH: 1863
<212> TYPE: DNA
<213> ORGANISM: Artificial Sequence
<220> FEATURE:
<223> OTHER INFORMATION: Description of Artificial Sequence: Synthetic AMM polynucleotide
<220> FEATURE:
<221> NAME/KEY: CDS
<222> LOCATION: (1)..(1863)
<223> OTHER INFORMATION: AMMp

<400> SEQUENCE: 11

| atg | aaa | aat | atc | att | tca | ttg | gta | agc | aag | aag | aag | gct | gcc | tca | aaa | 48 |
|---|---|---|---|---|---|---|---|---|---|---|---|---|---|---|---|---|
| Met | Lys | Asn | Ile | Ile | Ser | Leu | Val | Ser | Lys | Lys | Lys | Ala | Ala | Ser | Lys | |
| 1 | | | | 5 | | | | | 10 | | | | | 15 | | |

| aat | gag | gat | aaa | aac | att | tct | gag | tct | tca | aga | gat | att | gta | aac | caa | 96 |
|---|---|---|---|---|---|---|---|---|---|---|---|---|---|---|---|---|
| Asn | Glu | Asp | Lys | Asn | Ile | Ser | Glu | Ser | Ser | Arg | Asp | Ile | Val | Asn | Gln | |
| | | 20 | | | | | 25 | | | | | 30 | | | | |

| cag | gag | gtt | ttc | aat | act | gaa | gat | ttt | gaa | gaa | ggg | aaa | aag | gat | agt | 144 |
|---|---|---|---|---|---|---|---|---|---|---|---|---|---|---|---|---|
| Gln | Glu | Val | Phe | Asn | Thr | Glu | Asp | Phe | Glu | Glu | Gly | Lys | Lys | Asp | Ser | |
| | | | 35 | | | | | 40 | | | | | 45 | | | |

| gcc | ttt | gag | cta | gac | cac | tta | gag | ttc | acc | acc | aat | tca | gcc | cag | tta | 192 |
|---|---|---|---|---|---|---|---|---|---|---|---|---|---|---|---|---|
| Ala | Phe | Glu | Leu | Asp | His | Leu | Glu | Phe | Thr | Thr | Asn | Ser | Ala | Gln | Leu | |
| | 50 | | | | | 55 | | | | | 60 | | | | | |

| gga | gat | tct | gac | gaa | gat | aac | gag | aat | gtg | att | aat | gag | atg | aac | gct | 240 |
|---|---|---|---|---|---|---|---|---|---|---|---|---|---|---|---|---|
| Gly | Asp | Ser | Asp | Glu | Asp | Asn | Glu | Asn | Val | Ile | Asn | Glu | Met | Asn | Ala | |
| 65 | | | | | 70 | | | | | 75 | | | | | 80 | |

| act | gat | gat | gca | aat | gaa | gct | aac | agc | gag | gaa | aaa | agc | atg | act | ttg | 288 |
|---|---|---|---|---|---|---|---|---|---|---|---|---|---|---|---|---|
| Thr | Asp | Asp | Ala | Asn | Glu | Ala | Asn | Ser | Glu | Glu | Lys | Ser | Met | Thr | Leu | |
| | | | | 85 | | | | | 90 | | | | | 95 | | |

| aag | cag | gcg | ttg | cta | aaa | tat | cca | aaa | gca | gcc | ctg | tgg | tcc | ata | tta | 336 |
|---|---|---|---|---|---|---|---|---|---|---|---|---|---|---|---|---|
| Lys | Gln | Ala | Leu | Leu | Lys | Tyr | Pro | Lys | Ala | Ala | Leu | Trp | Ser | Ile | Leu | |
| | | | 100 | | | | | 105 | | | | | 110 | | | |

| gtg | tcg | aca | aca | ttg | att | caa | gag | ggt | tat | gac | aca | gcc | att | cta | gga | 384 |
|---|---|---|---|---|---|---|---|---|---|---|---|---|---|---|---|---|
| Val | Ser | Thr | Thr | Leu | Ile | Gln | Glu | Gly | Tyr | Asp | Thr | Ala | Ile | Leu | Gly | |
| | | | 115 | | | | | 120 | | | | | 125 | | | |

| gct | ttc | tat | gcc | ctg | cct | gtt | ttt | caa | aaa | aaa | tat | ggt | tct | ttg | aat | 432 |
|---|---|---|---|---|---|---|---|---|---|---|---|---|---|---|---|---|
| Ala | Phe | Tyr | Ala | Leu | Pro | Val | Phe | Gln | Lys | Lys | Tyr | Gly | Ser | Leu | Asn | |
| | 130 | | | | | 135 | | | | | 140 | | | | | |

| agc | aat | aca | gga | gat | tat | gaa | att | tca | gtt | tct | tgg | caa | atc | ggt | cta | 480 |
|---|---|---|---|---|---|---|---|---|---|---|---|---|---|---|---|---|
| Ser | Asn | Thr | Gly | Asp | Tyr | Glu | Ile | Ser | Val | Ser | Trp | Gln | Ile | Gly | Leu | |
| 145 | | | | | 150 | | | | | 155 | | | | | 160 | |

| tgt | cta | tgc | tac | atg | gca | ggt | gaa | att | gtg | ggg | cta | cag | cta | acg | ggg | 528 |
|---|---|---|---|---|---|---|---|---|---|---|---|---|---|---|---|---|
| Cys | Leu | Cys | Tyr | Met | Ala | Gly | Glu | Ile | Val | Gly | Leu | Gln | Leu | Thr | Gly | |
| | | | | 165 | | | | | 170 | | | | | 175 | | |

| ccc | tcc | gtg | gat | ctt | gtt | gga | aat | cgt | tac | aca | ttg | atc | atg | gcg | ttg | 576 |
|---|---|---|---|---|---|---|---|---|---|---|---|---|---|---|---|---|
| Pro | Ser | Val | Asp | Leu | Val | Gly | Asn | Arg | Tyr | Thr | Leu | Ile | Met | Ala | Leu | |
| | | | 180 | | | | | 185 | | | | | 190 | | | |

| ttc | ttt | tta | gcg | gct | ttc | att | ttc | att | ctg | tat | ttt | tgc | aag | agt | ttg | 624 |
|---|---|---|---|---|---|---|---|---|---|---|---|---|---|---|---|---|
| Phe | Phe | Leu | Ala | Ala | Phe | Ile | Phe | Ile | Leu | Tyr | Phe | Cys | Lys | Ser | Leu | |
| | | 195 | | | | | 200 | | | | | 205 | | | | |

| ggt | atg | att | gcc | gtg | gga | cag | gca | ttg | tgt | ggt | atg | cca | tgg | ggt | tgt | 672 |
|---|---|---|---|---|---|---|---|---|---|---|---|---|---|---|---|---|
| Gly | Met | Ile | Ala | Val | Gly | Gln | Ala | Leu | Cys | Gly | Met | Pro | Trp | Gly | Cys | |
| | 210 | | | | | 215 | | | | | 220 | | | | | |

| ttc | caa | tgt | ttg | acc | gtt | tct | tat | gct | tct | gaa | att | tgt | cct | ttg | gcc | 720 |
|---|---|---|---|---|---|---|---|---|---|---|---|---|---|---|---|---|
| Phe | Gln | Cys | Leu | Thr | Val | Ser | Tyr | Ala | Ser | Glu | Ile | Cys | Pro | Leu | Ala | |
| 225 | | | | | 230 | | | | | 235 | | | | | 240 | |

| cta | aga | tac | tat | ttg | acg | act | tat | tct | aat | tta | tgt | tgg | acg | ttc | ggt | 768 |
|---|---|---|---|---|---|---|---|---|---|---|---|---|---|---|---|---|
| Leu | Arg | Tyr | Tyr | Leu | Thr | Thr | Tyr | Ser | Asn | Leu | Cys | Trp | Thr | Phe | Gly | |
| | | | | 245 | | | | | 250 | | | | | 255 | | |

| caa | ctt | ttc | gct | gct | ggt | att | atg | aaa | aat | tcc | cag | aac | aaa | tat | gcc | 816 |
|---|---|---|---|---|---|---|---|---|---|---|---|---|---|---|---|---|
| Gln | Leu | Phe | Ala | Ala | Gly | Ile | Met | Lys | Asn | Ser | Gln | Asn | Lys | Tyr | Ala | |
| | | | 260 | | | | | 265 | | | | | 270 | | | |

| | | |
|---|---|---|
| aac tca gaa cta gga tat aag cta cct ttt gct ttg cag tgg atc tgg<br>Asn Ser Glu Leu Gly Tyr Lys Leu Pro Phe Ala Leu Gln Trp Ile Trp<br>275 280 285 | | 864 |
| ccc ctt cct ttg gcg gta ggt att ttt ttt gca cca gag tct cca tgg<br>Pro Leu Pro Leu Ala Val Gly Ile Phe Phe Ala Pro Glu Ser Pro Trp<br>290 295 300 | | 912 |
| tgg ctg gtt aaa aaa gga agg att gat caa gcg agg aga tca ctt gaa<br>Trp Leu Val Lys Lys Gly Arg Ile Asp Gln Ala Arg Arg Ser Leu Glu<br>305 310 315 320 | | 960 |
| aga aca tta agt ggt aaa gga ccc gag aaa gaa tta cta gtg act atg<br>Arg Thr Leu Ser Gly Lys Gly Pro Glu Lys Glu Leu Leu Val Thr Met<br>325 330 335 | | 1008 |
| gaa ctc gat aaa atc aaa act act ata gaa aag gag cag aaa atg tct<br>Glu Leu Asp Lys Ile Lys Thr Thr Ile Glu Lys Glu Gln Lys Met Ser<br>340 345 350 | | 1056 |
| gat gaa gga act tac tgg gat tgt gtg aaa gat ggt att aac agg aga<br>Asp Glu Gly Thr Tyr Trp Asp Cys Val Lys Asp Gly Ile Asn Arg Arg<br>355 360 365 | | 1104 |
| aga acg aga ata gct tgt tta tgt tgg atc ggt caa tgc tcc tgt ggt<br>Arg Thr Arg Ile Ala Cys Leu Cys Trp Ile Gly Gln Cys Ser Cys Gly<br>370 375 380 | | 1152 |
| gca tca tta att ggt tat tca act tac ttt tat gaa aaa gct ggt gtt<br>Ala Ser Leu Ile Gly Tyr Ser Thr Tyr Phe Tyr Glu Lys Ala Gly Val<br>385 390 395 400 | | 1200 |
| agc act gat acg gct ttt act ttc agt att atc caa tat tgt ctt ggt<br>Ser Thr Asp Thr Ala Phe Thr Phe Ser Ile Ile Gln Tyr Cys Leu Gly<br>405 410 415 | | 1248 |
| att gct gca acg ttt gta tcc tgg tgg gct tca aaa tat tgt ggc aga<br>Ile Ala Ala Thr Phe Val Ser Trp Trp Ala Ser Lys Tyr Cys Gly Arg<br>420 425 430 | | 1296 |
| ttt gac ctt tat gct ttt ggg ctg gct ttt cag gct att atg ttc ttc<br>Phe Asp Leu Tyr Ala Phe Gly Leu Ala Phe Gln Ala Ile Met Phe Phe<br>435 440 445 | | 1344 |
| att atc ggt ggt tta gga tgt tca gac act cat ggc gct aaa atg ggt<br>Ile Ile Gly Gly Leu Gly Cys Ser Asp Thr His Gly Ala Lys Met Gly<br>450 455 460 | | 1392 |
| agt ggt gct ctt cta atg gtt gtc gcg ttc ttt tac aac ctc ggt att<br>Ser Gly Ala Leu Leu Met Val Val Ala Phe Phe Tyr Asn Leu Gly Ile<br>465 470 475 480 | | 1440 |
| gca cct gtt gtt ttt tgc tta gtg tct gaa atg ccg tct tca agg cta<br>Ala Pro Val Val Phe Cys Leu Val Ser Glu Met Pro Ser Ser Arg Leu<br>485 490 495 | | 1488 |
| aga acc aaa aca att att ttg gct cgt aat gct tac aat gtg atc caa<br>Arg Thr Lys Thr Ile Ile Leu Ala Arg Asn Ala Tyr Asn Val Ile Gln<br>500 505 510 | | 1536 |
| gtt gta gtt aca gtt ttg att atg tac caa ttg aac tca gag aaa tgg<br>Val Val Val Thr Val Leu Ile Met Tyr Gln Leu Asn Ser Glu Lys Trp<br>515 520 525 | | 1584 |
| aat tgg ggt gct aaa tca ggc ttt ttc tgg gga gga ttt tgt ctg gcc<br>Asn Trp Gly Ala Lys Ser Gly Phe Phe Trp Gly Gly Phe Cys Leu Ala<br>530 535 540 | | 1632 |
| act tta gct tgg gct gtt gtc gat tta cca gaa acc gct ggc agg act<br>Thr Leu Ala Trp Ala Val Val Asp Leu Pro Glu Thr Ala Gly Arg Thr<br>545 550 555 560 | | 1680 |
| ttt att gag ata aat gaa ttg ttt aga ctt ggt gtt cca gca aga aag<br>Phe Ile Glu Ile Asn Glu Leu Phe Arg Leu Gly Val Pro Ala Arg Lys<br>565 570 575 | | 1728 |
| ttc aag tcg act aaa gtc gac cct ttt gca gct gcc aaa gca gca gct<br>Phe Lys Ser Thr Lys Val Asp Pro Phe Ala Ala Ala Lys Ala Ala Ala<br>580 585 590 | | 1776 |

```
gca gaa att aat gtt aaa gat ccg aag gaa gat ttg gaa act tct gtg    1824
Ala Glu Ile Asn Val Lys Asp Pro Lys Glu Asp Leu Glu Thr Ser Val
            595                 600                 605 gta gat gaa ggg cga aac acc tca tct gtt gtg aac aaa                1863
Val Asp Glu Gly Arg Asn Thr Ser Ser Val Val Asn Lys
    610                 615                 620
```

<210> SEQ ID NO 12
<211> LENGTH: 621
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Met Lys Asn Ile Ile Ser Leu Val Ser Lys Lys Ala Ala Ser Lys
1               5                   10                  15

Asn Glu Asp Lys Asn Ile Ser Glu Ser Ser Arg Asp Ile Val Asn Gln
            20                  25                  30

Gln Glu Val Phe Asn Thr Glu Asp Phe Glu Glu Gly Lys Lys Asp Ser
        35                  40                  45

Ala Phe Glu Leu Asp His Leu Glu Phe Thr Thr Asn Ser Ala Gln Leu
    50                  55                  60

Gly Asp Ser Asp Glu Asn Glu Asn Val Ile Asn Glu Met Asn Ala
65                  70                  75                  80

Thr Asp Asp Ala Asn Glu Ala Asn Ser Glu Glu Lys Ser Met Thr Leu
                85                  90                  95

Lys Gln Ala Leu Leu Lys Tyr Pro Lys Ala Ala Leu Trp Ser Ile Leu
            100                 105                 110

Val Ser Thr Thr Leu Ile Gln Glu Gly Tyr Asp Thr Ala Ile Leu Gly
        115                 120                 125

Ala Phe Tyr Ala Leu Pro Val Phe Gln Lys Lys Tyr Gly Ser Leu Asn
    130                 135                 140

Ser Asn Thr Gly Asp Tyr Glu Ile Ser Val Ser Trp Gln Ile Gly Leu
145                 150                 155                 160

Cys Leu Cys Tyr Met Ala Gly Glu Ile Val Gly Leu Gln Leu Thr Gly
                165                 170                 175

Pro Ser Val Asp Leu Val Gly Asn Arg Tyr Thr Leu Ile Met Ala Leu
            180                 185                 190

Phe Phe Leu Ala Ala Phe Ile Phe Ile Leu Tyr Phe Cys Lys Ser Leu
        195                 200                 205

Gly Met Ile Ala Val Gly Gln Ala Leu Cys Gly Met Pro Trp Gly Cys
    210                 215                 220

Phe Gln Cys Leu Thr Val Ser Tyr Ala Ser Glu Ile Cys Pro Leu Ala
225                 230                 235                 240

Leu Arg Tyr Tyr Leu Thr Thr Tyr Ser Asn Leu Cys Trp Thr Phe Gly
                245                 250                 255

Gln Leu Phe Ala Ala Gly Ile Met Lys Asn Ser Gln Asn Lys Tyr Ala
            260                 265                 270

Asn Ser Glu Leu Gly Tyr Lys Leu Pro Phe Ala Leu Gln Trp Ile Trp
        275                 280                 285

Pro Leu Pro Leu Ala Val Gly Ile Phe Phe Ala Pro Glu Ser Pro Trp
    290                 295                 300

Trp Leu Val Lys Lys Gly Arg Ile Asp Gln Ala Arg Arg Ser Leu Glu
305                 310                 315                 320
```

```
Arg Thr Leu Ser Gly Lys Gly Pro Glu Lys Glu Leu Val Thr Met
             325                 330                 335

Glu Leu Asp Lys Ile Lys Thr Thr Ile Glu Lys Glu Gln Lys Met Ser
             340                 345                 350

Asp Glu Gly Thr Tyr Trp Asp Cys Val Lys Asp Gly Ile Asn Arg Arg
             355                 360                 365

Arg Thr Arg Ile Ala Cys Leu Cys Trp Ile Gly Gln Cys Ser Cys Gly
    370                 375                 380

Ala Ser Leu Ile Gly Tyr Ser Thr Tyr Phe Tyr Glu Lys Ala Gly Val
385                 390                 395                 400

Ser Thr Asp Thr Ala Phe Thr Phe Ser Ile Ile Gln Tyr Cys Leu Gly
             405                 410                 415

Ile Ala Ala Thr Phe Val Ser Trp Trp Ala Ser Lys Tyr Cys Gly Arg
             420                 425                 430

Phe Asp Leu Tyr Ala Phe Gly Leu Ala Phe Gln Ala Ile Met Phe Phe
             435                 440                 445

Ile Ile Gly Gly Leu Gly Cys Ser Asp Thr His Gly Ala Lys Met Gly
             450                 455                 460

Ser Gly Ala Leu Leu Met Val Val Ala Phe Phe Tyr Asn Leu Gly Ile
465                 470                 475                 480

Ala Pro Val Val Phe Cys Leu Val Ser Glu Met Pro Ser Ser Arg Leu
             485                 490                 495

Arg Thr Lys Thr Ile Ile Leu Ala Arg Asn Ala Tyr Asn Val Ile Gln
             500                 505                 510

Val Val Val Thr Val Leu Ile Met Tyr Gln Leu Asn Ser Glu Lys Trp
             515                 520                 525

Asn Trp Gly Ala Lys Ser Gly Phe Phe Trp Gly Gly Phe Cys Leu Ala
530                 535                 540

Thr Leu Ala Trp Ala Val Val Asp Leu Pro Glu Thr Ala Gly Arg Thr
545                 550                 555                 560

Phe Ile Glu Ile Asn Glu Leu Phe Arg Leu Gly Val Pro Ala Arg Lys
             565                 570                 575

Phe Lys Ser Thr Lys Val Asp Pro Phe Ala Ala Lys Ala Ala Ala
             580                 585                 590

Ala Glu Ile Asn Val Lys Asp Pro Lys Glu Asp Leu Glu Thr Ser Val
             595                 600                 605

Val Asp Glu Gly Arg Asn Thr Ser Ser Val Val Asn Lys
610                 615                 620

<210> SEQ ID NO 13
<211> LENGTH: 1827
<212> TYPE: DNA
<213> ORGANISM: Artificial Sequence
<220> FEATURE:
<223> OTHER INFORMATION: Description of Artificial Sequence: Synthetic
      MAA polynucleotide
<220> FEATURE:
<221> NAME/KEY: CDS
<222> LOCATION: (1)..(1827)
<223> OTHER INFORMATION: MAAp

<400> SEQUENCE: 13 atg aag gga tta tcc tca tta ata aac aga aaa aaa gac agg aac gac      48
Met Lys Gly Leu Ser Ser Leu Ile Asn Arg Lys Lys Asp Arg Asn Asp
1               5                   10                  15 tca cac tta gat gag atc gag aat ggc gtg aac gct acc gaa ttc aac      96
Ser His Leu Asp Glu Ile Glu Asn Gly Val Asn Ala Thr Glu Phe Asn
            20                  25                  30
```

-continued

| | |
|---|---|
| tcg ata gag atg gag gag caa ggt aag aaa agt gat ttt ggt ctt tcc<br>Ser Ile Glu Met Glu Glu Gln Gly Lys Lys Ser Asp Phe Gly Leu Ser<br>35                                       40                                  45 | 144 |
| cat cat gag tac ggt cca ggt tca cta ata cca aac gat aat aat gaa<br>His His Glu Tyr Gly Pro Gly Ser Leu Ile Pro Asn Asp Asn Asn Glu<br>50                                 55                            60 | 192 |
| gaa gtc ccc gac ctt ctc gat gaa gct atg cag gac gcc aaa gag gca<br>Glu Val Pro Asp Leu Leu Asp Glu Ala Met Gln Asp Ala Lys Glu Ala<br>65                                  70                         75                        80 | 240 |
| gat gaa agt gag agg gga atg cca ctc atg aca gct ttg aag aca tat<br>Asp Glu Ser Glu Arg Gly Met Pro Leu Met Thr Ala Leu Lys Thr Tyr<br>                        85                         90                         95 | 288 |
| cca aaa gct gct gct tgg tca cta tta gtg tcg act acc ctg gtt atg<br>Pro Lys Ala Ala Ala Trp Ser Leu Leu Val Ser Thr Thr Leu Val Met<br>          100                         105                         110 | 336 |
| gaa ggt tat gat acc gca cta ctg agc gca ctg tat gcc ctg cca gtt<br>Glu Gly Tyr Asp Thr Ala Leu Leu Ser Ala Leu Tyr Ala Leu Pro Val<br>          115                         120                         125 | 384 |
| ttt cag aga aaa ttc ggt act ttg aac ggg gag ggt tct tac gaa att<br>Phe Gln Arg Lys Phe Gly Thr Leu Asn Gly Glu Gly Ser Tyr Glu Ile<br>130                             135                         140 | 432 |
| act tcc caa tgg cag att ggt tta aac atg tgt gtc ctt tgt ggt gag<br>Thr Ser Gln Trp Gln Ile Gly Leu Asn Met Cys Val Leu Cys Gly Glu<br>145                             150                         155                        160 | 480 |
| atg att ggt ttg caa atc acg act tat atg gtt gaa ttt atg ggg aat<br>Met Ile Gly Leu Gln Ile Thr Thr Tyr Met Val Glu Phe Met Gly Asn<br>                       165                         170                         175 | 528 |
| cgt tat acg atg att aca gca ctt ggt ttg tta act gct tat atc ttt<br>Arg Tyr Thr Met Ile Thr Ala Leu Gly Leu Leu Thr Ala Tyr Ile Phe<br>                   180                         185                         190 | 576 |
| atc ctc tac tac tgt aaa agt tta gct atg att gct gtg gga caa att<br>Ile Leu Tyr Tyr Cys Lys Ser Leu Ala Met Ile Ala Val Gly Gln Ile<br>195                             200                         205 | 624 |
| ctc tca gct ata cca tgg ggt tgt ttc caa agt ttg gct gtt act tat<br>Leu Ser Ala Ile Pro Trp Gly Cys Phe Gln Ser Leu Ala Val Thr Tyr<br>210                             215                         220 | 672 |
| gct tcg gaa gtt tgc cct tta gca tta aga tat tac atg acc agt tac<br>Ala Ser Glu Val Cys Pro Leu Ala Leu Arg Tyr Tyr Met Thr Ser Tyr<br>225                             230                         235                        240 | 720 |
| tcc aac att tgt tgg tta ttt ggt caa atc ttc gcc tct ggt att atg<br>Ser Asn Ile Cys Trp Leu Phe Gly Gln Ile Phe Ala Ser Gly Ile Met<br>                       245                         250                         255 | 768 |
| aaa aac tca caa gag aat tta ggg aac tcc gac ttg ggc tat aaa ttg<br>Lys Asn Ser Gln Glu Asn Leu Gly Asn Ser Asp Leu Gly Tyr Lys Leu<br>                       260                         265                         270 | 816 |
| cca ttt gct tta caa tgg att tgg cct gct cct tta atg atc ggt atc<br>Pro Phe Ala Leu Gln Trp Ile Trp Pro Ala Pro Leu Met Ile Gly Ile<br>275                             280                         285 | 864 |
| ttt ttc gct cct gag tcg ccc tgg tgg ttg gtg aga aag gat agg gtc<br>Phe Phe Ala Pro Glu Ser Pro Trp Trp Leu Val Arg Lys Asp Arg Val<br>290                             295                         300 | 912 |
| gct gag gca aga aaa tct tta agc aga att ttg agt ggt aaa ggc gcc<br>Ala Glu Ala Arg Lys Ser Leu Ser Arg Ile Leu Ser Gly Lys Gly Ala<br>305                             310                         315                        320 | 960 |
| gag aag gac att caa gtt gat ctt act tta aag cag att gaa ttg act<br>Glu Lys Asp Ile Gln Val Asp Leu Thr Leu Lys Gln Ile Glu Leu Thr<br>                       325                         330                         335 | 1008 |
| att gaa aaa gaa aga ctt tta gca tct aaa tca gga tca ttc ttt aat<br>Ile Glu Lys Glu Arg Leu Leu Ala Ser Lys Ser Gly Ser Phe Phe Asn<br>340                             345                         350 | 1056 |

-continued

```
tgt ttc aag gga gtt aat gga aga aga acg aga ctt gca tgt tta act      1104
Cys Phe Lys Gly Val Asn Gly Arg Arg Thr Arg Leu Ala Cys Leu Thr
        355                 360                 365 tgg gta gct caa aat agt agc ggt gcc gtt tta ctt ggt tac tcg aca      1152
Trp Val Ala Gln Asn Ser Ser Gly Ala Val Leu Leu Gly Tyr Ser Thr
    370                 375                 380 tat ttt ttt gaa aga gca ggt atg gcc acc gac aag gcg ttt act ttt      1200
Tyr Phe Phe Glu Arg Ala Gly Met Ala Thr Asp Lys Ala Phe Thr Phe
385                 390                 395                 400 tct cta att cag tac tgt ctt ggg tta gcg ggt aca ctt tgc tcc tgg      1248
Ser Leu Ile Gln Tyr Cys Leu Gly Leu Ala Gly Thr Leu Cys Ser Trp
            405                 410                 415 gta ata tct ggc cgt gtt ggt aga tgg aca ata ctg acc tat ggt ctt      1296
Val Ile Ser Gly Arg Val Gly Arg Trp Thr Ile Leu Thr Tyr Gly Leu
        420                 425                 430 gca ttt caa atg gtc tgc tta ttt att att ggt gga atg ggt ttt ggt      1344
Ala Phe Gln Met Val Cys Leu Phe Ile Ile Gly Gly Met Gly Phe Gly
    435                 440                 445 tct gga agc agc gct agt aat ggt gcc ggt ggt tta ttg ctg gct tta      1392
Ser Gly Ser Ser Ala Ser Asn Gly Ala Gly Gly Leu Leu Leu Ala Leu
450                 455                 460 tca ttc ttt tac aat gct ggt atc ggt gca gtt gtt tac tgt atc gtt      1440
Ser Phe Phe Tyr Asn Ala Gly Ile Gly Ala Val Val Tyr Cys Ile Val
465                 470                 475                 480 gct gaa att cca tca gcg gag ttg aga act aag act ata gtg ctg gcc      1488
Ala Glu Ile Pro Ser Ala Glu Leu Arg Thr Lys Thr Ile Val Leu Ala
            485                 490                 495 cgt att tgc tac aat ctc atg gcc gtt att aac gct ata tta acg ccc      1536
Arg Ile Cys Tyr Asn Leu Met Ala Val Ile Asn Ala Ile Leu Thr Pro
        500                 505                 510 tat atg cta aac gtg agc gat tgg aac tgg ggt gcc aaa act ggt cta      1584
Tyr Met Leu Asn Val Ser Asp Trp Asn Trp Gly Ala Lys Thr Gly Leu
    515                 520                 525 tac tgg ggt ggt ttc aca gca gtc act tta gct tgg gtc atc atc gat      1632
Tyr Trp Gly Gly Phe Thr Ala Val Thr Leu Ala Trp Val Ile Ile Asp
530                 535                 540 ctg cct gag aca act ggt aga acc ttc agt gaa att aat gaa ctt ttc      1680
Leu Pro Glu Thr Thr Gly Arg Thr Phe Ser Glu Ile Asn Glu Leu Phe
545                 550                 555                 560 aac caa ggg gtt cct gcc aga aaa ttt gca tct act gtg gtt gat cca      1728
Asn Gln Gly Val Pro Ala Arg Lys Phe Ala Ser Thr Val Val Asp Pro
            565                 570                 575 ttc gga aag gga aaa act caa cat gat tcg cta gct gat gag agt atc      1776
Phe Gly Lys Gly Lys Thr Gln His Asp Ser Leu Ala Asp Glu Ser Ile
        580                 585                 590 agt cag tcc tca agc ata aaa cag cga gaa tta aat gca gct gat aaa      1824
Ser Gln Ser Ser Ser Ile Lys Gln Arg Glu Leu Asn Ala Ala Asp Lys
    595                 600                 605 tgt                                                                   1827
Cys

<210> SEQ ID NO 14
<211> LENGTH: 609
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Lys Gly Leu Ser Ser Leu Ile Asn Arg Lys Lys Asp Arg Asn Asp
1               5                   10                  15
```

-continued

Ser His Leu Asp Glu Ile Glu Asn Gly Val Asn Ala Thr Glu Phe Asn
           20                  25                  30

Ser Ile Glu Met Glu Glu Gln Gly Lys Lys Ser Asp Phe Gly Leu Ser
           35                  40                  45

His His Glu Tyr Gly Pro Gly Ser Leu Ile Pro Asn Asp Asn Asn Glu
     50                  55                  60

Glu Val Pro Asp Leu Leu Asp Glu Ala Met Gln Asp Ala Lys Glu Ala
65                  70                  75                  80

Asp Glu Ser Glu Arg Gly Met Pro Leu Met Thr Ala Leu Lys Thr Tyr
                85                  90                  95

Pro Lys Ala Ala Ala Trp Ser Leu Leu Val Ser Thr Thr Leu Val Met
                100                 105                 110

Glu Gly Tyr Asp Thr Ala Leu Leu Ser Ala Leu Tyr Ala Leu Pro Val
                115                 120                 125

Phe Gln Arg Lys Phe Gly Thr Leu Asn Gly Glu Gly Ser Tyr Glu Ile
            130                 135                 140

Thr Ser Gln Trp Gln Ile Gly Leu Asn Met Cys Val Leu Cys Gly Glu
145                 150                 155                 160

Met Ile Gly Leu Gln Ile Thr Thr Tyr Met Val Glu Phe Met Gly Asn
                165                 170                 175

Arg Tyr Thr Met Ile Thr Ala Leu Gly Leu Leu Thr Ala Tyr Ile Phe
                180                 185                 190

Ile Leu Tyr Tyr Cys Lys Ser Leu Ala Met Ile Ala Val Gly Gln Ile
            195                 200                 205

Leu Ser Ala Ile Pro Trp Gly Cys Phe Gln Ser Leu Ala Val Thr Tyr
210                 215                 220

Ala Ser Glu Val Cys Pro Leu Ala Leu Arg Tyr Tyr Met Thr Ser Tyr
225                 230                 235                 240

Ser Asn Ile Cys Trp Leu Phe Gly Gln Ile Phe Ala Ser Gly Ile Met
                245                 250                 255

Lys Asn Ser Gln Glu Asn Leu Gly Asn Ser Asp Leu Gly Tyr Lys Leu
                260                 265                 270

Pro Phe Ala Leu Gln Trp Ile Trp Pro Ala Pro Leu Met Ile Gly Ile
            275                 280                 285

Phe Phe Ala Pro Glu Ser Pro Trp Trp Leu Val Arg Lys Asp Arg Val
290                 295                 300

Ala Glu Ala Arg Lys Ser Leu Ser Arg Ile Leu Ser Gly Lys Gly Ala
305                 310                 315                 320

Glu Lys Asp Ile Gln Val Asp Leu Thr Leu Lys Gln Ile Glu Leu Thr
                325                 330                 335

Ile Glu Lys Glu Arg Leu Leu Ala Ser Lys Ser Gly Ser Phe Phe Asn
                340                 345                 350

Cys Phe Lys Gly Val Asn Gly Arg Arg Thr Arg Leu Ala Cys Leu Thr
            355                 360                 365

Trp Val Ala Gln Asn Ser Ser Gly Ala Val Leu Leu Gly Tyr Ser Thr
370                 375                 380

Tyr Phe Phe Glu Arg Ala Gly Met Ala Thr Asp Lys Ala Phe Thr Phe
385                 390                 395                 400

Ser Leu Ile Gln Tyr Cys Leu Gly Leu Ala Gly Thr Leu Cys Ser Trp
                405                 410                 415

Val Ile Ser Gly Arg Val Gly Arg Trp Thr Ile Leu Thr Tyr Gly Leu
                420                 425                 430

Ala Phe Gln Met Val Cys Leu Phe Ile Ile Gly Gly Met Gly Phe Gly

-continued

```
               435                 440                 445
Ser Gly Ser Ser Ala Ser Asn Gly Ala Gly Leu Leu Ala Leu
        450                 455                 460

Ser Phe Phe Tyr Asn Ala Gly Ile Gly Ala Val Val Tyr Cys Ile Val
465                 470                 475                 480

Ala Glu Ile Pro Ser Ala Glu Leu Arg Thr Lys Thr Ile Val Leu Ala
                485                 490                 495

Arg Ile Cys Tyr Asn Leu Met Ala Val Ile Asn Ala Ile Leu Thr Pro
            500                 505                 510

Tyr Met Leu Asn Val Ser Asp Trp Asn Trp Gly Ala Lys Thr Gly Leu
        515                 520                 525

Tyr Trp Gly Gly Phe Thr Ala Val Thr Leu Ala Trp Val Ile Ile Asp
    530                 535                 540

Leu Pro Glu Thr Thr Gly Arg Thr Phe Ser Glu Ile Asn Glu Leu Phe
545                 550                 555                 560

Asn Gln Gly Val Pro Ala Arg Lys Phe Ala Ser Thr Val Asp Pro
                565                 570                 575

Phe Gly Lys Gly Lys Thr Gln His Asp Ser Leu Ala Asp Glu Ser Ile
            580                 585                 590

Ser Gln Ser Ser Ser Ile Lys Gln Arg Glu Leu Asn Ala Ala Asp Lys
        595                 600                 605

Cys
```

<210> SEQ ID NO 15
<211> LENGTH: 1839
<212> TYPE: DNA
<213> ORGANISM: Artificial Sequence
<220> FEATURE:
<223> OTHER INFORMATION: Description of Artificial Sequence: Synthetic MAM polynucleotide
<220> FEATURE:
<221> NAME/KEY: CDS
<222> LOCATION: (1)..(1839)
<223> OTHER INFORMATION: MAMp

<400> SEQUENCE: 15

```
atg aag gga tta tcc tca tta ata aac aga aaa aaa gac agg aac gac      48
Met Lys Gly Leu Ser Ser Leu Ile Asn Arg Lys Lys Asp Arg Asn Asp
1               5                   10                  15 tca cac tta gat gag atc gag aat ggc gtg aac gct acc gaa ttc aac      96
Ser His Leu Asp Glu Ile Glu Asn Gly Val Asn Ala Thr Glu Phe Asn
            20                  25                  30 tcg ata gag atg gag gag caa ggt aag aaa agt gat ttt ggt ctt tcc     144
Ser Ile Glu Met Glu Glu Gln Gly Lys Lys Ser Asp Phe Gly Leu Ser
        35                  40                  45 cat cat gag tac ggt cca ggt tca cta ata cca aac gat aat aat gaa     192
His His Glu Tyr Gly Pro Gly Ser Leu Ile Pro Asn Asp Asn Asn Glu
    50                  55                  60 gaa gtc ccc gac ctt ctc gat gaa gct atg cag gac gcc aaa gag gca     240
Glu Val Pro Asp Leu Leu Asp Glu Ala Met Gln Asp Ala Lys Glu Ala
65                  70                  75                  80 gat gaa agt gag agg gga atg cca ctc atg aca gct ttg aag aca tat     288
Asp Glu Ser Glu Arg Gly Met Pro Leu Met Thr Ala Leu Lys Thr Tyr
                85                  90                  95 cca aaa gct gct gct tgg tca cta tta gtg tcg act acc ctg gtt atg     336
Pro Lys Ala Ala Ala Trp Ser Leu Leu Val Ser Thr Thr Leu Val Met
            100                 105                 110 gaa ggt tat gat acc gca cta ctg agc gca ctg tat gcc ctg cca gtt     384
Glu Gly Tyr Asp Thr Ala Leu Leu Ser Ala Leu Tyr Ala Leu Pro Val
        115                 120                 125
```

| | | |
|---|---|---|
| ttt cag aga aaa ttc ggt act ttg aac ggg gag ggt tct tac gaa att<br>Phe Gln Arg Lys Phe Gly Thr Leu Asn Gly Glu Gly Ser Tyr Glu Ile<br>130                        135                        140 | | 432 |
| act tcc caa tgg cag att ggt tta aac atg tgt gtc ctt tgt ggt gag<br>Thr Ser Gln Trp Gln Ile Gly Leu Asn Met Cys Val Leu Cys Gly Glu<br>145                        150                        155                        160 | | 480 |
| atg att ggt ttg caa atc acg act tat atg gtt gaa ttt atg ggg aat<br>Met Ile Gly Leu Gln Ile Thr Thr Tyr Met Val Glu Phe Met Gly Asn<br>                  165                        170                        175 | | 528 |
| cgt tat acg atg att aca gca ctt ggt ttg tta act gct tat atc ttt<br>Arg Tyr Thr Met Ile Thr Ala Leu Gly Leu Leu Thr Ala Tyr Ile Phe<br>                        180                        185                        190 | | 576 |
| atc ctc tac tac tgt aaa agt tta gct atg att gct gtg gga caa att<br>Ile Leu Tyr Tyr Cys Lys Ser Leu Ala Met Ile Ala Val Gly Gln Ile<br>        195                        200                        205 | | 624 |
| ctc tca gct ata cca tgg ggt tgt ttc caa agt ttg gct gtt act tat<br>Leu Ser Ala Ile Pro Trp Gly Cys Phe Gln Ser Leu Ala Val Thr Tyr<br>210                        215                        220 | | 672 |
| gct tcg gaa gtt tgc cct tta gca tta aga tat tac atg acc agt tac<br>Ala Ser Glu Val Cys Pro Leu Ala Leu Arg Tyr Tyr Met Thr Ser Tyr<br>225                        230                        235                        240 | | 720 |
| tcc aac att tgt tgg tta ttt ggt caa atc ttc gcc tct ggt att atg<br>Ser Asn Ile Cys Trp Leu Phe Gly Gln Ile Phe Ala Ser Gly Ile Met<br>                        245                        250                        255 | | 768 |
| aaa aac tca caa gag aat tta ggg aac tcc gac ttg ggc tat aaa ttg<br>Lys Asn Ser Gln Glu Asn Leu Gly Asn Ser Asp Leu Gly Tyr Lys Leu<br>                        260                        265                        270 | | 816 |
| cca ttt gct tta caa tgg att tgg cct gct cct tta atg atc ggt atc<br>Pro Phe Ala Leu Gln Trp Ile Trp Pro Ala Pro Leu Met Ile Gly Ile<br>                  275                        280                        285 | | 864 |
| ttt ttc gct cct gag tcg ccc tgg tgg ttg gtg aga aag gat agg gtc<br>Phe Phe Ala Pro Glu Ser Pro Trp Trp Leu Val Arg Lys Asp Arg Val<br>290                        295                        300 | | 912 |
| gct gag gca aga aaa tct tta agc aga att ttg agt ggt aaa ggc gcc<br>Ala Glu Ala Arg Lys Ser Leu Ser Arg Ile Leu Ser Gly Lys Gly Ala<br>305                        310                        315                        320 | | 960 |
| gag aag gac att caa gtt gat ctt act tta aag cag att gaa ttg act<br>Glu Lys Asp Ile Gln Val Asp Leu Thr Leu Lys Gln Ile Glu Leu Thr<br>                        325                        330                        335 | | 1008 |
| att gaa aaa gaa aga ctt tta gca tct aaa tca gga tca ttc ttt aat<br>Ile Glu Lys Glu Arg Leu Leu Ala Ser Lys Ser Gly Ser Phe Phe Asn<br>                  340                        345                        350 | | 1056 |
| tgt ttc aag gga gtt aat gga aga aga acg aga ctt gca tgt tta act<br>Cys Phe Lys Gly Val Asn Gly Arg Arg Thr Arg Leu Ala Cys Leu Thr<br>355                        360                        365 | | 1104 |
| tgg gta gct caa aat agt agc ggt gcc gtt tta ctt ggt tac tcg aca<br>Trp Val Ala Gln Asn Ser Ser Gly Ala Val Leu Leu Gly Tyr Ser Thr<br>        370                        375                        380 | | 1152 |
| tat ttt ttt gaa aga gca ggt atg gcc acc gac aag gcg ttt act ttt<br>Tyr Phe Phe Glu Arg Ala Gly Met Ala Thr Asp Lys Ala Phe Thr Phe<br>385                        390                        395                        400 | | 1200 |
| tct cta att cag tac tgt ctt ggg tta gcg ggt aca ctt tgc tcc tgg<br>Ser Leu Ile Gln Tyr Cys Leu Gly Leu Ala Gly Thr Leu Cys Ser Trp<br>                        405                        410                        415 | | 1248 |
| gta ata tct ggc cgt gtt ggt aga tgg aca ata ctg acc tat ggt ctt<br>Val Ile Ser Gly Arg Val Gly Arg Trp Thr Ile Leu Thr Tyr Gly Leu<br>                        420                        425                        430 | | 1296 |
| gca ttt caa atg gtc tgc tta ttt att att ggt gga atg ggt ttt ggt<br>Ala Phe Gln Met Val Cys Leu Phe Ile Ile Gly Gly Met Gly Phe Gly<br>        435                        440                        445 | | 1344 |

```
tct gga agc agc gct agt aat ggt gcc ggt ggt tta ttg ctg gct tta    1392
Ser Gly Ser Ser Ala Ser Asn Gly Ala Gly Gly Leu Leu Leu Ala Leu
    450                 455                 460 tca ttc ttt tac aat gct ggt atc ggt gca gtt gtt tac tgt atc gtt    1440
Ser Phe Phe Tyr Asn Ala Gly Ile Gly Ala Val Val Tyr Cys Ile Val
465                 470                 475                 480 gct gaa att cca tca gcg gag ttg aga act aag act ata gtg ctg gcc    1488
Ala Glu Ile Pro Ser Ala Glu Leu Arg Thr Lys Thr Ile Val Leu Ala
                485                 490                 495 cgt att tgc tac aat ctc atg gcc gtt att aac gct ata tta acg ccc    1536
Arg Ile Cys Tyr Asn Leu Met Ala Val Ile Asn Ala Ile Leu Thr Pro
            500                 505                 510 tat atg cta aac gtg agc gat tgg aac tgg ggt gcc aaa act ggt cta    1584
Tyr Met Leu Asn Val Ser Asp Trp Asn Trp Gly Ala Lys Thr Gly Leu
        515                 520                 525 tac tgg ggt ggt ttc aca gca gtc act tta gct tgg gtc atc atc gat    1632
Tyr Trp Gly Gly Phe Thr Ala Val Thr Leu Ala Trp Val Ile Ile Asp
    530                 535                 540 ctg cct gag aca act ggt aga acc ttc agt gaa att aat gaa ctt ttc    1680
Leu Pro Glu Thr Thr Gly Arg Thr Phe Ser Glu Ile Asn Glu Leu Phe
545                 550                 555                 560 aac caa ggg gta cca gca aga aag ttc aag tcg act aaa gtc gac cct    1728
Asn Gln Gly Val Pro Ala Arg Lys Phe Lys Ser Thr Lys Val Asp Pro
                565                 570                 575 ttt gca gct gcc aaa gca gca gct gca gaa att aat gtt aaa gat ccg    1776
Phe Ala Ala Ala Lys Ala Ala Ala Glu Ile Asn Val Lys Asp Pro
            580                 585                 590 aag gaa gat ttg gaa act tct gtg gta gat gaa ggg cga aac acc tca    1824
Lys Glu Asp Leu Glu Thr Ser Val Val Asp Glu Gly Arg Asn Thr Ser
        595                 600                 605 tct gtt gtg aac aaa                                                 1839
Ser Val Val Asn Lys
    610
```

<210> SEQ ID NO 16
<211> LENGTH: 613
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Met Lys Gly Leu Ser Ser Leu Ile Asn Arg Lys Lys Asp Arg Asn Asp
1               5                   10                  15

Ser His Leu Asp Glu Ile Glu Asn Gly Val Asn Ala Thr Glu Phe Asn
            20                  25                  30

Ser Ile Glu Met Glu Glu Gln Gly Lys Lys Ser Asp Phe Gly Leu Ser
        35                  40                  45

His His Glu Tyr Gly Pro Gly Ser Leu Ile Pro Asn Asp Asn Asn Glu
    50                  55                  60

Glu Val Pro Asp Leu Leu Asp Glu Ala Met Gln Asp Ala Lys Glu Ala
65                  70                  75                  80

Asp Glu Ser Glu Arg Gly Met Pro Leu Met Thr Ala Leu Lys Thr Tyr
                85                  90                  95

Pro Lys Ala Ala Ala Trp Ser Leu Leu Val Ser Thr Thr Leu Val Met
            100                 105                 110

Glu Gly Tyr Asp Thr Ala Leu Leu Ser Ala Leu Tyr Ala Leu Pro Val
        115                 120                 125
```

```
Phe Gln Arg Lys Phe Gly Thr Leu Asn Gly Glu Gly Ser Tyr Glu Ile
130                 135                 140

Thr Ser Gln Trp Gln Ile Gly Leu Asn Met Cys Val Leu Cys Gly Glu
145                 150                 155                 160

Met Ile Gly Leu Gln Ile Thr Thr Tyr Met Val Glu Phe Met Gly Asn
                165                 170                 175

Arg Tyr Thr Met Ile Thr Ala Leu Gly Leu Leu Thr Ala Tyr Ile Phe
                180                 185                 190

Ile Leu Tyr Tyr Cys Lys Ser Leu Ala Met Ile Ala Val Gly Gln Ile
                195                 200                 205

Leu Ser Ala Ile Pro Trp Gly Cys Phe Gln Ser Leu Ala Val Thr Tyr
210                 215                 220

Ala Ser Glu Val Cys Pro Leu Ala Leu Arg Tyr Tyr Met Thr Ser Tyr
225                 230                 235                 240

Ser Asn Ile Cys Trp Leu Phe Gly Gln Ile Phe Ala Ser Gly Ile Met
                245                 250                 255

Lys Asn Ser Gln Glu Asn Leu Gly Asn Ser Asp Leu Gly Tyr Lys Leu
                260                 265                 270

Pro Phe Ala Leu Gln Trp Ile Trp Pro Ala Pro Leu Met Ile Gly Ile
                275                 280                 285

Phe Phe Ala Pro Glu Ser Pro Trp Trp Leu Val Arg Lys Asp Arg Val
290                 295                 300

Ala Glu Ala Arg Lys Ser Leu Ser Arg Ile Leu Ser Gly Lys Gly Ala
305                 310                 315                 320

Glu Lys Asp Ile Gln Val Asp Leu Thr Leu Lys Gln Ile Glu Leu Thr
                325                 330                 335

Ile Glu Lys Glu Arg Leu Leu Ala Ser Lys Ser Gly Ser Phe Phe Asn
                340                 345                 350

Cys Phe Lys Gly Val Asn Gly Arg Arg Thr Arg Leu Ala Cys Leu Thr
                355                 360                 365

Trp Val Ala Gln Asn Ser Ser Gly Ala Val Leu Leu Gly Tyr Ser Thr
                370                 375                 380

Tyr Phe Phe Glu Arg Ala Gly Met Ala Thr Asp Lys Ala Phe Thr Phe
385                 390                 395                 400

Ser Leu Ile Gln Tyr Cys Leu Gly Leu Ala Gly Thr Leu Cys Ser Trp
                405                 410                 415

Val Ile Ser Gly Arg Val Gly Arg Trp Thr Ile Leu Thr Tyr Gly Leu
                420                 425                 430

Ala Phe Gln Met Val Cys Leu Phe Ile Ile Gly Gly Met Gly Phe Gly
                435                 440                 445

Ser Gly Ser Ser Ala Ser Asn Gly Ala Gly Leu Leu Leu Ala Leu
450                 455                 460

Ser Phe Phe Tyr Asn Ala Gly Ile Gly Ala Val Val Tyr Cys Ile Val
465                 470                 475                 480

Ala Glu Ile Pro Ser Ala Glu Leu Arg Thr Lys Thr Ile Val Leu Ala
                485                 490                 495

Arg Ile Cys Tyr Asn Leu Met Ala Val Ile Asn Ala Ile Leu Thr Pro
                500                 505                 510

Tyr Met Leu Asn Val Ser Asp Trp Asn Trp Gly Ala Lys Thr Gly Leu
                515                 520                 525

Tyr Trp Gly Gly Phe Thr Ala Val Thr Leu Ala Trp Val Ile Ile Asp
                530                 535                 540

Leu Pro Glu Thr Thr Gly Arg Thr Phe Ser Glu Ile Asn Glu Leu Phe
545                 550                 555                 560
```

```
Asn Gln Gly Val Pro Ala Arg Lys Phe Lys Ser Thr Lys Val Asp Pro
            565                 570                 575

Phe Ala Ala Ala Lys Ala Ala Ala Glu Ile Asn Val Lys Asp Pro
        580                 585                 590

Lys Glu Asp Leu Glu Thr Ser Val Val Asp Glu Gly Arg Asn Thr Ser
        595                 600                 605

Ser Val Val Asn Lys
        610

<210> SEQ ID NO 17
<211> LENGTH: 1830
<212> TYPE: DNA
<213> ORGANISM: Artificial Sequence
<220> FEATURE:
<223> OTHER INFORMATION: Description of Artificial Sequence: Synthetic
      MMA polynucleotide
<220> FEATURE:
<221> NAME/KEY: CDS
<222> LOCATION: (1)..(1830)
<223> OTHER INFORMATION: MMAp

<400> SEQUENCE: 17 atg aag gga tta tcc tca tta ata aac aga aaa aaa gac agg aac gac      48
Met Lys Gly Leu Ser Ser Leu Ile Asn Arg Lys Lys Asp Arg Asn Asp
1               5                   10                  15 tca cac tta gat gag atc gag aat ggc gtg aac gct acc gaa ttc aac      96
Ser His Leu Asp Glu Ile Glu Asn Gly Val Asn Ala Thr Glu Phe Asn
            20                  25                  30 tcg ata gag atg gag gag caa ggt aag aaa agt gat ttt ggt ctt tcc     144
Ser Ile Glu Met Glu Glu Gln Gly Lys Lys Ser Asp Phe Gly Leu Ser
        35                  40                  45 cat cat gag tac ggt cca ggt tca cta ata cca aac gat aat aat gaa     192
His His Glu Tyr Gly Pro Gly Ser Leu Ile Pro Asn Asp Asn Asn Glu
    50                  55                  60 gaa gtc ccc gac ctt ctc gat gaa gct atg cag gac gcc aaa gag gca     240
Glu Val Pro Asp Leu Leu Asp Glu Ala Met Gln Asp Ala Lys Glu Ala
65                  70                  75                  80 gat gaa agt gag agg gga atg cca ctc atg aca gct ttg aag aca tat     288
Asp Glu Ser Glu Arg Gly Met Pro Leu Met Thr Ala Leu Lys Thr Tyr
                85                  90                  95 cca aaa gct gct gct tgg tca cta tta gtt tcc aca aca ttg att caa     336
Pro Lys Ala Ala Ala Trp Ser Leu Leu Val Ser Thr Thr Leu Ile Gln
            100                 105                 110 gag ggt tat gac aca gcc att cta gga gct ttc tat gcc ctg cct gtt     384
Glu Gly Tyr Asp Thr Ala Ile Leu Gly Ala Phe Tyr Ala Leu Pro Val
        115                 120                 125 ttt caa aaa aaa tat ggt tct ttg aat agc aat aca gga gat tat gaa     432
Phe Gln Lys Lys Tyr Gly Ser Leu Asn Ser Asn Thr Gly Asp Tyr Glu
    130                 135                 140 att tca gtt tct tgg caa atc ggt cta tgt cta tgc tac atg gca ggt     480
Ile Ser Val Ser Trp Gln Ile Gly Leu Cys Leu Cys Tyr Met Ala Gly
145                 150                 155                 160 gaa att gtg ggg cta cag cta acg ggg ccc tcc gtg gat ctt gtt gga     528
Glu Ile Val Gly Leu Gln Leu Thr Gly Pro Ser Val Asp Leu Val Gly
                165                 170                 175 aat cgt tac aca ttg atc atg gcg ttg ttt tta gcg gct ttc att         576
Asn Arg Tyr Thr Leu Ile Met Ala Leu Phe Phe Leu Ala Ala Phe Ile
            180                 185                 190 ttc att ctg tat ttt tgc aag agt ttg ggt atg att gcc gtg gga cag     624
Phe Ile Leu Tyr Phe Cys Lys Ser Leu Gly Met Ile Ala Val Gly Gln
        195                 200                 205
```

| | |
|---|---|
| gca ttg tgt ggt atg cca tgg ggt tgt ttc caa tgt ttg acc gtt tct<br>Ala Leu Cys Gly Met Pro Trp Gly Cys Phe Gln Cys Leu Thr Val Ser<br>210                     215                    220 | 672 |
| tat gct tct gaa att tgt cct ttg gcc cta aga tac tat ttg acg act<br>Tyr Ala Ser Glu Ile Cys Pro Leu Ala Leu Arg Tyr Tyr Leu Thr Thr<br>225                 230                   235                   240 | 720 |
| tat tct aat tta tgt tgg acg ttc ggt caa ctt ttc gct gct ggt att<br>Tyr Ser Asn Leu Cys Trp Thr Phe Gly Gln Leu Phe Ala Ala Gly Ile<br>                    245                   250                   255 | 768 |
| atg aaa aat tcc cag aac aaa tat gcc aac tca gaa cta gga tat aag<br>Met Lys Asn Ser Gln Asn Lys Tyr Ala Asn Ser Glu Leu Gly Tyr Lys<br>260                     265                    270 | 816 |
| cta cct ttt gct ttg cag tgg atc tgg ccc ctt cct ttg gcg gta ggt<br>Leu Pro Phe Ala Leu Gln Trp Ile Trp Pro Leu Pro Leu Ala Val Gly<br>                    275                   280                   285 | 864 |
| att ttt ttt gca cca gag tct cca tgg tgg ctg gtt aaa aaa gga agg<br>Ile Phe Phe Ala Pro Glu Ser Pro Trp Trp Leu Val Lys Lys Gly Arg<br>290                     295                    300 | 912 |
| att gat caa gcg agg aga tca ctt gaa aga aca tta agt ggt aaa gga<br>Ile Asp Gln Ala Arg Arg Ser Leu Glu Arg Thr Leu Ser Gly Lys Gly<br>305                     310                   315                   320 | 960 |
| ccc gag aaa gaa tta cta gtg act atg gaa ctc gat aaa atc aaa act<br>Pro Glu Lys Glu Leu Leu Val Thr Met Glu Leu Asp Lys Ile Lys Thr<br>                    325                   330                   335 | 1008 |
| act ata gaa aag gag cag aaa atg tct gat gaa gga act tac tgg gat<br>Thr Ile Glu Lys Glu Gln Lys Met Ser Asp Glu Gly Thr Tyr Trp Asp<br>340                     345                    350 | 1056 |
| tgt gtg aaa gat ggt att aac agg aga aga acg aga ata gct tgt tta<br>Cys Val Lys Asp Gly Ile Asn Arg Arg Arg Thr Arg Ile Ala Cys Leu<br>                    355                   360                   365 | 1104 |
| tgt tgg atc ggt caa tgc tcc tgt ggt gca tca tta att ggt tat tca<br>Cys Trp Ile Gly Gln Cys Ser Cys Gly Ala Ser Leu Ile Gly Tyr Ser<br>370                     375                    380 | 1152 |
| act tac ttt tat gaa aaa gct ggt gtt agc act gat acg gct ttt act<br>Thr Tyr Phe Tyr Glu Lys Ala Gly Val Ser Thr Asp Thr Ala Phe Thr<br>385                     390                   395                   400 | 1200 |
| ttc agt att atc caa tat tgt ctt ggt att gct gca acg ttt gta tcc<br>Phe Ser Ile Ile Gln Tyr Cys Leu Gly Ile Ala Ala Thr Phe Val Ser<br>                    405                   410                   415 | 1248 |
| tgg tgg gct tca aaa tat tgt ggc aga ttt gac ctt tat gct ttt ggg<br>Trp Trp Ala Ser Lys Tyr Cys Gly Arg Phe Asp Leu Tyr Ala Phe Gly<br>                      420                   425                   430 | 1296 |
| ctg gct ttt cag gct att atg ttc ttc att atc ggt ggt tta gga tgt<br>Leu Ala Phe Gln Ala Ile Met Phe Phe Ile Ile Gly Gly Leu Gly Cys<br>                    435                   440                   445 | 1344 |
| tca gac act cat ggc gct aaa atg ggt agt ggt gct ctt cta atg gtt<br>Ser Asp Thr His Gly Ala Lys Met Gly Ser Gly Ala Leu Leu Met Val<br>450                     455                    460 | 1392 |
| gtc gcg ttc ttt tac aac ctc ggt att gca cct gtt gtt ttt tgc tta<br>Val Ala Phe Phe Tyr Asn Leu Gly Ile Ala Pro Val Val Phe Cys Leu<br>465                     470                   475                   480 | 1440 |
| gtg tct gaa atg ccg tct tca agg cta aga acc aaa aca att att ttg<br>Val Ser Glu Met Pro Ser Ser Arg Leu Arg Thr Lys Thr Ile Ile Leu<br>                    485                   490                   495 | 1488 |
| gct cgt aat gct tac aat gtg atc caa gtt gta gtt aca gtt ttg att<br>Ala Arg Asn Ala Tyr Asn Val Ile Gln Val Val Val Thr Val Leu Ile<br>                    500                   505                   510 | 1536 |
| atg tac caa ttg aac tca gag aaa tgg aat tgg ggt gct aaa tca ggc<br>Met Tyr Gln Leu Asn Ser Glu Lys Trp Asn Trp Gly Ala Lys Ser Gly<br>                    515                   520                   525 | 1584 |

```
ttt ttc tgg gga gga ttt tgt ctg gcc act tta gct tgg gct gtt gtc    1632
Phe Phe Trp Gly Gly Phe Cys Leu Ala Thr Leu Ala Trp Ala Val Val
    530                 535                 540 gat tta cca gaa acc gct ggc agg act ttt att gag ata aat gaa ttg    1680
Asp Leu Pro Glu Thr Ala Gly Arg Thr Phe Ile Glu Ile Asn Glu Leu
545                 550                 555                 560 ttt aga ctt ggg gta cct gcc aga aaa ttt gca tct act gtg gtt gat    1728
Phe Arg Leu Gly Val Pro Ala Arg Lys Phe Ala Ser Thr Val Val Asp
                565                 570                 575 cca ttc gga aag gga aaa act caa cat gat tcg cta gct gat gag agt    1776
Pro Phe Gly Lys Gly Lys Thr Gln His Asp Ser Leu Ala Asp Glu Ser
            580                 585                 590 atc agt cag tcc tca agc ata aaa cag cga gaa tta aat gca gct gat    1824
Ile Ser Gln Ser Ser Ser Ile Lys Gln Arg Glu Leu Asn Ala Ala Asp
        595                 600                 605 aaa tgt                                                             1830
Lys Cys
    610

<210> SEQ ID NO 18
<211> LENGTH: 610
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Lys Gly Leu Ser Ser Leu Ile Asn Arg Lys Lys Asp Arg Asn Asp
1               5                   10                  15

Ser His Leu Asp Glu Ile Glu Asn Gly Val Asn Ala Thr Glu Phe Asn
            20                  25                  30

Ser Ile Glu Met Glu Glu Gln Gly Lys Lys Ser Asp Phe Gly Leu Ser
        35                  40                  45

His His Glu Tyr Gly Pro Gly Ser Leu Ile Pro Asn Asp Asn Asn Glu
    50                  55                  60

Glu Val Pro Asp Leu Leu Asp Glu Ala Met Gln Asp Ala Lys Glu Ala
65                  70                  75                  80

Asp Glu Ser Glu Arg Gly Met Pro Leu Met Thr Ala Leu Lys Thr Tyr
                85                  90                  95

Pro Lys Ala Ala Ala Trp Ser Leu Leu Val Ser Thr Thr Leu Ile Gln
            100                 105                 110

Glu Gly Tyr Asp Thr Ala Ile Leu Gly Ala Phe Tyr Ala Leu Pro Val
        115                 120                 125

Phe Gln Lys Lys Tyr Gly Ser Leu Asn Ser Asn Thr Gly Asp Tyr Glu
    130                 135                 140

Ile Ser Val Ser Trp Gln Ile Gly Leu Cys Leu Cys Tyr Met Ala Gly
145                 150                 155                 160

Glu Ile Val Gly Leu Gln Leu Thr Gly Pro Ser Val Asp Leu Val Gly
                165                 170                 175

Asn Arg Tyr Thr Leu Ile Met Ala Leu Phe Phe Leu Ala Ala Phe Ile
            180                 185                 190

Phe Ile Leu Tyr Phe Cys Lys Ser Leu Gly Met Ile Ala Val Gly Gln
        195                 200                 205

Ala Leu Cys Gly Met Pro Trp Gly Cys Phe Gln Cys Leu Thr Val Ser
    210                 215                 220

Tyr Ala Ser Glu Ile Cys Pro Leu Ala Leu Arg Tyr Tyr Leu Thr Thr
225                 230                 235                 240
```

Tyr Ser Asn Leu Cys Trp Thr Phe Gly Gln Leu Phe Ala Ala Gly Ile
            245                 250                 255

Met Lys Asn Ser Gln Asn Lys Tyr Ala Asn Ser Glu Leu Gly Tyr Lys
            260                 265                 270

Leu Pro Phe Ala Leu Gln Trp Ile Trp Pro Leu Pro Leu Ala Val Gly
            275                 280                 285

Ile Phe Phe Ala Pro Glu Ser Pro Trp Trp Leu Val Lys Lys Gly Arg
            290                 295                 300

Ile Asp Gln Ala Arg Arg Ser Leu Glu Arg Thr Leu Ser Gly Lys Gly
305                 310                 315                 320

Pro Glu Lys Glu Leu Leu Val Thr Met Glu Leu Asp Lys Ile Lys Thr
                325                 330                 335

Thr Ile Glu Lys Glu Gln Lys Met Ser Asp Glu Gly Thr Tyr Trp Asp
            340                 345                 350

Cys Val Lys Asp Gly Ile Asn Arg Arg Thr Arg Ile Ala Cys Leu
            355                 360                 365

Cys Trp Ile Gly Gln Cys Ser Cys Gly Ala Ser Leu Ile Gly Tyr Ser
            370                 375                 380

Thr Tyr Phe Tyr Glu Lys Ala Gly Val Ser Thr Asp Thr Ala Phe Thr
385                 390                 395                 400

Phe Ser Ile Ile Gln Tyr Cys Leu Gly Ile Ala Ala Thr Phe Val Ser
                405                 410                 415

Trp Trp Ala Ser Lys Tyr Cys Gly Arg Phe Asp Leu Tyr Ala Phe Gly
                420                 425                 430

Leu Ala Phe Gln Ala Ile Met Phe Phe Ile Ile Gly Gly Leu Gly Cys
            435                 440                 445

Ser Asp Thr His Gly Ala Lys Met Gly Ser Gly Ala Leu Leu Met Val
450                 455                 460

Val Ala Phe Phe Tyr Asn Leu Gly Ile Ala Pro Val Val Phe Cys Leu
465                 470                 475                 480

Val Ser Glu Met Pro Ser Ser Arg Leu Arg Thr Lys Thr Ile Ile Leu
                485                 490                 495

Ala Arg Asn Ala Tyr Asn Val Ile Gln Val Val Val Thr Val Leu Ile
            500                 505                 510

Met Tyr Gln Leu Asn Ser Glu Lys Trp Asn Trp Gly Ala Lys Ser Gly
            515                 520                 525

Phe Phe Trp Gly Gly Phe Cys Leu Ala Thr Leu Ala Trp Ala Val Val
            530                 535                 540

Asp Leu Pro Glu Thr Ala Gly Arg Thr Phe Ile Glu Ile Asn Glu Leu
545                 550                 555                 560

Phe Arg Leu Gly Val Pro Ala Arg Lys Phe Ala Ser Thr Val Val Asp
                565                 570                 575

Pro Phe Gly Lys Gly Lys Thr Gln His Asp Ser Leu Ala Asp Glu Ser
            580                 585                 590

Ile Ser Gln Ser Ser Ser Ile Lys Gln Arg Glu Leu Asn Ala Ala Asp
            595                 600                 605

Lys Cys
    610

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 19
agagctcagc atataaagag aca                                          23

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tggatccgta tctacctact gg                                           22

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgagctcaca tagaagaaca tcaaa                                        25

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
atggatccat atgaaaaata tcatt                                        25

<210> SEQ ID NO 23
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gtaaaacgac ggccagt                                                 17

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggaaacagct atgaccatg                                               19

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tgtcgactac cctggttatg                                        20

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
agtcgacact aatatggacc a                                      21

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gggtacctgc cagaaaattt                                        20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
aggtacccct tggttgaaaa                                        20

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tgtcgacaac attgattcaa gag                                    23

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tgtcgacact aatagtgacc aag                                    23

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gggtaccagc aagaaagttc aa                                     22

```
<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tggtacccca agtctaaaca att                                              23

<210> SEQ ID NO 33
<211> LENGTH: 1845
<212> TYPE: DNA
<213> ORGANISM: Saccharomyces cerevisiae

<400> SEQUENCE: 33
atgaagggat tatcctcatt aataaacaga aaaaaagaca ggaacgactc acacttagat      60
gagatcgaga atggcgtgaa cgctaccgaa ttcaactcga tagagatgga ggagcaaggt     120
aagaaaagtg attttggtct ttcccatcat gagtacggtc caggttcact aataccaaac     180
gataataatg aagaagtccc cgaccttctc gatgaagcta tgcaggacgc caaagaggca     240
gatgaaagtg agaggggaat gccactcatg acagctttga agacatatcc aaaagctgct     300
gcttggtcac tattagtttc cacaacattg attcaagagg ttatgacac agccattcta      360 ggagctttct atgccctgcc tgtttttcaa aaaaatatg gttctttgaa tagcaataca      420
ggagattatg aaatttcagt ttcttggcaa atcggtctat gtctatgcta catggcaggt     480
gaaattgtgg ggctacagct aacgggggcc tccgtggatc ttgttggaaa tcgttacaca     540
ttgatcatgg cgttgttctt tttagcggct tcatttttca ttctgtattt ttgcaagagt     600
ttgggtatga ttgccgtggg acaggcattg tgtggtatgc catggggttg tttccaatgt     660
ttgaccgttt cttatgcttc tgaaatttgt cctttggccc taagtacta tttgacgact      720 tattctaatt tatgttggac gttcggtcaa cttttcgctg ctggtattat gaaaaattcc     780
cagaacaaat atgccaactc agaactagga tataagctac cttttgcttt gcagtggatc     840 tggcccttc ctttggcggt aggtattttt tttgcaccag agtctccatg gtggctggtt      900
aaaaaaggaa ggattgatca agcgaggaga tcacttgaaa aacattaag tggtaaagga      960 cccgagaaag aattactagt gactatggaa ctcgataaaa tcaaaactac tatagaaaag    1020
gagcagaaaa tgtctgatga aggaacttac tgggattgtg tgaaagatgg tattaacagg    1080
agaagaacga aatagcttg tttatgttgg atcggtcaat gctcctgtgg tgcatcatta     1140
attggttatt caacttactt ttatgaaaaa gctggtgtta gcactgatac ggcttttact    1200
ttcagtatta tccaatattg tcttggtatt gctgcaacgt ttgtatcctg gtgggcttca    1260
aaatattgtg gcagatttga cctttatgct tttgggctgg cttttcaggc tattatgttc    1320
ttcattatcg gtggtttagg atgttcagac actcatggcg ctaaaatggg tagtggtgct    1380
cttctaatgg ttgtcgcgtt cttttacaac ctcggtattg cacctgttgt ttttgctta     1440 gtgtctgaaa tgccgtcttc aaggctaaga accaaaacaa ttattttggc tcgtaatgct    1500
tacaatgtga tccaagttgt agttacagtt ttgattatgt accaattgaa ctcagagaaa    1560
tggaattggg gtgctaaatc aggctttttc tggggaggat tttgtctggc cactttagct    1620
tgggctgttg tcgatttacc agaaccgct ggcaggactt ttattgagat aaatgaattg     1680
tttagacttg gtgttccagc aagaaagttc aagtcgacta aagtcgaccc ttttgcagct    1740
```

-continued

| | |
|---|---|
| gccaaagcag cagctgcaga aattaatgtt aaagatccga aggaagattt ggaaacttct | 1800 |
| gtggtagatg aagggcgaaa cacctcatct gttgtgaaca aatga | 1845 |